(12) United States Patent
Hudson et al.

(10) Patent No.: US 11,730,475 B2
(45) Date of Patent: Aug. 22, 2023

(54) SURGICAL STAPLER HAVING A POWERED HANDLE

(71) Applicant: Applied Medical Resources Corporation, Rancho Santa Margarita, CA (US)

(72) Inventors: Kevin Hudson, Rancho Santa Margarita, CA (US); Andy Pham, Rancho Santa Margarita, CA (US); Jonathan R. Nash, Rancho Santa Margarita, CA (US); Zachary W. Gyugyi, Irvine, CA (US); Travis Bautista, Rancho Santa Margarita, CA (US); Jonathan Von Stein, Rancho Santa Margarita, CA (US); Ata Kiraz, Rancho Santa Margarita, CA (US); Eric J. Weiss, San Clemente, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 17/514,748

(22) Filed: Oct. 29, 2021

(65) Prior Publication Data
US 2022/0133318 A1 May 5, 2022

Related U.S. Application Data

(60) Provisional application No. 63/107,336, filed on Oct. 29, 2020.

(51) Int. Cl.
*A61B 17/072* (2006.01)
*A61B 17/00* (2006.01)

(52) U.S. Cl.
CPC ............ *A61B 17/07207* (2013.01); *A61B 2017/0046* (2013.01); *A61B 2017/00398* (2013.01)

(58) Field of Classification Search
CPC .... A61B 17/07207; A61B 2017/00398; A61B 2017/0046
(Continued)

(56) References Cited

U.S. PATENT DOCUMENTS 2,073,960 A 3/1937 Crosby
2,140,593 A 12/1938 Pankonin
(Continued)

FOREIGN PATENT DOCUMENTS

EP 0 251 444 A1 1/1988
EP 0 492 283 A1 7/1992
(Continued)

OTHER PUBLICATIONS

European Patent Office, European Search Report for European Application No. 07784007.2, entitled "Surgical Stapler," dated Jun. 15, 2012, 6 pgs.
(Continued)

*Primary Examiner* — Dariush Seif
(74) *Attorney, Agent, or Firm* — John F. Heal

(57) ABSTRACT

A powered handle for a surgical stapler has a drive system including an electric motor. The powered handle includes a shaft recognition mechanism such that when a reload shaft for use with the surgical stapler is installed, a control system can actuate the drive system with the recognized shaft. The powered handle further comprises a LED light ring driven by a light control scheme to display a handle status. The control system also includes a startup module to assess hardware and control system performance before use. The startup module assesses different criteria depending on whether the handle is new, previously used, or previously reset. The control system of the powered handle further includes a lockout module configured to identify when a lockout has been encountered. The lockout module applies
(Continued)

different criteria depending on whether the motor is operating at a maximum speed state or less than a maximum speed state.

6 Claims, 57 Drawing Sheets

(58) Field of Classification Search
USPC .................................................. 227/175.1
See application file for complete search history.

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |

(56) References Cited

U.S. PATENT DOCUMENTS

| | | |
|---|---|---|
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,945,444 B2 * | 9/2005 | Gresham .............. A61B 17/115 227/181.1 |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |

(56) References Cited

U.S. PATENT DOCUMENTS

| | | |
|---|---|---|
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |

(56) References Cited

U.S. PATENT DOCUMENTS

| | | |
|---|---|---|
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 11,523,825 B2 * | 12/2022 | Becerra ............ A61B 17/07207 |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |

(56) References Cited

U.S. PATENT DOCUMENTS

| | | |
|---|---|---|
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0198272 A1 | 8/2009 | Kerver et al. |
| 2009/0206131 A1 | 8/2009 | Weisenburgh, II et al. |
| 2009/0206132 A1* | 8/2009 | Hueil .............. A61B 17/07207 227/175.2 |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Laurent et al. |
| 2011/0174099 A1* | 7/2011 | Ross .............. A61B 17/115 74/89.32 |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0228358 A1* | 9/2012 | Zemlok ............ A61B 17/07207 227/176.1 |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0116668 A1* | 5/2013 | Shelton, IV ......... A61B 17/072 606/1 |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Swayze et al. |
| 2013/0327810 A1 | 12/2013 | Shelton, IV et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |

(56) References Cited

U.S. PATENT DOCUMENTS

| | | |
|---|---|---|
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1* | 10/2014 | Shelton, IV ..... A61B 17/00234 227/175.2 |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0007621 A1 | 3/2015 | Shelton, IV et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310134 A1* | 10/2016 | Contini ............ A61B 17/07207 |
| 2016/0310204 A1 | 10/2016 | McHenry et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1* | 10/2017 | Jasemian ......... A61B 17/07207 |
| 2018/0168623 A1* | 6/2018 | Simms ................ A61B 90/94 |
| 2018/0360470 A1* | 12/2018 | Parfett ............... A61B 17/1626 |
| 2019/0125476 A1* | 5/2019 | Shelton, IV ....... A61B 17/1285 |
| 2019/0192158 A1* | 6/2019 | Scott .................. A61B 17/2833 |
| 2019/0206576 A1* | 7/2019 | Shelton, IV ............. G06T 11/60 |
| 2019/0261984 A1* | 8/2019 | Nelson ............. A61B 17/07207 |
| 2019/0290265 A1* | 9/2019 | Shelton, IV ............ G16H 40/63 |
| 2020/0268381 A1 | 8/2020 | Roberts et al. |
| 2020/0367891 A1* | 11/2020 | Kollar ................. A61B 17/1155 |
| 2020/0405304 A1* | 12/2020 | Mozdzierz ....... A61B 17/07207 |
| 2020/0405313 A1* | 12/2020 | Shelton, IV ....... A61B 17/1155 |
| 2021/0121177 A1* | 4/2021 | Jasemian ......... A61B 17/07207 |
| 2021/0196265 A1* | 7/2021 | Shelton, IV ......... A61B 17/072 |
| 2021/0196268 A1* | 7/2021 | Shelton, IV ........... H04B 15/00 |
| 2021/0290234 A1* | 9/2021 | Nelson ............. A61B 17/07207 |
| 2022/0133318 A1* | 5/2022 | Hudson ............ A61B 17/07207 227/175.1 |
| 2022/0218331 A1* | 7/2022 | Eldridge .......... A61B 17/07207 |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |

(56) References Cited

FOREIGN PATENT DOCUMENTS

| | | |
|---|---|---|
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

Ethicon Endo Surgery, Inc., Contour Curved Cutter Stapler, 2014, 2 pgs.

JustRight Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.

European Patent Office, International Search Report and Written Opinion for International Application No. PCT/US2014/028211, entitled "Surgical Stapler with Partial Pockets," dated Sep. 8, 2014, 17 pgs.

International Searching Authority, U.S., The International Search Report and the Written Opinion of the International Searching authority for international application PCT/US2014/027768, titled "Surgical Stapler with Expandable Jaw", dated Jul. 25, 2014, 17 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentability for International Application No. PCT/US2015/035379, entitled "Surgical Stapler with Circumferential Firing," dated Dec. 22, 2016, 14 pgs.

The International Bureau of WIPO, International Preliminary Report on Patentability for International Application No. PCT/US2015/050103, titled "Surgical Stapler With Self-Adjusting Staple Height," dated Mar. 30, 2017, 12 pgs.

European Patent Office, European Search Report for European Application No. EP 14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.

European Patent Office, The International Search Report and the Written Opinion of the International Searching Authority for International Application No. PCT/US2017/027213, entitled "Surgical Stapler Having a Powered Handle," dated Sep. 13, 2017, 17 pgs.

European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.

European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.

European Patent Office, Partial European Search Report for European Application No. EP 14762896.0, entitled "Surgical Stapler with Expandable Jaw," dated Apr. 10, 2017, 6 pgs.

The International Bureau of WIPO, International Preliminary Report on Patentability, for International Application No. PCT/US2016/045993, entitled "Surgical Stapler Having Locking Articulation Joint," dated Feb. 15, 2018, 13 pgs.

European Patent Office, Extended European Search Report for European Application No. EP 18186558.5, entitled "Surgical Stapler with Partial Pockets," dated Oct. 10, 2018, 9 pgs.

The International Bureau of WIPO, International Preliminary Report on Patentability, for International Application No. PCT/US2017/027142, entitled "Surgical Stapler Having Articulation Mechanism," dated Oct. 25, 2018, 12 pgs.

The International Bureau of WIPO, International Preliminary Report on Patentability, for International Application No. PCT/US2017/027213, entitled "Surgical Stapler Having Powered Handle," dated Oct. 25, 2018, 9 pgs.

The International Bureau of WIPO, International Preliminary Report on Patentability, for International Application No. PCT/US2017/027269, entitled "Reload Shaft Assembly for Surgical Stapler," dated Oct. 25, 2018, 12 pgs.

European Patent Office, Extended European Search Report for European Application No. EP 18189960.0, entitled "Surgical Stapler with Expandable Jaw," dated Dec. 13, 2018, 6 pgs.

International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.

European Patent Office, The International Search Report and the Written Opinion of the International Searching Authority for International Application No. PCT/US2019/019867, entitled "Surgical Stapler Having a Powered Handle," dated Jul. 19, 2019, 24 pgs.

European Patent Office, Extended European Search Report for European Application No. EP 19150575.9, entitled "Surgical Stapler Having Actuation Mechanism with Rotatable Shaft," dated Aug. 21, 2019, 5 pgs.

European Patent Office, Extended European Search Report for European Application No. EP 19180055.6, entitled "Surgical Stapler with Circumferential Firing," dated Sep. 20, 2019, 8 pgs.

European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.

European Patent Office, Extended European Search Report for European Application No. EP 20157713.7, entitled "Surgical Stapler with Expandable Jaw," dated May 11, 2020, 6 pgs.

European Patent Office, Extended European Search Report for European Application No. EP 20161294.2, entitled "Surgical Stapler with Self-Adjusting Staple Height," dated Jun. 22, 2020, 6 pgs.

(56) References Cited

OTHER PUBLICATIONS

European Patent Office, Extended European Search Report for European Application No. EP 20197859.0, entitled "Surgical Stapler with Circumferential Firing," dated Jan. 28, 2021, 13 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, The International Search Report and Written Opinion for International Application No. PCT/US2020/067540, dated May 3, 2021, entitled "Electrosurgical System with Tissue and Maximum Current Identification," 12 pages.
The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.
The International Bureau of WIPO, International Preliminary Report on Patentability, for International Application No. PCT/US2020/025496 entitled "Reload Cover for Surgical System," dated Oct. 14, 2021, 12 pgs.
European Patent Office, Extended European Search Report for European Application No. EP 21173771.3, entitled "Reload Shaft Assembly for Surgical Stapler," dated Aug. 27, 2021, 10 pgs.

European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" dated Feb. 23, 2022, 15 pgs.
European Patent Office, The International Search Report and the Written Opinion of the International Searching Authority for International Application No. PCT/US2021/057231, entitled "Material Combinations and Processing Methods fora Surgical Instrument" dated Feb. 11, 2022, 15 pgs.
European Patent Office, The International Search Report and the Written Opinion of the International Searching Authority for International Application No. PCT/US2021/057365, entitled "Surgical Stapler Having a Powered Handle" dated Apr. 13, 2022, 21 pgs.
European Patent Office, The International Search Report and the Written Opinion of the International Searching Authority for International Application No. PCT/US2022/012252, entitled "Surgical Stapler Having Shaft Recognition Mechanism" dated Apr. 13, 2022, 13 pgs.
European Patent Office, Extended European Search Report for European Application No. EP 22196603.9, entitled "Surgical Stapler with Expandable Jaw," dated Dec. 14, 2022, 6 pgs.

\* cited by examiner

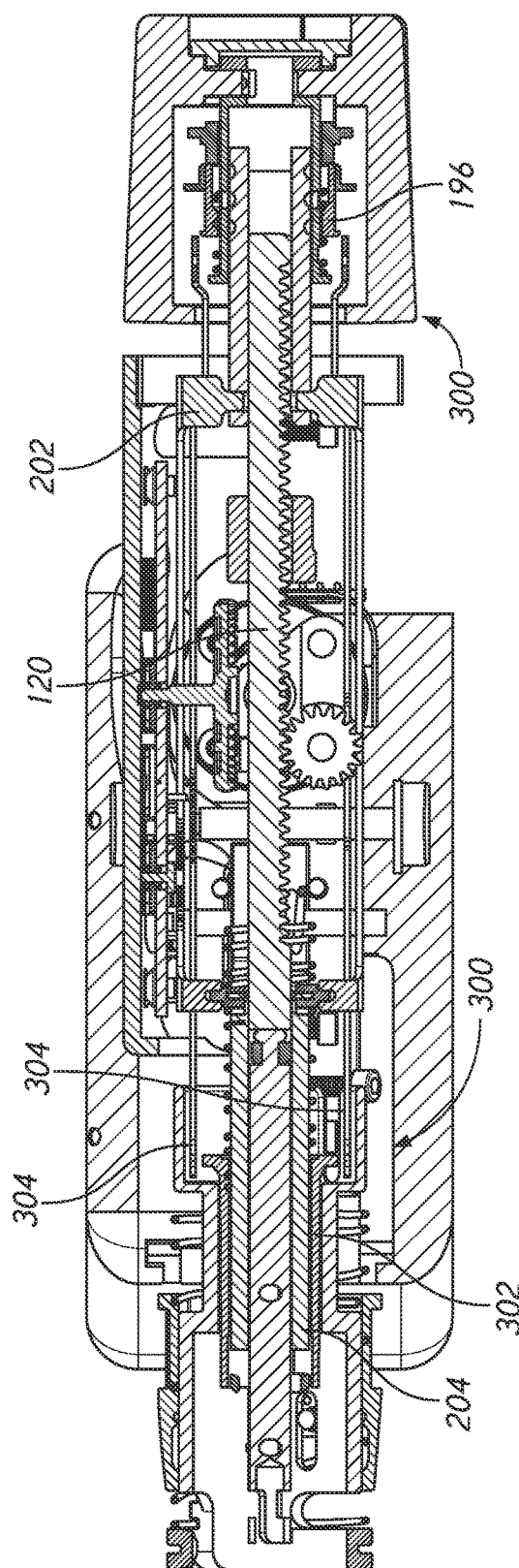
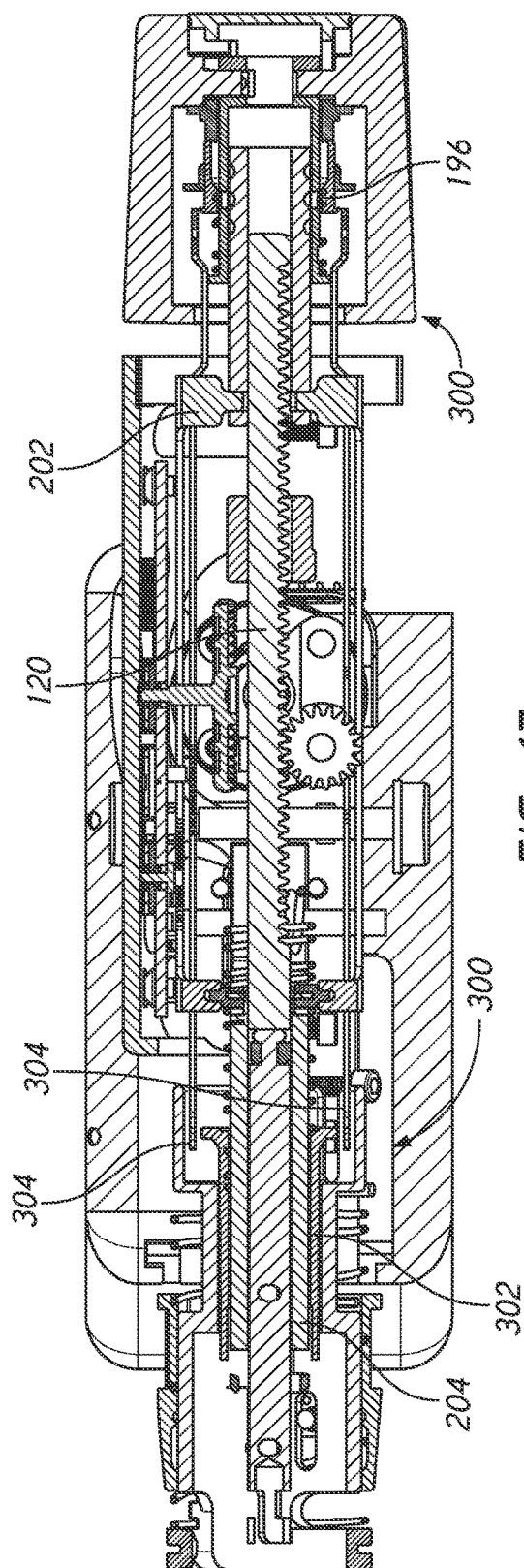

SURGICAL STAPLER HAVING A POWERED HANDLE

CROSS-REFERENCE TO RELATED APPLICATIONS

This application claims priority to and benefit of U.S. Provisional Patent Application Ser. No. 63/107,336 entitled "Surgical Stapler Having a Powered Handle" filed on Oct. 29, 2020 which is incorporated herein by reference in its entirety.

BACKGROUND OF THE INVENTION

Field of the Invention

The present application relates generally to surgical occlusion instruments and, more particularly, to powered surgical staplers.

Description of the Related Art

Surgical staplers are used to approximate or clamp tissue and to staple the clamped tissue together. As such, surgical staplers have mechanisms to clamp tissue and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

Surgical staplers having electrically powered motors can reduce the afore mentioned mechanical complexities. Powered surgical staplers can incorporate control systems to facilitate reliable operation of the stapler and communication of the stapling status to a user.

SUMMARY OF THE INVENTION

In certain embodiments, a surgical stapling system is provided herein. The surgical stapling system comprises a handle body, an electric motor, an actuation shaft, a coupler, and a shaft recognition mechanism. The handle body comprises a stationary handle and a trigger pivotably coupled to the handle body. The electric motor is disposed within the handle body. The actuation shaft is slidable within the handle body along a longitudinal axis. The coupler is configured to removably couple to a reload shaft assembly. The shaft recognition mechanism comprises a lockout sleeve longitudinally movable to a detection position upon insertion of a reload shaft to the coupler and longitudinally movable to a predetermined recognition position when the reload shaft assembly is coupled to the coupler.

In certain embodiments, a handle assembly for a surgical stapler is provided. The handle assembly comprises a handle body, an electric motor, an actuation shaft, a motor gear, an auxiliary gear, and a control system. The handle body comprises a stationary handle and a trigger pivotably coupled to the handle body. The electric motor is disposed within the handle body. The motor comprises an output shaft. The actuation shaft is slidable within the handle body along a longitudinal axis. The actuation shaft comprises a rack formed thereon. The motor gear is coupled to the output shaft of the motor. The auxiliary gear is in driven engagement with the motor gear and operatively engaged with the rack. The control system is operable to control the electric motor. The control system comprises a startup module operable upon application of power to the control system. The startup module comprises a new handle submodule, a used handle submodule, and a reset detected submodule.

In certain embodiments, a handle assembly for a surgical stapler having a removably coupled instrument shaft having a lockout mechanism is provided. The handle assembly comprises a handle body, a power system, an actuation shaft, a position sensor, and a control system. The handle body comprises a stationary handle and a trigger pivotably coupled to the handle body. The power system is within the handle body. The power system comprises a motor and a power source positionable within the handle body. The actuation shaft is operatively coupled to the power system. The actuation shaft is longitudinally slidable within the handle body. The position sensor is configured to determine the longitudinal position of the actuation shaft. The control system is electrically coupled to the power system, the trigger, and the position sensor. The control system comprises a lockout module configured to monitor a current draw of the motor and the longitudinal position of the actuation shaft and calculate a slope of a current draw profile of the motor and detect engagement of the lockout mechanism using the monitored slope. The lockout module applies a first assessment criteria to detect engagement of the lockout if the motor is operating at a maximum pulse width modulated state and a second assessment criteria to detect engagement of the lockout if the motor is not operating at a maximum pulse width modulated state.

BRIEF DESCRIPTION OF THE DRAWINGS

FIG. 16 is a cut-away top view of the powered handle of FIG. 2 with the articulation mechanism in a locked out configuration;

FIG. 17 is a cut-away top view of the powered handle of FIG. 2 with the articulation mechanism in an unlocked configuration;

DETAILED DESCRIPTION OF THE INVENTION

Figure 1:
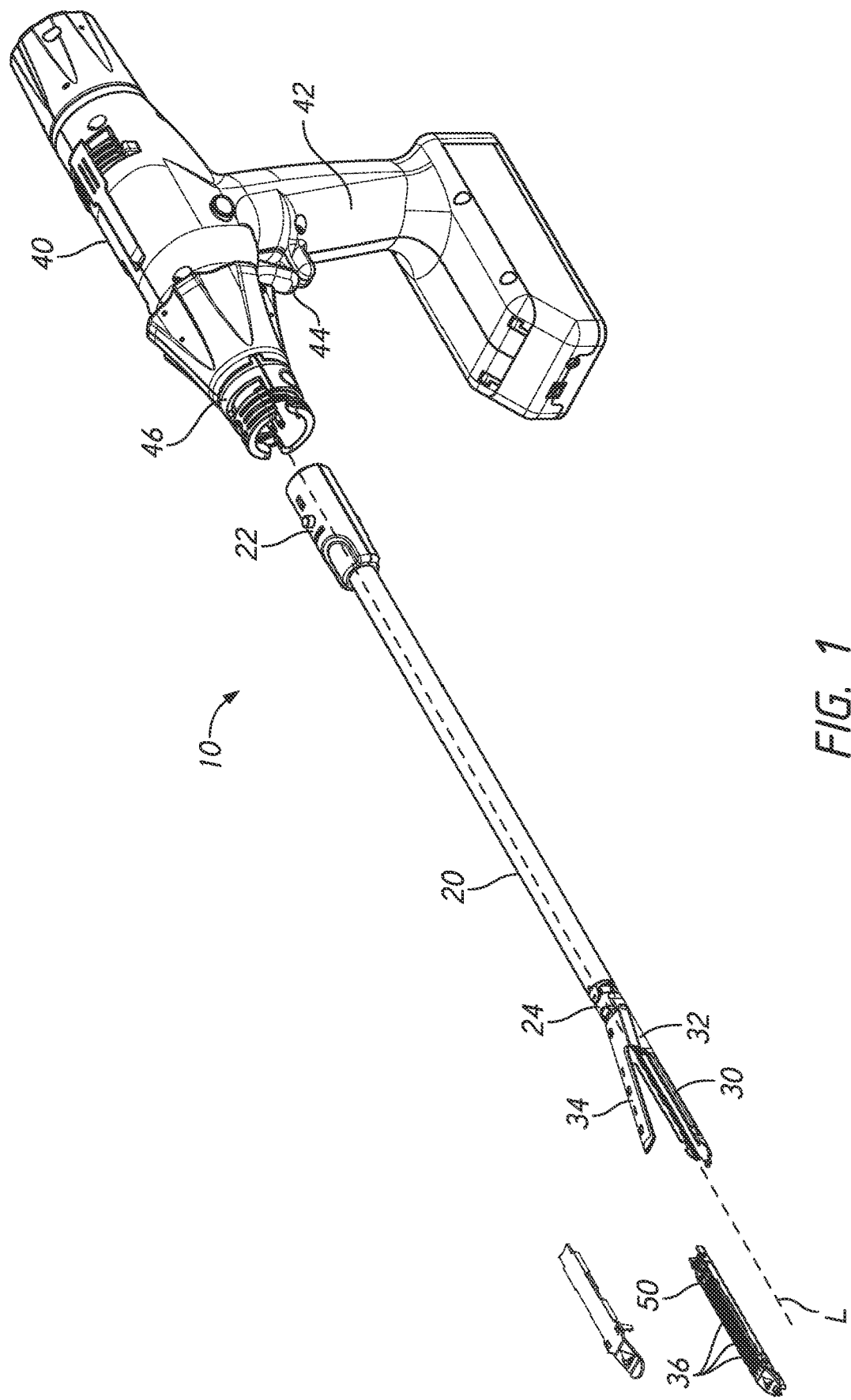
FIG. 1 is a perspective view of an embodiment of surgical stapling system having an embodiment of powered handle.
Figure 2:
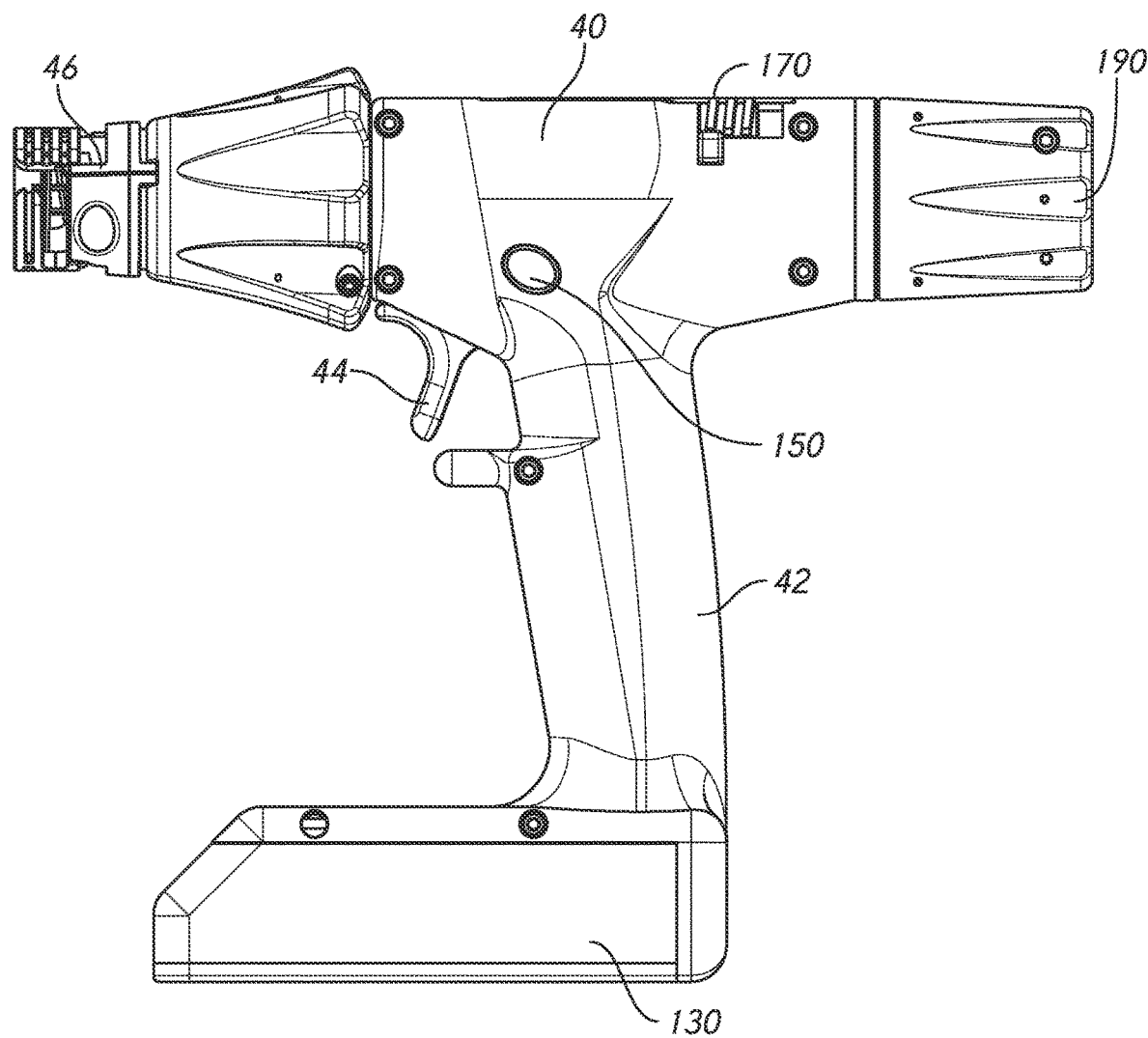
FIG. 2 is a side view of the powered handle of the surgical stapling system of FIG. 1.

With reference to FIGS. 1-2, an embodiment of surgical stapling system is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration with an embodiment of powered handle having powered staple firing and manual jaw assembly articulation. FIG. 2 illustrates the powered handle 40 of the surgical stapler system 10 with the elongate shaft removed. The powered handle 40 of FIG. 2 has powered staple firing and manual jaw assembly articulation. In the illustrated embodiments, the shaft 20 and jaw assembly 30 can be freely rotated about a longitudinal axis defined by the shaft 20 by rotation of a rotation knob on the handle 40. In other embodiments, the stapling system can be configured to allow rotation of the jaw assembly about the longitudinal axis within a predefined range or a rotationally fixed jaw assembly.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end to a distal end. The elongate shaft 20 defines a central longitudinal axis, L. of the surgical stapler 10 extending between the proximal end 22 and the distal end 24.

With continued reference to FIG. 1, in the illustrated embodiment, the jaw assembly 30 is coupled to the elongate shaft 20 at the distal end of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and is articulable with respect to the elongate shaft 20 responsive to an articulation mechanism in the handle 40. In an initial configuration, the first jaw 32 includes a plurality of staples 36 disposed therein within a reload 50. In other embodiments, the reload 50 can be integrated with the jaw assembly 30 such that the entire shaft assembly 20 and jaw assembly 30 with loaded staples define a single reload assembly. In some embodiments, staples can be initially positioned in the second jaw 34.

With continued reference to FIG. 1, in the illustrated embodiment, the jaw assembly 30 can be actuated from an open configuration (FIG. 1) to a closed configuration to a stapling configuration by a drive member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the reload 50 in the first jaw 32.

With continued reference to FIG. 1, in the illustrated embodiment, the handle assembly is configured to be coupled to the elongate shaft 20 at the proximal end of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses a powered actuation mechanism configured to selectively advance an actuation shaft responsive to movement of the movable handle 44.

In the illustrated embodiment, the surgical stapler 10 can include the plurality of staples 36 positioned in a disposable cartridge reload 50 while the jaw assembly 30 is configured to be reused with multiple staple cartridge reloads 50 in a single procedure. In the some embodiments, the elongate shaft 20 and jaw assembly 30 define a disposable reload shaft that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10. The coupler 46 can have a bayonet connection having an outer connector that can removably couple the handle assembly 42 to the elongate shaft 20, a first inner connector that can removably couple the actuation shaft of the handle assembly 42 to the drive member of the elongate shaft 20, and a second inner connector that can removably couple an articulation coupler of the handle assembly 42 to an articulation link of the elongate shaft 20. These three removable couplings occur simultaneously when an elongate shaft 20 is coupled to the handle assembly 42. Accordingly, the surgical stapler 10 can be configured such that the handle assembly 40 can be reused with multiple reload shafts 20 during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

With reference to FIG. 2, an embodiment of powered handle for a surgical stapling system is illustrated. The powered handle can be used with various shaft reloads and cartridges such that the shaft configuration, jaw assembly configuration, and staple configuration can be selected for a particular procedure. The illustrated embodiment of handle provides powered (motor-driven) clamping and opening of the jaws and firing of the staple line. Articulation of the jaw assembly can be manually controlled by an articulation knob that the operator rotates. The motor is controlled by an embedded control system that dictates functionality of the handle during different stages of use.

With continued reference to FIG. 2, the powered handle 40 comprises a pistol-grip configuration with a stationary handle 42 and a movable handle 44 or trigger pivotably coupled thereto. A power supply 130 or battery can be positioned on a lower surface of the stationary handle. The powered handle 40 can further comprise a user control such as a fire or fire/reverse button 150 to allow a user to selectively control a stapling sequence. The powered handle 40 can further comprise a redundant, manual override return system 170 to allow a user to manually return the stapling system to an open configuration in the event of a powered system failure, control system failure, power supply failure, "lockjaw," or other mechanical binding. The powered handle can further comprise a manual articulation mechanism including a rotatable articulation knob 190. In the illustrated embodiment, the articulation knob 190 is positioned on the proximal end of the powered handle and is rotatable about an axis generally corresponding to the longitudinal axis of the stapling system. In some embodiments, the powered handle can further include an illuminated user display, such as an annular light ring to display desired status indicia to a user.

Various embodiments of powered handle assemblies and associated actuation mechanisms are disclosed in U.S. patent application Ser. No. 16/287,748, filed Feb. 27, 2019, entitled "Surgical Stapler Having a Powered Handle," U.S. patent application Ser. No. 15/486,227, filed Apr. 12, 2017, entitled "Reload Shaft Assembly for Surgical Stapler," and U.S. patent application Ser. No. 15/486,008, filed Apr. 12, 2017, entitled "Surgical Stapler Having a Powered Handle," each of which is incorporated by reference herein in its entirety.

Powered Drive System

Figure 3:
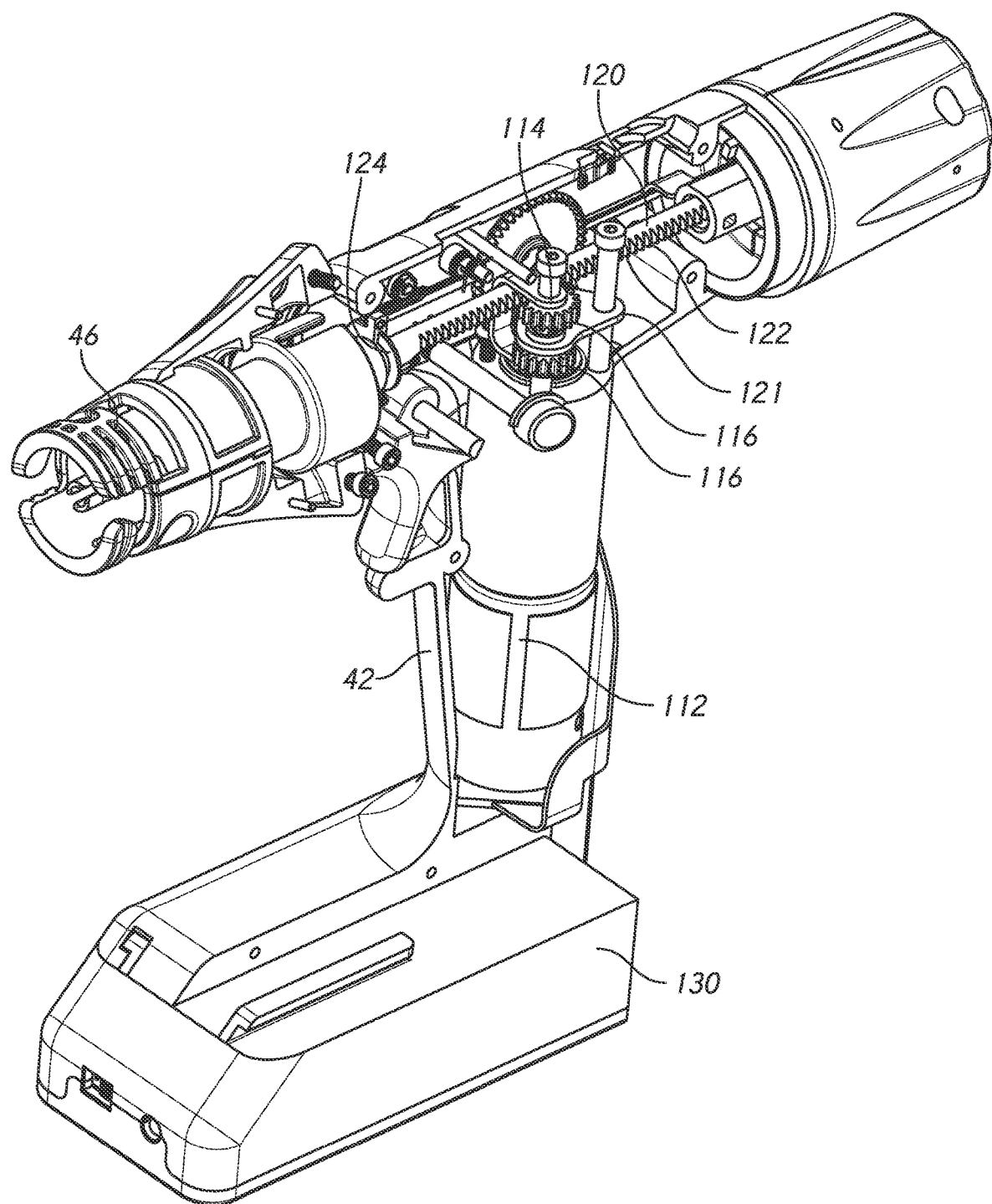
FIG. 3 is a partial cutaway perspective view of the powered handle of FIG. 2 with components removed to illustrate a drive system thereof.

With reference to FIG. 3, a partial cut-away view of the powered handle is illustrated. In the illustrated cut-away view, several components of the powered handle have been removed to clearly depict a drive system of the powered handle. In the illustrated embodiment, the drive system comprises a motor 112 positioned within the stationary handle 42, a motor gear 114 positioned on an output shaft of the motor 112, and an auxiliary gear 116 in driven engagement with the motor gear 114. In some embodiments, the motor 112 is a brushed DC gearmotor. Advantageously, transmitting power through the auxiliary gear 116 can allow the motor 112 to be laterally centered within the stationary handle to enhance handle balance and user ergonomics. Furthermore, in some embodiments, the motor gear 114 and auxiliary gear 116 can be configured to provide a desired operational torque at the rack 122. In some embodiments, the motor 112 can include a multigear transmission operationally coupled between the motor 112 and the motor gear 114 coupled to the auxiliary gear 116 to provide the desired operational torque. The motor 112 can be electrically coupled to the power supply 130 via a control system. The control system within the handle interfaces with the drive system to measure the position of the actuation shaft 120 and therefore the actuation of the jaw assembly.

The drive system is mounted to hardware that provides information to a control system including a microcontroller within the handle. This embedded system can control the speed and torque of the motor. It can also control functionality of the device based on user inputs (movement of the trigger and pressing of the FIRE/REVERSE button) and position of the drive system. The control system can also measure feedback from the motor to determine whether loads are too high to continue firing staples, or whether a reload cartridge lockout has been activated. It can also measure battery life and can limit the number of firings of the device. While the drive system is configured primarily for powered operation, in certain embodiments it can be desirable to provide a manual return mechanism to override powered operation as further described herein.

Figure 4:
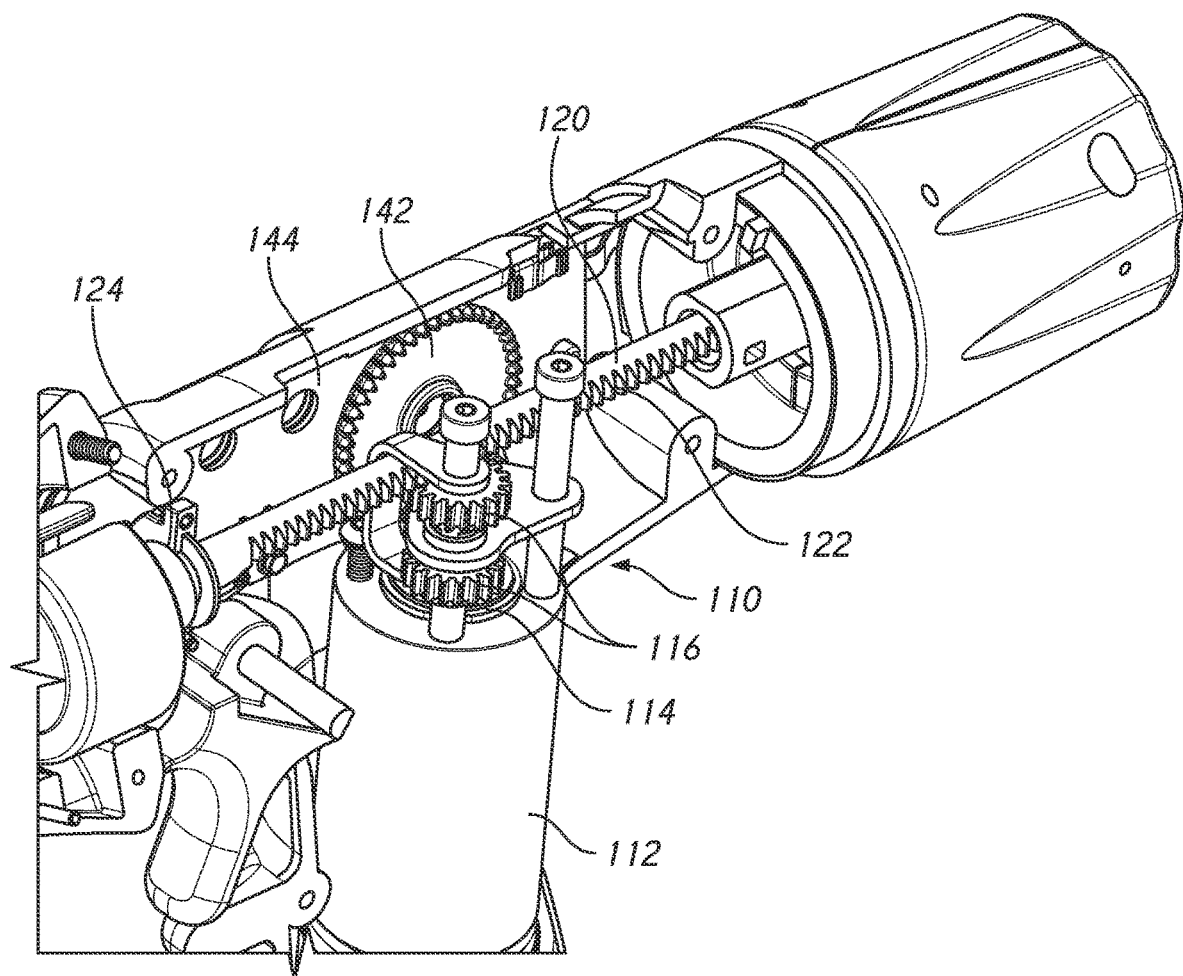
FIG. 4 is a perspective view of an embodiment of drive system for the powered handle of FIG. 2.
Figure 5:
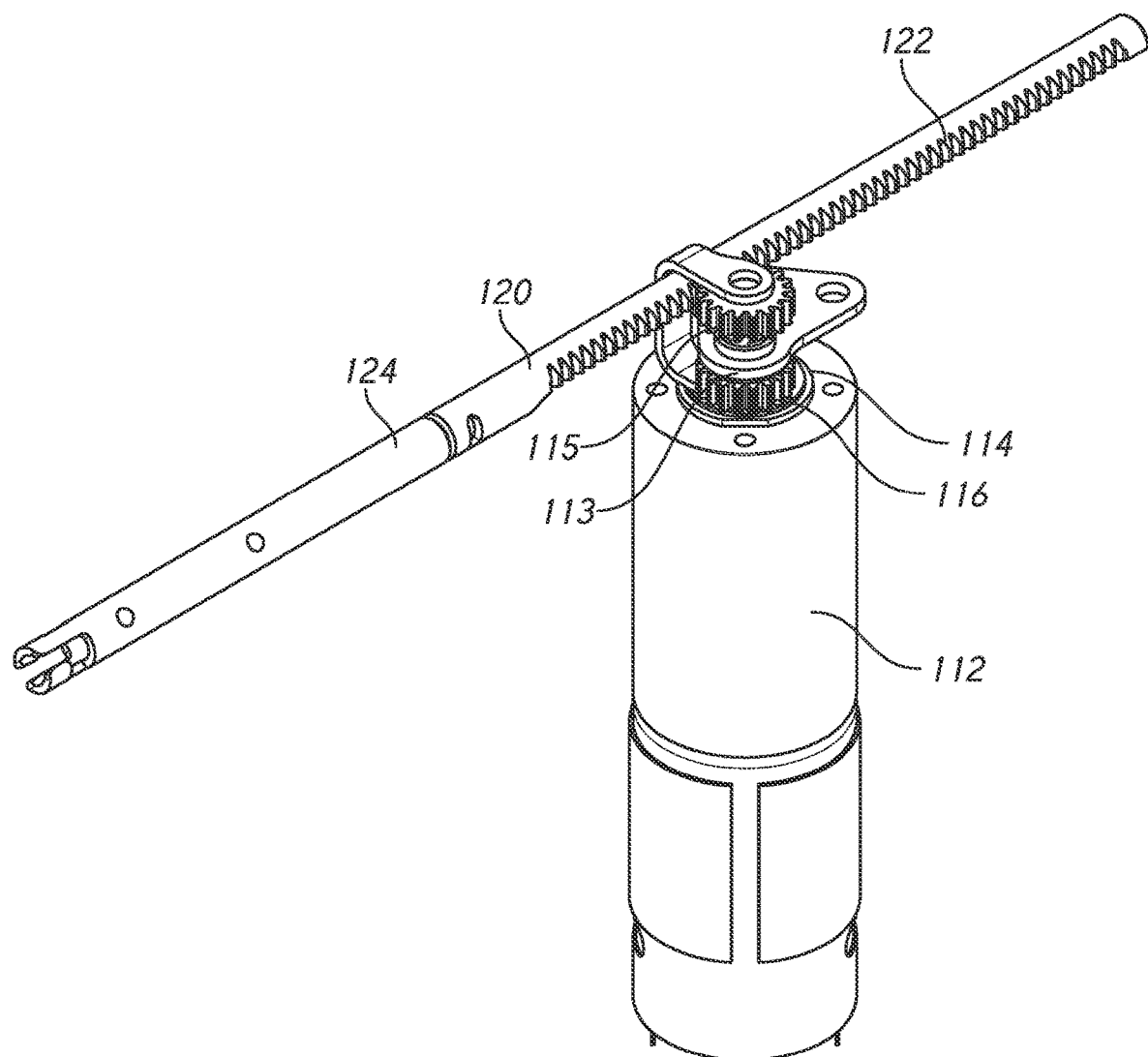
FIG. 5 is a perspective view of the drive system of FIG. 4.
Figure 6:
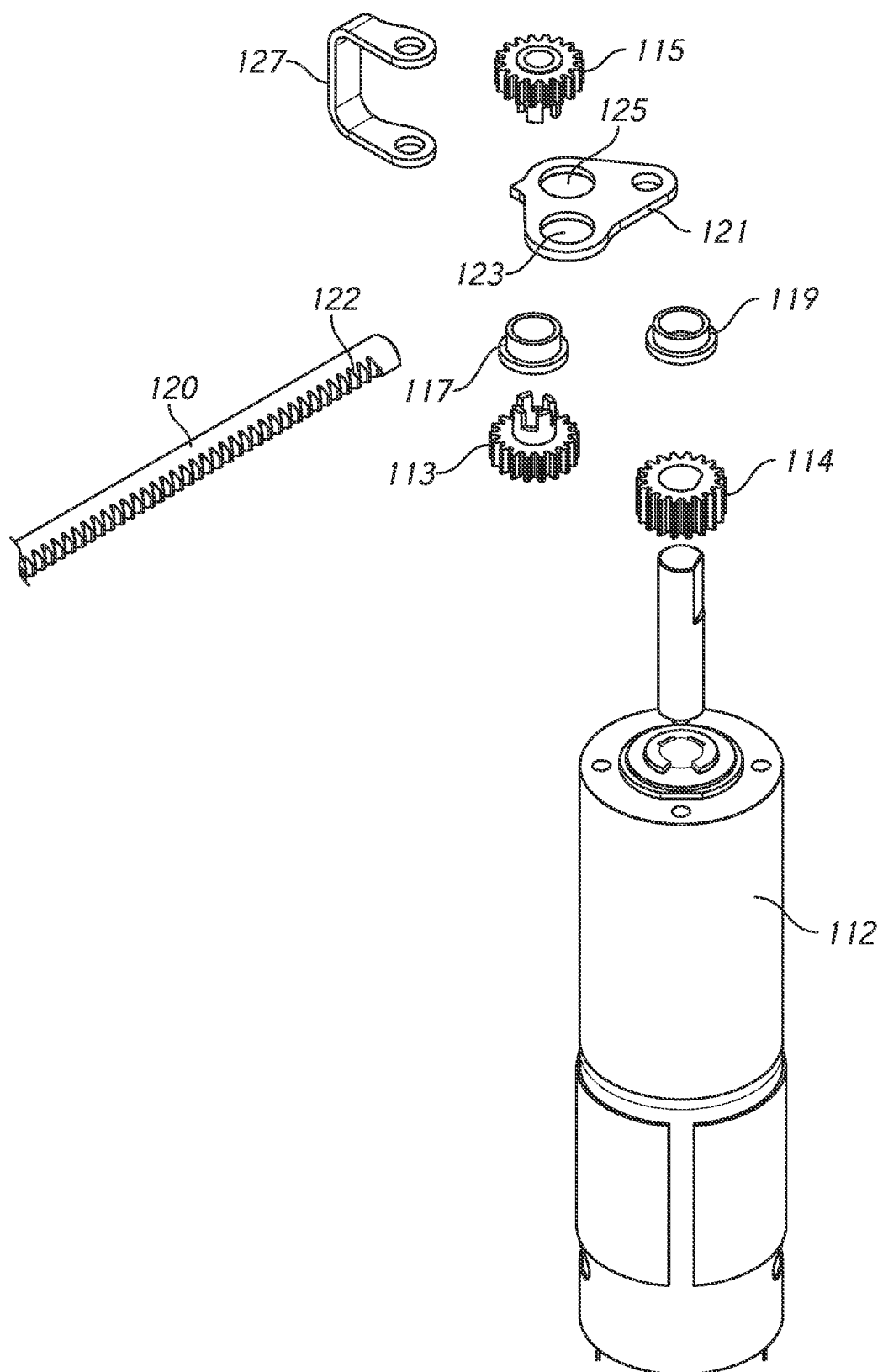
FIG. 6 is an exploded perspective view of the drive system of FIG. 4.

With reference to FIGS. 4-6, detail views of the drive system of the powered handle are illustrated. In the illustrated embodiment, the drive system comprises a bifurcated auxiliary gear 116 that is supported between its endpoints by a support plate 121. Advantageously, this supported arrangement for the auxiliary gear 116 provides a robust mechanism that can significantly reduce a tendency of the motor gear 114 from separating from the auxiliary gear 116 in heavy loading conditions.

With reference to FIGS. 5-6, the bifurcated auxiliary gear 116 comprises a first gear segment 113 rotationally coupled to a second gear segment 115. The first gear segment 113 can comprise a first engagement surface, and the second gear segment 115 can comprise a second engagement surface such that the first engagement surface and the second engagement surface can be coupled to rotationally couple the first gear segment 113 to the second gear segment 115. In the illustrated embodiment, the first gear segment 113 comprises an axially extending boss defining the first engagement surface, and the second gear segment 115 comprises an axially extending boss defining the second engagement surface. The axially extending bosses of the first gear segment and the second gear segment each comprise a square toothed or 'castle' profile that allows rotational coupling of the first gear segment 113 and the second gear segment 115. In some embodiments, when the first and second gear segments 113, 115 are rotationally coupled, the axially extending bosses are engaged to form a central region having an outer diameter that is less than an outer diameter of either of the first gear segment 113 and the second gear segment 115.

With reference to FIG. 6, an exploded view of the drive system having a bifurcated auxiliary gear 116 is illustrated. As illustrated, the drive system further comprises a support plate 121 positioned between a first end and a second end of the auxiliary gear 116. The support plate 121 can be a rigid plate having an auxiliary gear bore 123 and a motor gear bore 125 formed therein. In some embodiments, the support plate 121 can comprise a metallic material. The drive system can further comprise an auxiliary gear bushing 117 positioned in the auxiliary gear bore 123 and a motor gear bushing 119 positioned in the motor gear bore 125. The bushings117, 119 can comprise material having a relatively low coefficient of friction such as a DELRIN® material. An actuation shaft bracket or guide member 127 can facilitate engagement of the rack 122 of the actuation shaft 120 with the second gear segment 115 of the auxiliary gear 116.

With reference to FIGS. 5-6, the first gear segment 113 of the auxiliary gear 116 and the second gear segment 115 of the auxiliary gear can be assembled about the support plate 121 such that the central region of the auxiliary gear 116 extends through the auxiliary gear bore 123 and auxiliary gear bushing 117 and the auxiliary gear 116 is supported between the first end and the second end. In the illustrated embodiment, the first gear segment 113 of the auxiliary gear 116 is in geared engagement with the motor gear 114. The second gear segment 115 of the auxiliary gear 116 is in geared engagement with the rack surface 122 of the actuation shaft 120. The support plate 121 can be encapsulated by walls of the handle assembly housing and bosses formed thereon to provide support to the drive system.

Figure 7:
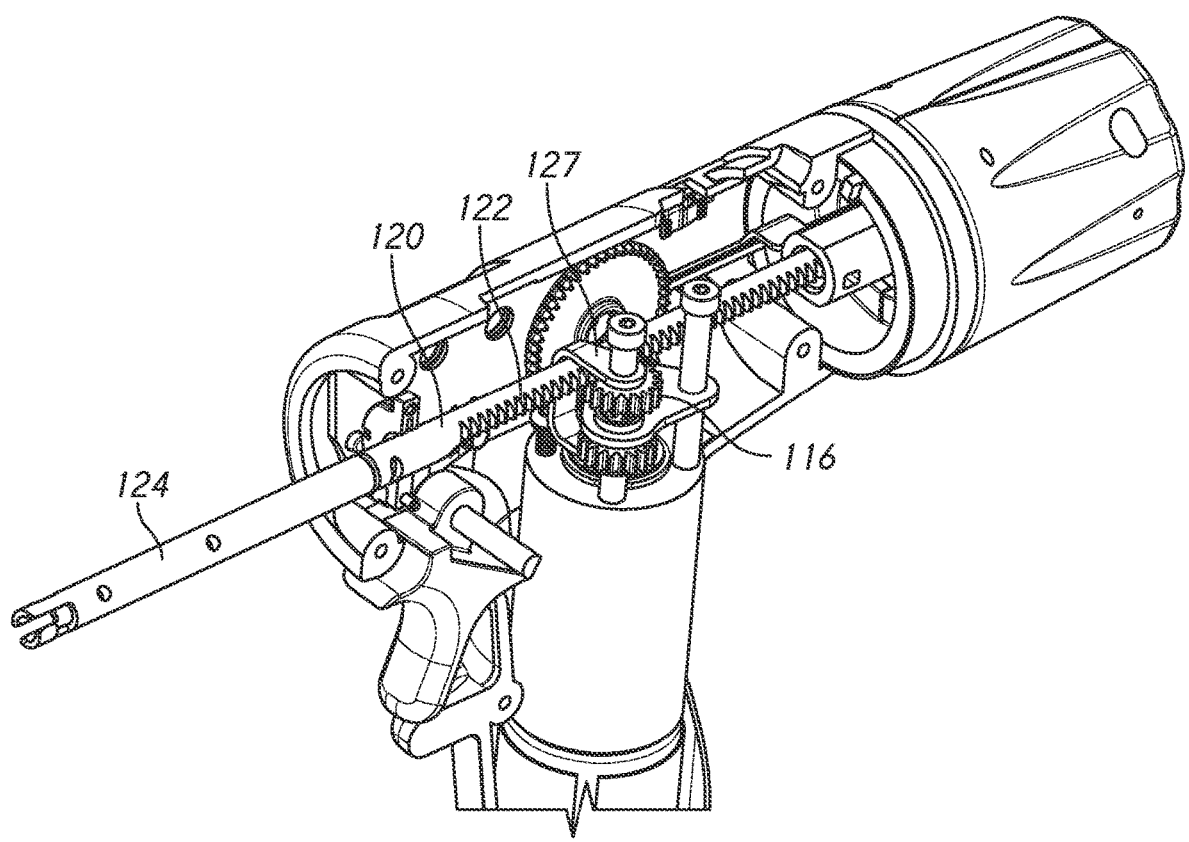
FIG. 7 is a perspective view of the drive system of FIG. 4.

With reference to FIG. 7, during powered operation, the auxiliary gear 116 is in meshed engagement with the rack 122 on an actuation shaft 120 extending longitudinally within the handle body. In the illustrated embodiment, the auxiliary gear is supported in a guide member through which the actuation shaft 120 slides. The guide member 127 assists in maintaining meshed contact between the auxiliary gear 116 and the rack 122. A distal end of the actuation shaft 120 is freely rotatably coupled to an actuation adapter 124 that extends longitudinally into the coupler 46 (FIG. 1) at the distal end of the powered handle.

With the shaft 20 coupled to the coupler 46 of the powered handle 40, the actuation adapter 124 connects to a drive member in the shaft 20 via a bayonet connection. Therefore, when the shaft 20 is attached to the handle 40, the motor 112 and rack 122 will drive a drive member extending within the instrument shaft 20 and coupled to the jaw assembly. Thus, the drive system within the handle comprises a "rack and pinion" design. Operation of the motor 112 responsive to a user's input will drive the actuation shaft 120 longitudinally forward and reverse to selectively actuate the stapler in closing, firing, or opening operations.

Figure 8:
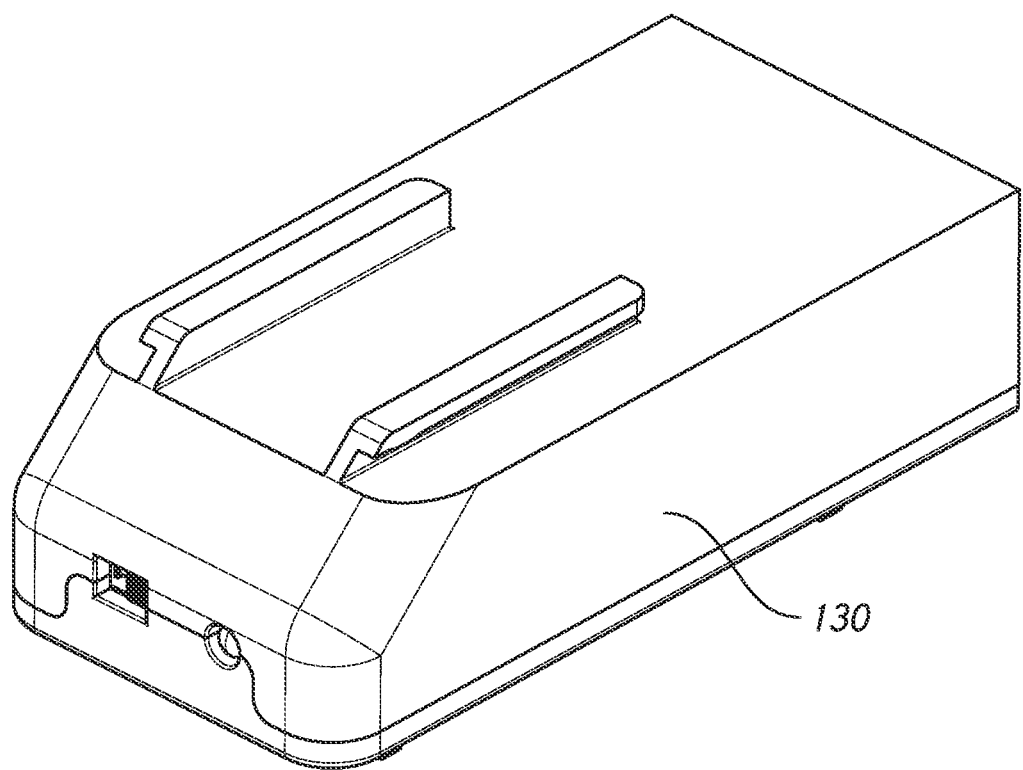
FIG. 8 is a perspective view of an embodiment of a power supply for the powered handle of FIG. 2.
Figure 9:
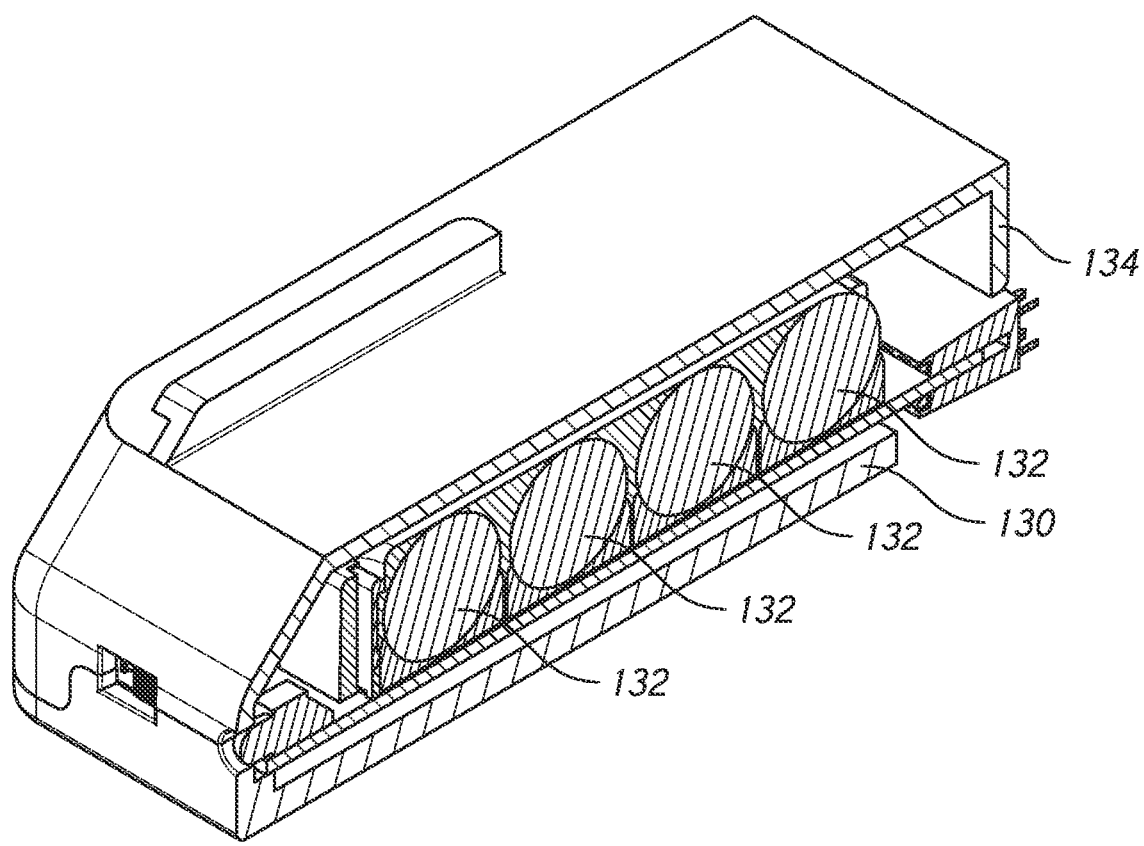
FIG. 9 is a cross-sectional perspective view of an embodiment of power supply of FIG. 8.

With reference to FIGS. 8 and 9, an embodiment of power supply 130 for the powered handle 40 is illustrated. The power supply 130 can be configured to deliver direct current to the powered handle motor and control system. In the illustrated embodiment, the stapler can operate at 12 V. The illustrated power supply can comprise four 3V lithium-ion batteries 132 connected in series to produce a 12V power supply. As illustrated, the batteries 132 are stacked in a 4 by 1 configuration in a plastic housing 134 to form the battery pack. In other embodiments, other numbers and configurations of individual battery cells can be used to form the battery pack. For example, in certain embodiments, the battery pack can be comprised of AA, AAA, or another standard or purpose-built single use or rechargeable chemistry battery. In the illustrated embodiment of powered handle 40, the battery pack is located at the bottom of the stationary handle. Desirably, this positioning provides a stable surface to set the handle 40 on a flat surface. It is contemplated that in other embodiments, the power supply can be positioned elsewhere in the handle, such as at a proximal end thereof. The power supply 130 can comprise a main power switch and indicator light, such as a light emitting diode. Through the use of lighting colors, flashing sequences, or solid illumination, the indicator light can be configured to display the power on/off status of the power supply, a low power condition, or other power supply status information, such as a recharging status.

With continued reference to FIGS. 8 and 9, in some embodiments, the power supply 130 can be packaged with the handle 40 but will not be installed before use. At the time of use, the user can install the battery pack by engaging the power supply 130 with the bottom of the handle 40. Advantageously, shipping the battery pack uninstalled can reduce an incidence of accidental battery discharge before use. Moreover, a removable battery pack can allow the stapler system be easily upgraded with a new battery as new battery technology becomes available. In other embodiments, the power supply can be packaged installed in the handle with a removable strip blocking electrical connection of the battery pack. In still other embodiments, the handle can be supplied with a power cable configured to be plugged into an AC or DC power source such as a wall socket, a USB connector, or another standard electrical connection.

In some embodiments, the power source further comprises a memory module such as a non-volatile memory that can store a digital record of the usage of the stapler. For example, the memory module can be configured to record details of each firing of the stapler including a periodic sampling of the battery voltage and motor current during firing, the sequence of states of the software state machine, any unexpected events that may have occurred, the shaft types that were used, the number of firings, the intervals between firings, and the model and serial number of the stapler handle. The memory module can be configured to record if the handle assembly usage to prevent reuse of a handle assembly intended for a single use once it has been used in a surgical procedure. It can also record if the battery pack itself has been used so that users cannot reuse the battery pack. In other embodiments, a memory module can be disposed in the handle assembly separated from the power source, such as, for example positioned on or electrically coupled to a circuit board 144 (FIG. 4), or positioned to be easily removable from an electrical port on the handle assembly, such that the memory module is not integrated with the power source.

In some embodiments, the powered handle 40 and associated power supply 130 can be configured for use in a single procedure and disposal following the procedure. The power supply 130 can include a power drain to reduce an opportunity for reuse. Following use in a surgical procedure, a user can remove the battery pack from the handle 40. Removing the battery pack from the handle 40 can initiate draining the batteries. For example, after the battery pack has been used once, a mechanical feature that can short circuit the battery by connecting the terminals to a low value resistor or an electrical feature can accomplish the same task with a circuit. Additionally, if the battery pack is left in the handle 40 after the surgical procedure is complete, in some embodiments, the control system of the handle is programmed to disable functionality and drain the battery pack after a maximum time limit. For example, in embodiments of power source including a memory module, the microcontroller can include a firing management module that can modify a memory location such as a firing count memory location, on the memory module after a predetermined number of firing strokes. The microcontroller can be configured to evaluate the firing count memory locaiton in a startup operational sequence. If this memory location indicates that the battery has been used, in some embodiments, the microcontroller can be configured to disable the stapler and activate a discharge circuit in the power source. The microcontroller can also be configured to activate the discharge circuit in other predetermined operational conditions, such as when the handle assembly has been powered on for a predetermined period, such as, in one embodiment, longer than 12 hours, has been fired more than a predetermined number of times such as, in one embodiment 12 times, had deployed a manual override return mechanism, or has experienced a non-recoverable failure.

Figure 10:
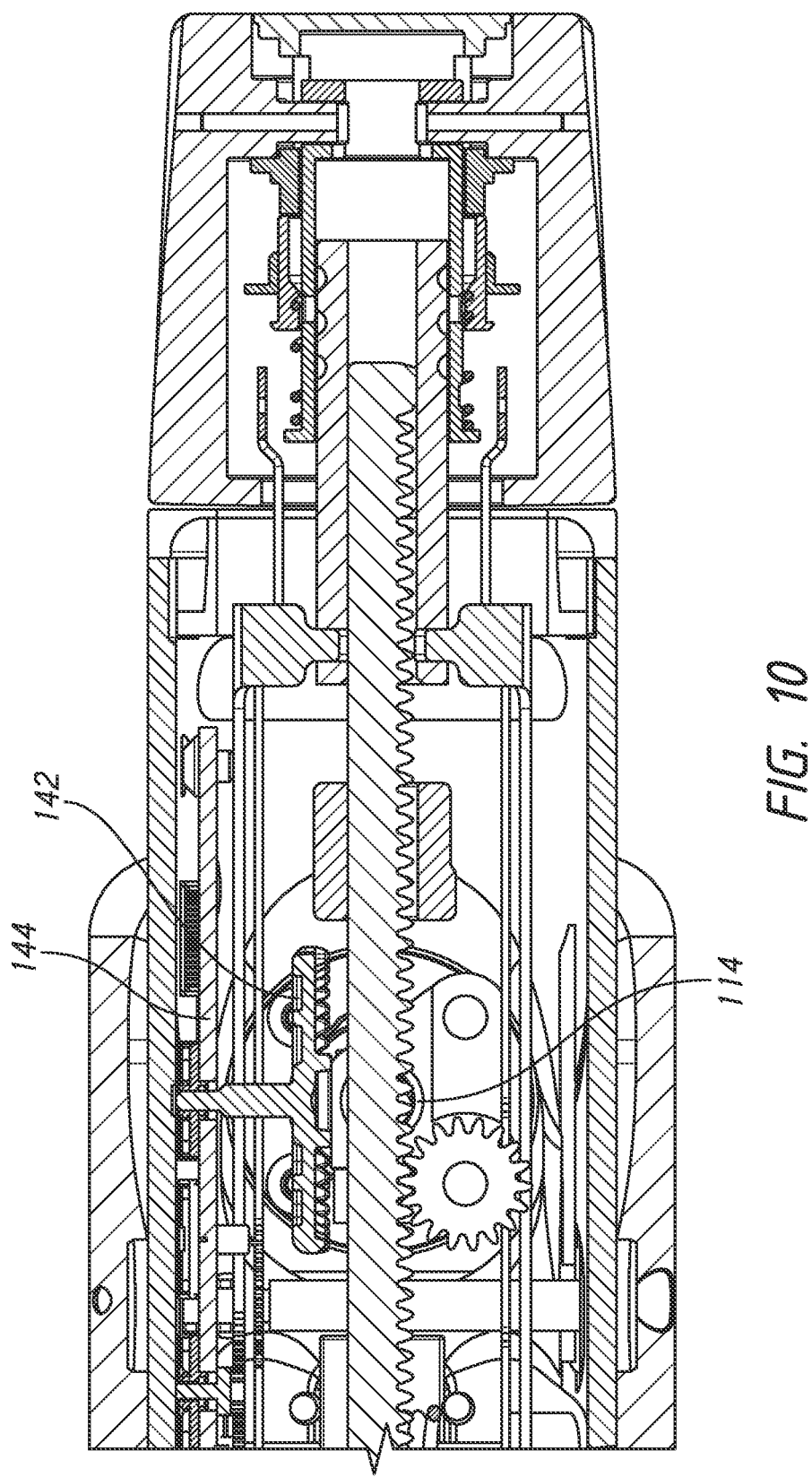
FIG. 10 is a cut-away top view of the powered handle of FIG. 2.

With reference to FIGS. 4 and 10, an embodiment of position sensor mechanism for use in the powered handle is illustrated. In operation, rotation of the motor gear 114 correspondingly rotates a crown gear 142 mounted in the handle 40. The crown gear 142 is coupled to a potentiometer such that the position of the motor gear 114 and thus the actual position of the actuation rack can be determined based on the measuring changes in resistance at the potentiometer. In some embodiments, the potentiometer can be mounted on a circuit board 144 on which the control system can be positioned. While the illustrated embodiment includes a potentiometer-based position sensor mechanism, it is contemplated that in other embodiments, other position sensing mechanisms can be used, including, for example, use of a magnetic encoder with hall effect sensors, use of limit switches that activate when the actuation shaft has traveled a predetermined distance, use of optical systems such as photodiodes to measure travel of a pattern along the actuation shaft, an optical encoder positioned on a shaft of the motor, or other position sensing systems.

Articulation Mechanism

With reference to FIGS. 11-17, an embodiment of articulation mechanism for the powered handle 40 is illustrated. In the illustrated embodiment, the handle can articulate the jaw assembly at the distal end of the shaft up to 45° in a fully articulated position in either direction relative to a longitudinally centered position. In some embodiments, the powered handle uses a manual articulation mechanism including a series of components coupled to the manually actuated articulation knob 190 at the proximal end of the handle. In other embodiments, the manually actuated articulaton knob and certain associated elements of the articulation mechanism can be positioned in other locations on the handle such as adjacent a distal end of the handle.

Figure 11:
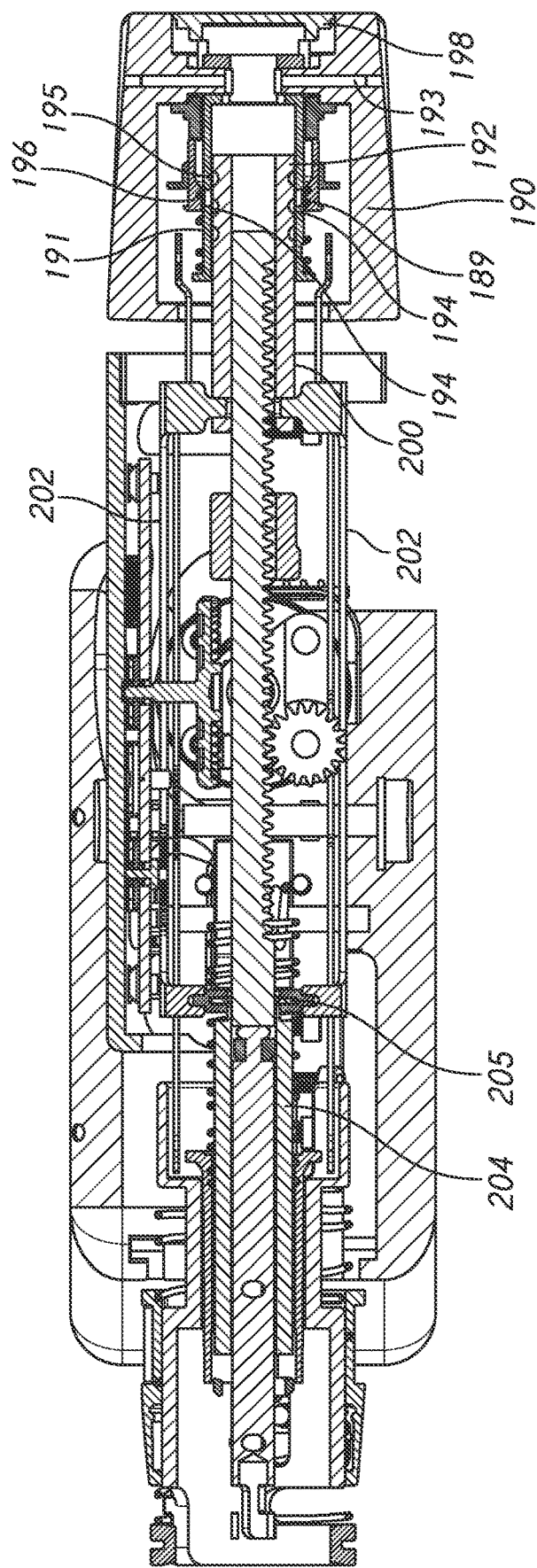
FIG. 11 is a cut-away top view of an embodiment of articulation mechanism of the powered handle of FIG. 2.
Figure 12:
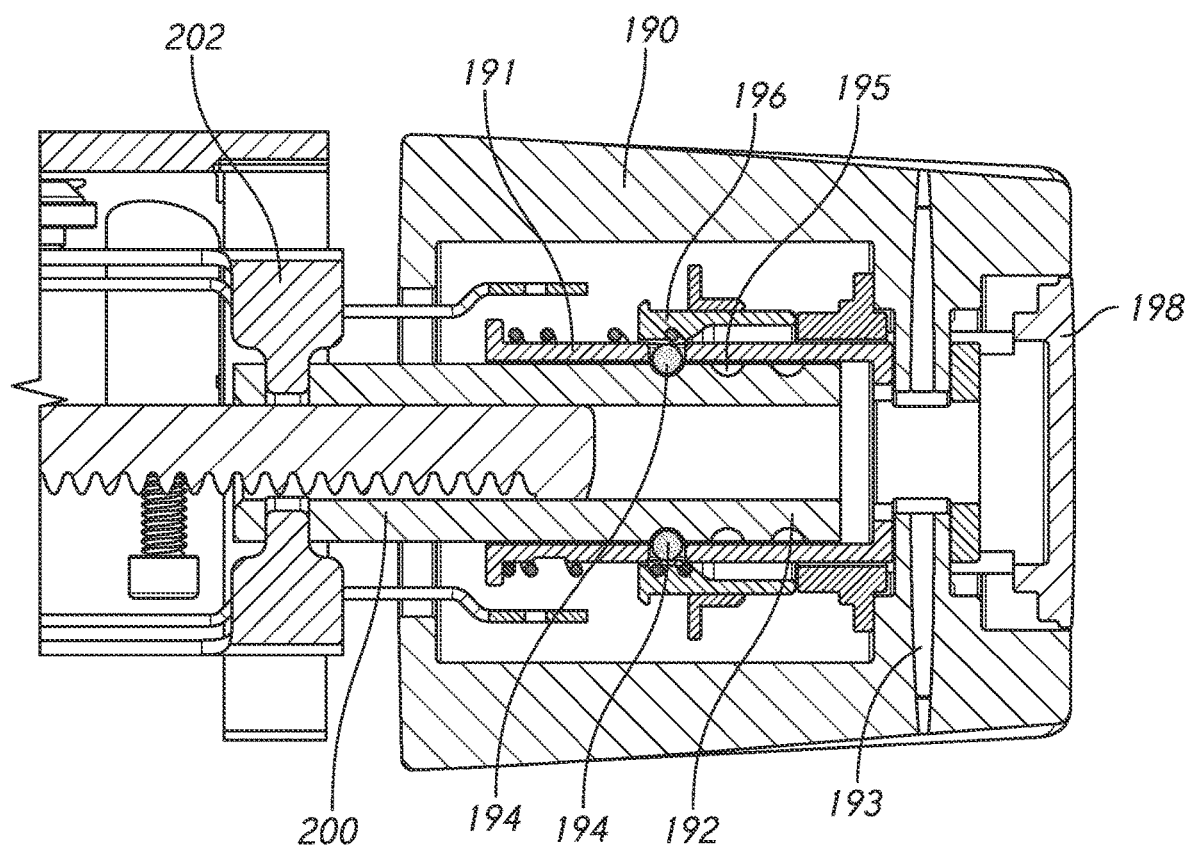
FIG. 12 is a cut-away top view of the articulation mechanism of FIG. 10 in an articulated position.

With reference to FIGS. 11 and 12, the articulation mechanism is coupled to an articulation member extending longitudinally within the reload shaft when the reload shaft is coupled to the handle. Actuation of the articulation mechanism longitudinally translates the articulation member proximally or distally relative to the shaft to articulate the jaw assembly at the distal end of the shaft.

With reference to FIG. 11, the articulation mechanism comprises a ball screw 192 having at least one helical groove or thread 195 in which one or more ball bearing 194 can ride. In the illustrated embodiment, the articulation mechanism comprises two ball bearings 194 that are engageable in two threads 195. The ball bearings 194 are positioned in ball bearing apertures 189 in a ball sleeve 191 positioned radially outwardly of the ball screw 192. The ball bearings 194 are maintained in the threads 195 by a release sleeve 196 positioned radially outward of the ball bearings 194. Rotation of the articulation knob 190, which is coupled to the ball sleeve 191 such as by connecting pins 193, rotates the ball sleeve 191 about an axis of rotation, causing the ball bearings 194 to travel within the threads 195 and correspondingly longitudinally translate the ball screw 192. Articulation of the jaw assembly is accomplished by rotating the articulation knob 190 to correspondingly rotate the ball sleeve 191 and the ball bearings 194 about the axis of rotation while their longitudinal position is fixed along the axis of rotation. The ball bearings 194, which are engaged in the threads 195 of the ball screw 192 will then translate the ball screw 192 forward and reverse along the axis of rotation. In the illustrated embodiment, the ball sleeve 191 is generally tubular, having a cavity formed therein, and a portion of the ball screw 192 is positioned within the cavity and translates longitudinally within the cavity. While the illustrated embodiment of articulation mechanism includes two ball bearings engageable threads in a ball screw, it is contemplated that in other embodiments, the articulation mechanism can have fewer or more than two ball bearings such as, for example, a single ball bearing positioned in a single helical screw or three or more ball bearings in a corresponding number of helical threads.

With reference to FIGS. 11 and 12, the ball screw 192 extends to a distal end 200 coupled to a pair of articulation links 202. The articulation links 202 are spaced apart from one another, which desirably allows them to be positioned radially outwardly of the drive system and actuation shaft within the handle. The distal ends of the articulation links 202 can be rotatably coupled to the articulation adapter 204, which can be positioned coaxially radially outwardly of the actuation adapter at the distal end of the handle. This rotational coupling can include an articulation bearing 205 having relatively low friction properties. This articulation bearing 205 can facilitate rotation of a coupled reload shaft relative to the handle assembly and longitudinal movement of the articulation adapter 204 during operation of the articulation mechanism. While the illustrated embodiment of articulation mechanism includes two articulation links laterally offset from the actuation mechanism within the handle, it is contemplated that in other embodiments, the articulation mechanism can have fewer or more than two articulation links such as, for example, an articulation link or three or more articulation links.

Figure 13:
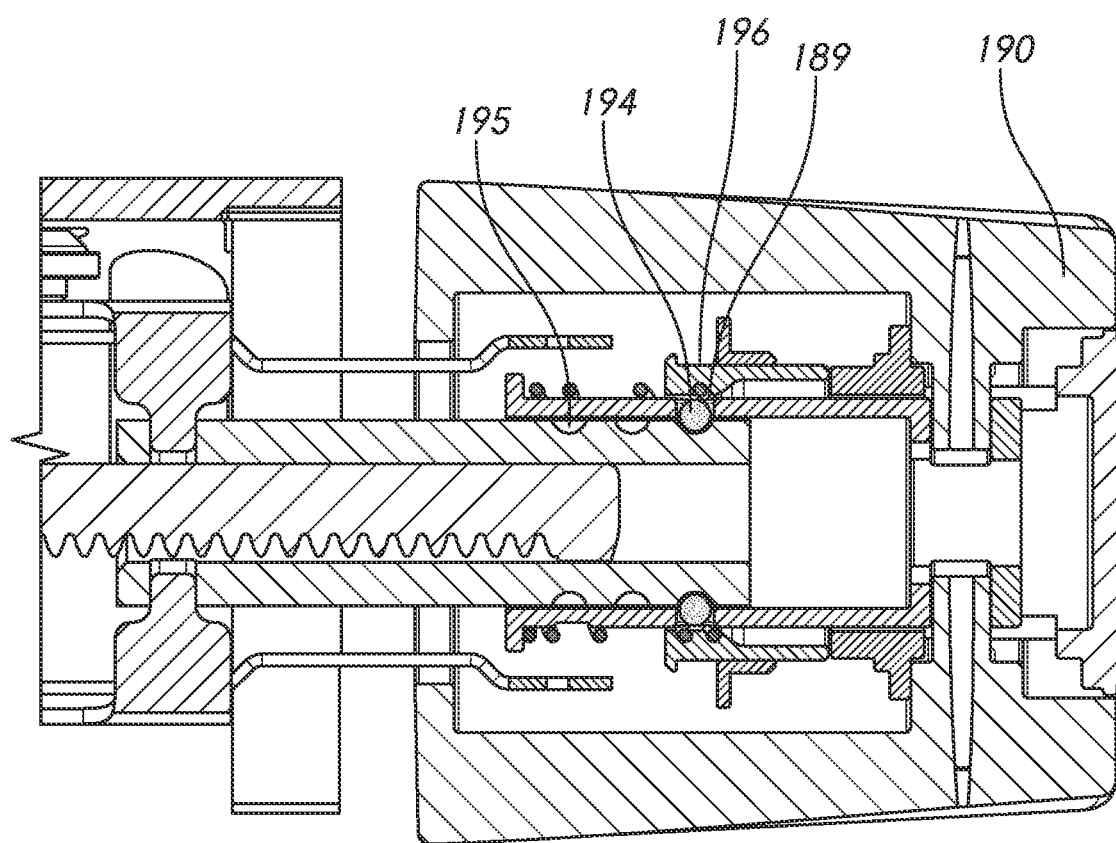
FIG. 13 is a cut-away top view of the articulation mechanism of FIG. 10 in another articulated position.

With continued reference to FIGS. 11-13, the articulation adapter 204 can be connected to the articulation member in the shaft by a bayonet connection when the shaft is coupled to the handle. The threads 195 can be configured such that moving the ball screw proximally will articulate the jaw assembly to the left when viewed from the handle relative to a longitudinally centered position and moving the ball screw 192 distally will articulate the jaw assembly to the right when viewed from the handle relative to the centered position. FIGS. 12 and 13 illustrate the articulation mechanism positioned at the fully articulated configurations defining the ends of an operational range.

Advantageously, since the helical threads 195 of the ball screw 192 are continuous, the articulation mechanism can allow the jaw assembly to be articulated to virtually infinite angular positions between a desired operational range. In some embodiments, the articulation mechanism can be configured to provide an articulation operational range from −45° to +45° of the jaw assembly relative to a longitudinally centered position defined by the longitudinal axis of the shaft. In other embodiments, the articulation mechanism can be configured to provide other operative articulation ranges including ranges providing more than +/−45° of articulation or those providing less than +/−45° of articulation. In some embodiments, the articulation mechanism can be configured to provide articulation in a single direction relative to a longitudinally centered position.

In some embodiments, the pitch of the threads 195 on the ball screw 192 is variable. For example, the threads 195 can include a relatively low pitch towards an end of the threads to advantageously provide a larger mechanical advantage when the jaw assembly can require more force to articulate. The threads 195 can include a relatively higher pitch towards a center of the threads to allow rapid movement with a relatively lower mechanical advantage where the jaw assembly can require a lower force to articulate. In other embodiments, the threads 195 include a constant pitch such that rotation of the articulation knob results in a proportional amount of articulation of a jaw assembly of the stapler that does not vary over the articulation range of the articulation mechanism. Desirably, such a constant pitch thread ball screw can result in an easily predictable response during operation of the actuation mechanism.

Figure 14:
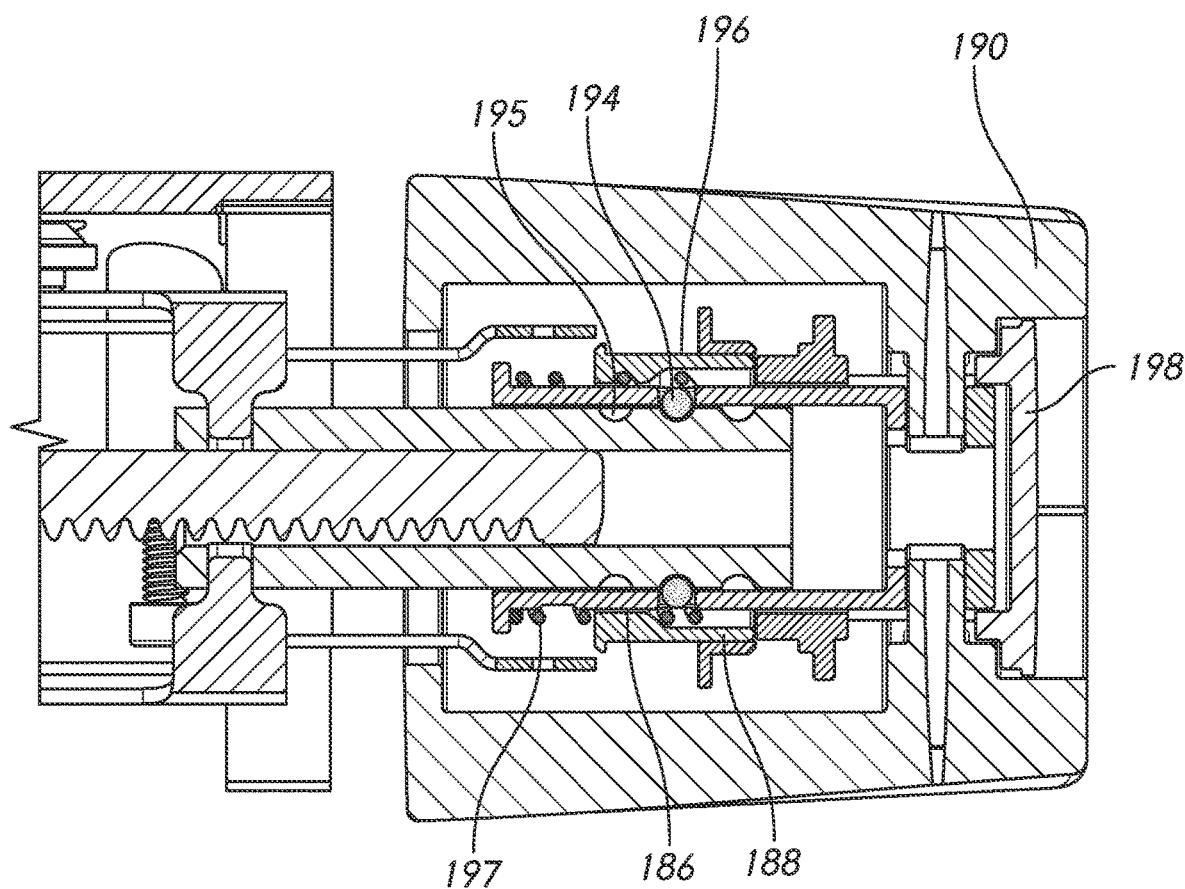
FIG. 14 is a cut-away top view of the articulation mechanism of FIG. 10 in a centered position with a release button actuated.
Figure 15:
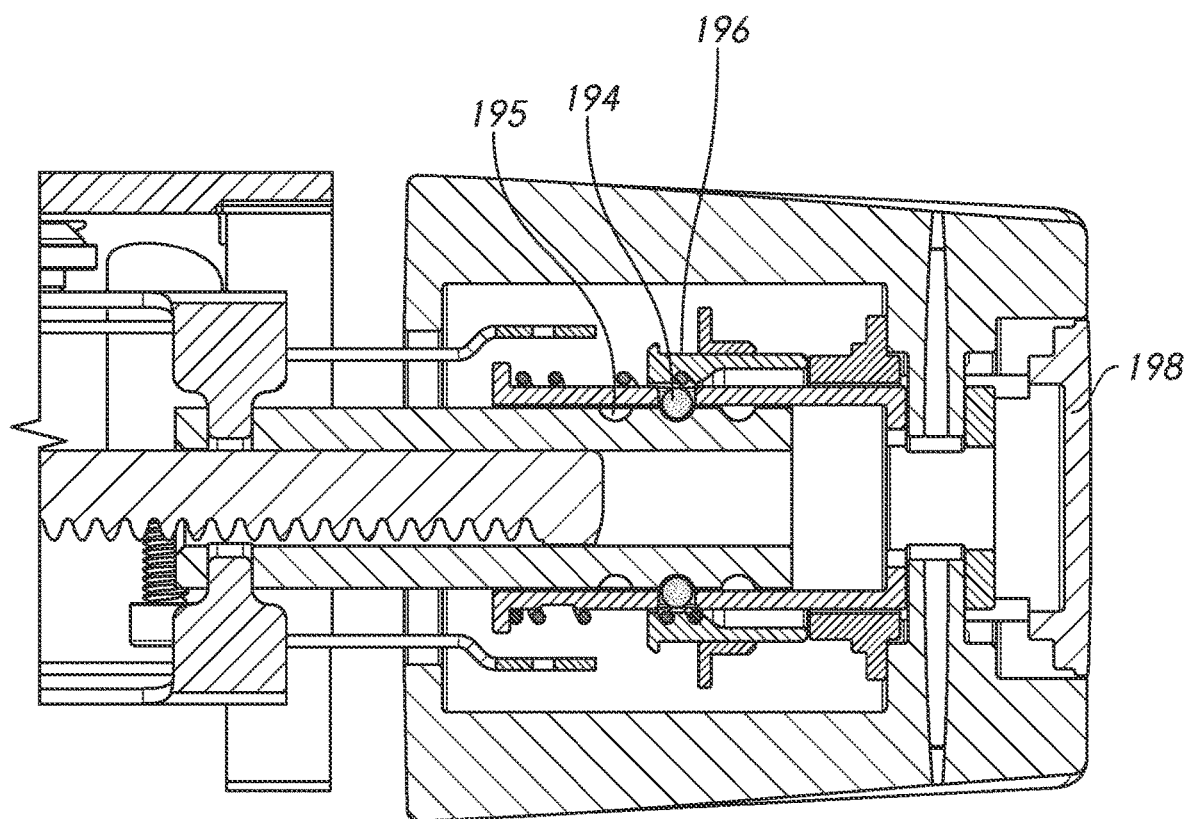
FIG. 15 is a cut-away top view of the articulation mechanism of FIG. 10 in a centered position with a release button actuated.

With reference to FIGS. 14-15, the articulation mechanism can comprise a release mechanism that allows the articulation mechanism to advantageously be reset to the longitudinally centered position from any articulated position. The release mechanism is operated by user pressing a release button 198. In the illustrated embodiment, the release button 198 is positioned radially nested within the articulation knob 190.

With reference to FIG. 14, operation of the release button 198 will distally advance the release sleeve 196. A radially inner surface of the release sleeve 196 is stepped to include an engagement surface 186 having a relatively small inner diameter and a release surface 188 having a relatively larger inner diameter with a smooth ramp between the engagement surface and the release surface. In operation, the engagement surface of the release sleeve maintains the ball bearings 194 in the threads 195 of the ball screw 192. Once the release button 198 is pushed, the engagement surface is distally advanced, allowing the ball bearings 194 to disengage from the threads 195 and advance radially outward through the ball bearing apertures 189 in the ball sleeve against the release surface.

With continued reference to FIG. 14, with the ball bearings 194 disengaged from the threads 195, the articulation mechanism can be biased to a centered position. In some embodiments, the ball screw 192 is biased to a centered position by a biasing member such as two springs and spring force from the shaft. The ball bearings 194 positioned in the centered position along the threads 195 corresponds to a longitudinally centered position of the jaw assembly.

With reference to FIG. 15, once the release button 198 is allowed to return to an undisturbed configuration, release sleeve 196 is retracted proximally by a spring. Proximal movement of the release sleeve 196 forces the ball bearings 194 into engagement with the threads 195 of the ball screw. Thus, the articulation mechanism can then be used to articulate the jaw assembly from the longitudinally centered position, or the stapler can be used with the jaw assembly in the longitudinally centered position.

With reference to FIGS. 16-17, a shaft recognition and articulation lockout mechanism 300 of certain embodiments of articulation mechanism is illustrated. The articulation mechanism can include an articulation lockout mechanism that maintains the articulation mechanism in a centered position if no instrument shaft is coupled to the handle assembly. Thus, a centered position of the articulation adapter 204 is maintained to facilitate the bayonet coupling of instrument shaft and handle assembly previously discussed above. If the articulation mechanism were maintained in an engaged configuration even when no instrument shaft were coupled to the handle assembly, it could be difficult to align the articulation member within the instrument shaft with the articulation adapter 204 in an attempt to couple the instrument shaft with the handle assembly. In the illustrated embodiment of handle assembly, the articulation lockout mechanism can be coupled with a shaft recognition mechanism.

With continued reference to FIGS. 16-17, the shaft recognition and articulation lockout mechanism comprises a lockout sleeve 302 at the distal end of the handle assembly and at least one lockout arm 304 coupled to the lockout sleeve. In the illustrated embodiment, the lockout sleeve 302 can be positioned radially outwardly of the articulation adapter 204. As illustrated, the articulation lockout mechanism comprises two lockout arms 304 extending longitudinally within the handle assembly from a proximal end coupled to the release sleeve 196 to a distal end coupled to the lockout sleeve 302. The lockout arms can be positioned laterally outwardly of the articulation links 202 and the actuation shaft 120 and other drive mechanism components. In other embodiments, one or more than two lockout arms 304 can couple the lockout sleeve 302 to the release sleeve 196, and the lockout arms 304 can be disposed in a different lateral position than in the illustrated embodiment.

In operation, when an instrument shaft is coupled to the handle assembly, the lockout sleeve 302 contacts a boss, tab, collar, or other element at the proximal end of the instrument shaft. This contact translates the lockout sleeve proximally a predetermined amount as the bayonet coupling is engaged. With no instrument shaft coupled to the handle assembly (FIG. 16), the articulation lockout mechanism and release sleeve 196 are configured such that the release sleeve 196 is positioned with the ball bearings against the release surface thereof. Thus, the articulation mechanism is in a locked out configuration. Accordingly, with no instrument shaft coupled to the handle assembly, the articulation knob may be rotated without actuating the articulation mechanism because the ball bearings are disengaged from the threads of the ball screw.

With reference to FIG. 17, once an instrument shaft is coupled to the handle assembly, the articulation lockout mechanism is moved to the engaged configuration. Engagement of the instrument shaft with the lockout sleeve proximally translates the lockout sleeve 302 and lockout arms 304 coupled thereto. The proximal ends of the lockout arms 304 are coupled to the release sleeve 196 of the articulation mechanism such that the proximal movement of the lockout arms 304 advances the release sleeve 196 proximally to engage the ball bearings with the threads of the ball screw. Thus, with an instrument shaft attached, rotation of the articulation knob results in translation of the articulation adapter to articulate an end effector coupled to the instrument shaft.

Figure 18:
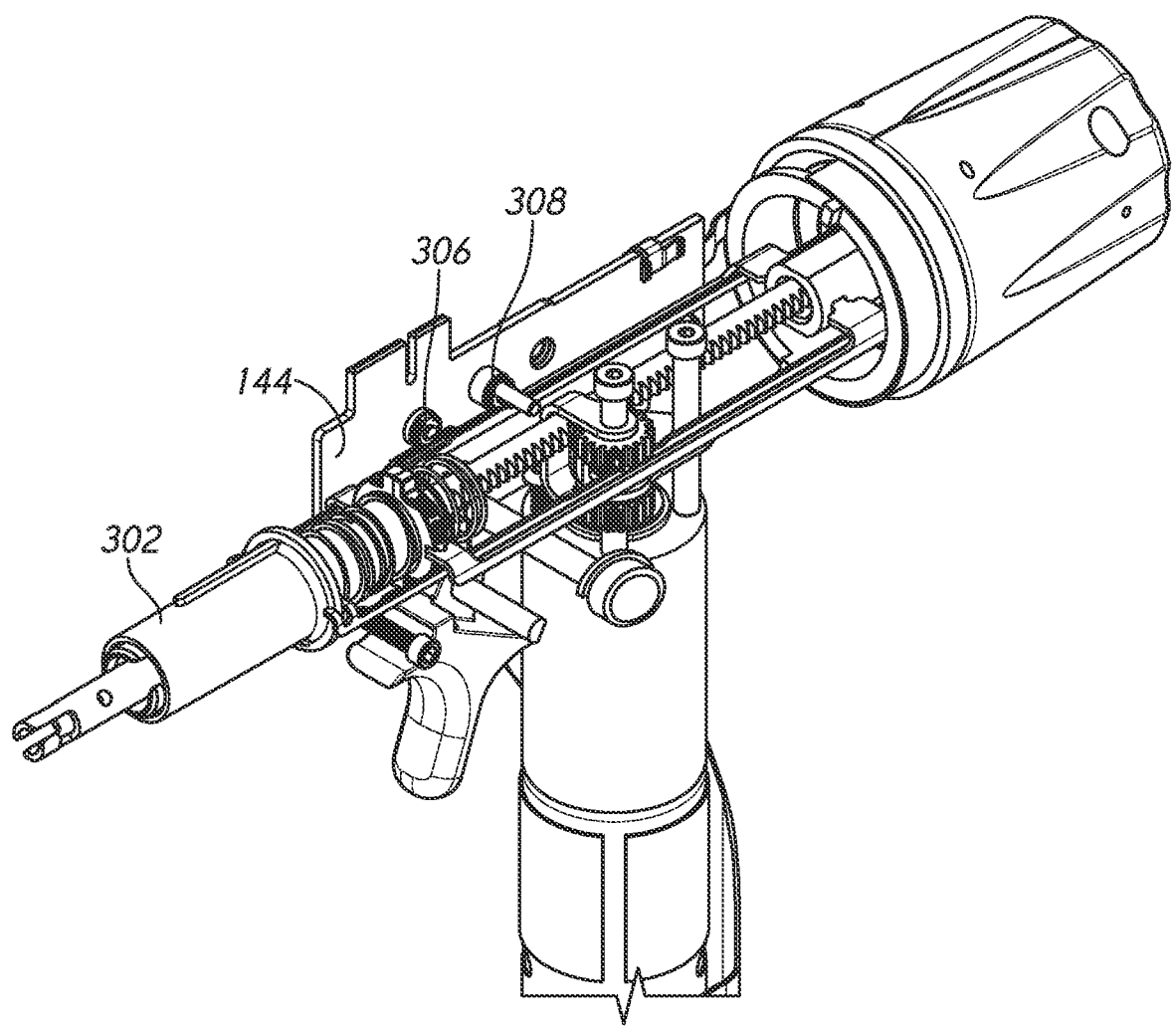
FIG. 18 is a perspective view of the drive system and articulation mechanism of the powered handle of FIG. 2.

With reference to FIGS. 18 and 19, the articulation mechanism and shaft recognition/articulation lockout mechanism can each comprise a sensor 306, 308 to identify a position of the respective mechanism. In the illustrated embodiment, the sensor of the articulation mechanism comprises a potentiometer in geared engagement with a toothed rack formed on one articulation link 202, and the sensor of the shaft recognition/articulation lockout mechanism can comprise a potentiometer in geared engagement with one lockout arm 304. In some embodiments, the sensors of the articulation mechanism and shaft recognition/articulation latch mechanism can each be mounted on the circuit board 144 on which the control system can be positioned. Thus, one or both of the articulation position and shaft recognition position data can be incorporated by the control system to revise a motor drive profile during an open/close, firing, and return operation of the powered handle. For example, the articulation position can be incorporated by the control system to apply a correction value to a measured actuator rack and actuator position such that certain operational states of the motor can be controlled based on a corrected position of the actuator accounting for a given measured articulation. While the illustrated embodiment includes a potentiometer-based position sensor mechanism, it is contemplated that in other embodiments, other position sensing mechanisms can be used.

Shaft Recognition Mechanism

In certain embodiments, the powered handle can be configured for use with three reload shafts, each having different jaw lengths. For example, the powered handle can be configured for use with reload shafts having a jaw length of approximately 30 mm, 45 mm, and 60 mm. The powered handle can be configured to operate with any of the reload shafts having a predetermined jaw length, and reload shafts can be used and replaced throughout the intended lifespan of the device. As the actuation shaft of the powered handle can pass through different longitudinal positions during grasping and firing operations for reload shafts with different jaw lengths, each of these jaw lengths can have a corresponding operational profile in a control system for the powered handle, as further discussed with reference to FIGS. 45-46. Accordingly, it is desirable that the powered handle includes a shaft recognition mechanism to detect if a reload shaft being connected to the powered handle has a predetermined jaw length, if an unrecognized shaft is connected, or if no shaft is connected. Upon recognition of a reload shaft having a particular jaw length, the control system can operate the powered handle with the corresponding operational profile. While as discussed above, in certain embodiments, the shaft recognition mechanism can be configured to distinguish among reload shafts having jaw lengths of 30 mm, 45 mm, and 60 mm, it is contemplated that in other embodiments, the shaft recognition mechanism can be configured to distinguish among more or fewer than three jaw lengths and among reload shafts having various other jaw lengths. Moreover, it is contemplated that in other embodiments the shaft recognition mechanism can be configured to distinguish among other attributes of a shaft such as a jaw geometry (for example, laparoscopic linear, curved, or circular), among various versions of a reload shaft (for example if shaft mechanisms, hardware components, materials, and/or geometry are revised during development of different versions of a reload shaft), or among other attributes of a shaft for which it can be desirable to provide a corresponding operational profile.

In certain embodiments, the powered handle is connected to a reload shaft via mechanical components in the coupler 46 (FIGS. 1-2). A control system within the powered handle, further discussed with reference to FIGS. 45-46, interprets this connection process through position readings from the internal shaft recognition sensor 306 (FIG. 19). In certain embodiments, the shaft recognition sensor 306 comprises a potentiometer. In certain embodiments, the control system is configured such that each time the device is powered on, the control system enters a shaft recognition state to determine if a reload shaft is inserted. A shaft may be inserted before power is supplied to the device, but may only be considered authenticated as recognized once the no shaft position is first reached. The control system can be configured to disable operation of the powered handle until a reload shaft is authenticated as "recognized". If the system is unable to authenticate a shaft properly, it shall enter an "unrecognized shaft" state.

Once the powered handle is deemed ready for use by the control system, and an inserted reload shaft has been authenticated as "recognized" by the shaft recognition mechanism, the control system is then able to determine and allocate the position values for full travel of the actuation shaft, which actuates the jaw assembly for grasping, transection of tissue, and staple formation. As users are able to interchange shafts, and damage to this system is possible during a procedure, the shaft recognition mechanism and associated aspects of the control system run continual checks throughout a lifespan of the device.

Advantageously, this shaft recognition mechanism and associated aspects of the control system facilitate reliable staple firing for reload shafts having various jaw geometries. Interpreting a false recognized shaft connection could result in device damage, as misinterpreting a shaft jaw assembly length may undesirably result in unformed or malformed staples or damage to the jaw assembly.

Figure 19A:
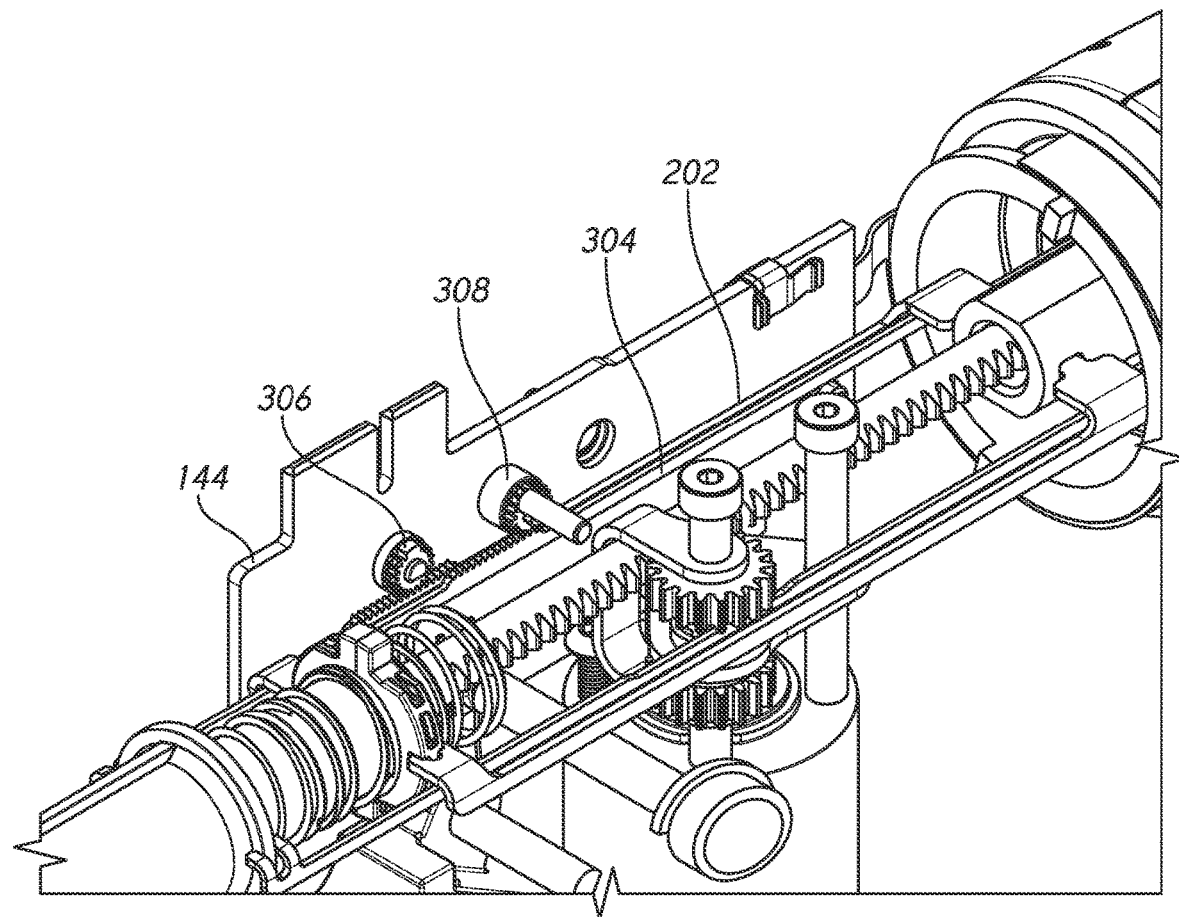
FIG. 19A is a perspective view of the articulation links and lockout links of the articulation mechanism of the powered handle of FIG. 2.
Figure 19C:
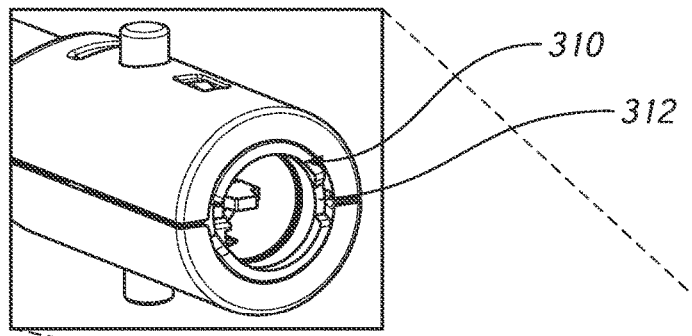
FIG. 19C is a perspective end view of a proximal end of the reload shaft of FIG. 19B.
Figure 19B:
FIG. 19B is a side view of an embodiment of reload shaft for the surgical stapling system of FIG. 1.

With reference to FIGS. 19B and 19C, an embodiment of reload shaft for use with a shaft recognition mechanism are illustrated. FIG. 19B illustrates a side view of the reload shaft 20 having a proximal end 22 configured to couple to the coupler 46 of the handle assembly. (FIGS. 1-2). FIG. 19C is a detail perspective view of the proximal end 22 of the reload shaft 20 having a lockout keyway 310 therein. The lockout keyway 310 comprises at least one identification notch 312 formed therein that facilitates recognition of the shaft jaw assembly by the shaft recognition mechanism.

Figure 19D:
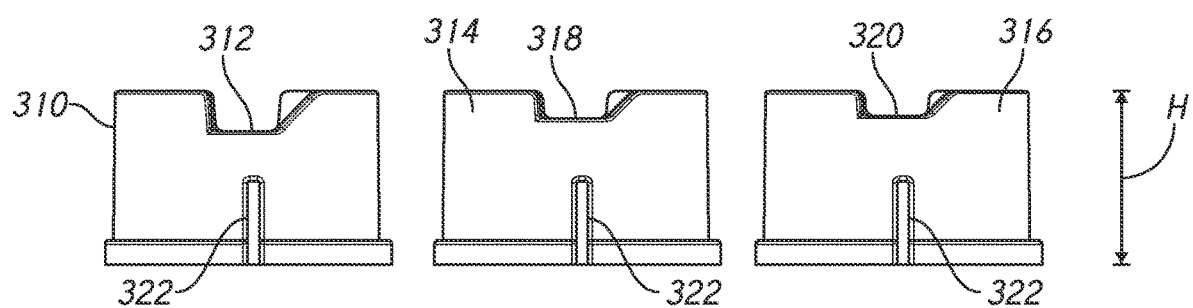
FIG. 19D is a side view of certain embodiments of lockout keyway for a reload shaft of FIG. 19B.

With reference to FIG. 19D, exemplary embodiments of three lockout keyways 310, 314, 316 are illustrated. The illustrated lockout keyways 310, 314, 316 each have the same total height H to a proximal edge, but each have a unique depth of identification notch 312, 318, 320. Each of the lockout keyways comprises a ramped edge extending between the proximal edge and at least one side of the identification notch 312, 318, 320. Each of the lockout keyways further comprise a key, such as a rib 322 to restrict rotation of the lockout keyway relative to the reload shaft as the reload shaft is coupled with the handle assembly.

Figure 19E:
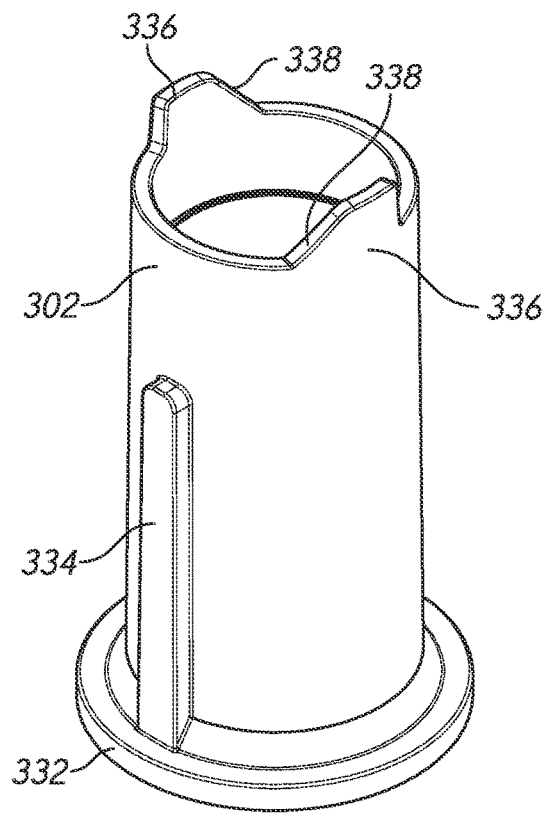
FIG. 19E is perspective view of a lockout sleeve of the powered handle of FIG. 2.

With reference to FIG. 19E, an exemplary lockout sleeve 302 of the shaft recognition mechanism of the powered handle is illustrated. In the illustrated embodiment, the lockout sleeve 302 comprises an engagement feature such as a flange 332 at a proximal end and at least one rib 334 or other key element protruding from the outer surface thereof to maintain an orientation of the lockout sleeve 302 relative to a longitudinal axis of the actuation shaft. As illustrated, the lockout sleeve 302 further comprises at least one mating protrusion such as a tooth 336 extending distally from the distal end thereof positioned to engage a corresponding notch of a lockout keyway of a connected reload shaft. The at least one tooth 336 can have a ramped edge 338 such that it can matingly engage an identification notch of a lockout keyway that likewise has a ramped edge. In the illustrated embodiment, the lockout sleeve 302 comprises two teeth 336 positioned diametrically opposed on a distal end of the lockout sleeve 302 to engage a corresponding two identification notches. In other embodiments, it is contemplated that the number and locations of mating features included the lockout keyways and lockout sleeves for a shaft recognition mechanism can be varied.

Figure 19F:
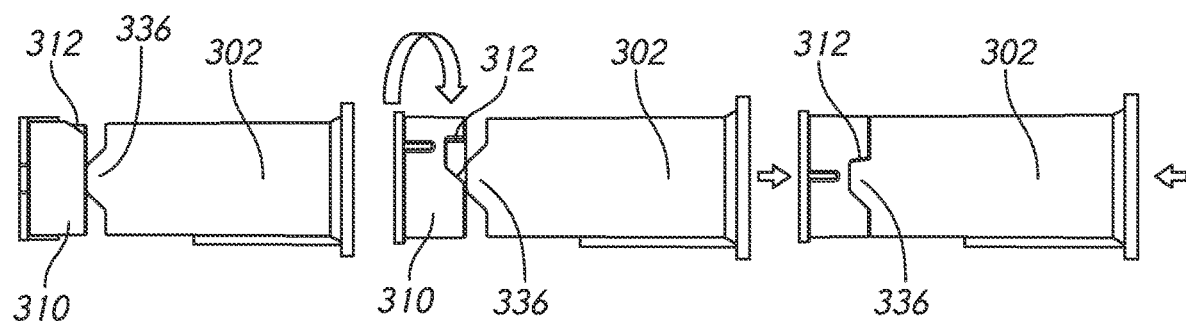
FIG. 19F is schematic illustrating a coupling operation of an embodiment of lockout keyway of a reload shaft with a lockout sleeve of a powered handle.

With reference to FIG. 19F, an exemplary sequence of interaction between a lockout sleeve 302 and a lockout keyway 310 is illustrated as a shaft is installed on a powered handle. As illustrated, the shaft installation sequence proceeds from left to right. In the left panel, as the shaft is positioned in the coupler 46 (FIG. 1) of the handle assembly, the lockout sleeve 302 is oriented such that the teeth 336 are misaligned with the identification notches 312. The coupler 46 and shaft engage in a bayonet connection in which the shaft is advanced longitudinally proximally relative to the handle, then rotated relative to the longitudinal axis. The center panel illustrates the proximal longitudinal movement longitudinally proximally displacing the lockout sleeve 302 relative to the handle as the rotational movement of the shaft moves the teeth 336 closer to alignment with the identification notches 312. The right panel illustrates completion of rotation of the shaft relative to the handle assembly to secure the bayonet coupling. As illustrated, once the shaft is coupled to the handle assembly, the teeth 336 of the lockout sleeve 302 engage and are positioned within the identification notches 312 of the lockout keyway 310. Thus, during a coupling operation, the lockout sleeve 302 is initially displaced proximally by installation of the shaft with the teeth misaligned with the identification notches, then returns distally as the teeth 336 engage the identification notches.

Figure 19G:
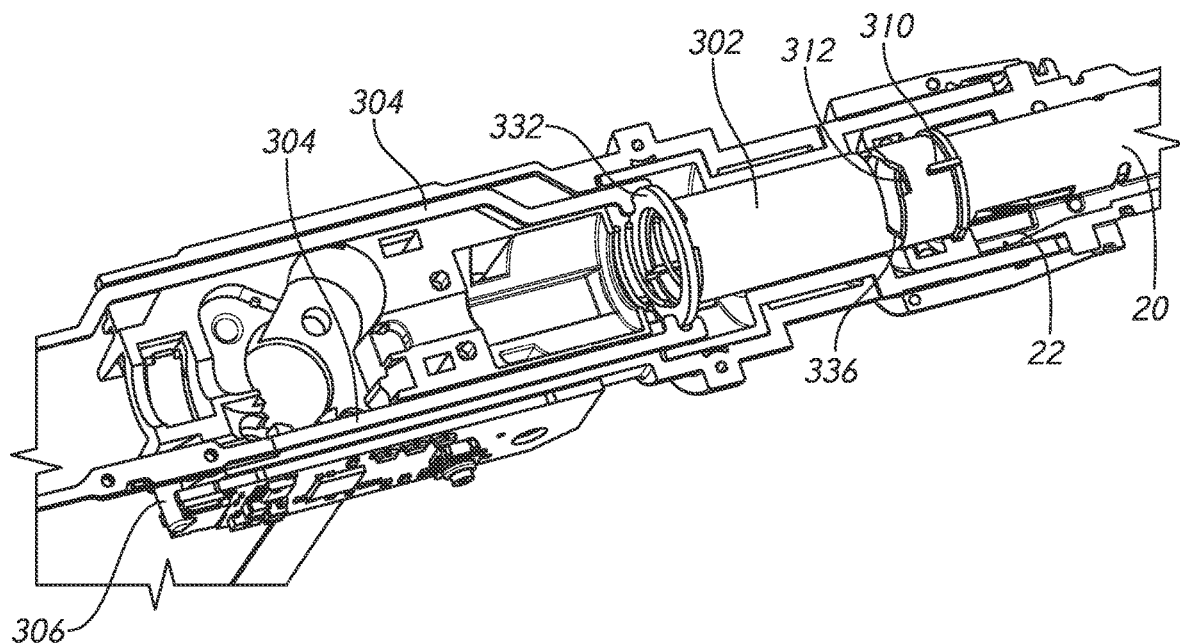
FIG. 19G is a cut away perspective view of a powered handle and a reload shaft with the reload shaft advanced proximally in a coupling operation.
Figure 19H:
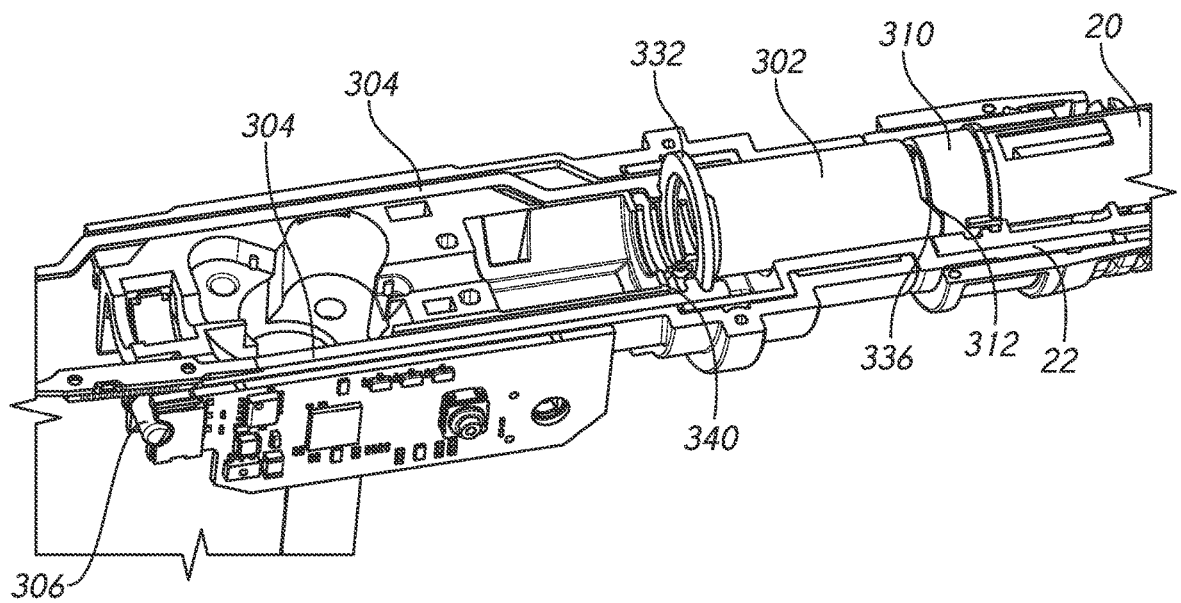
FIG. 19H is a cut away perspective view a powered handle and a reload shaft with the reload shaft coupled to the powered handle.

With reference to FIGS. 19G-19H, an exemplary sequence of interaction between a lockout sleeve 302 and a lockout keyway 310 is illustrated as a shaft 20 is installed on a powered handle. In FIG. 19G, the proximal end 22 of the shaft is seated in the coupler 46 of the handle and advanced proximally such that the teeth 336 on the lockout sleeve 302 are misaligned with the identification notch 312 of the lockout keyway 310. In FIG. 19H, as the bayonet coupling is made, the shaft 20 and lockout keyway 310 are rotated about the longitudinal axis of the shaft such that the teeth 336 of the lockout sleeve 302 nest in the identification notch 312 of the lockout keyway 310. In the illustrated embodiment, the lockout sleeve 302 is biased distally by a spring 340 to maintain this engagement of the teeth 336 with the identification notch 312. The lockout sleeve 302 is coupled to at least one lockout link 304 at the flange 332 of the lockout sleeve. A rack positioned on one of the lockout links 304 engages a pinion of the shaft recognition sensor 306. In certain embodiments, the shaft recognition sensor comprises a potentiometer. Accordingly, as the shaft is coupled to the handle assembly, the potentiometer is positioned in a first position corresponding to the initial proximal movement of the lockout links, and then, as the shaft is rotated in the bayonet coupling, the potentiometer is positioned in a second position corresponding to a mated engagement of the teeth 336 of the lockout sleeve with the identification notch 312 of the lockout keyway 310. The depth of the identification notch thus determines the second position of the potentiometer.

Figure 19I:
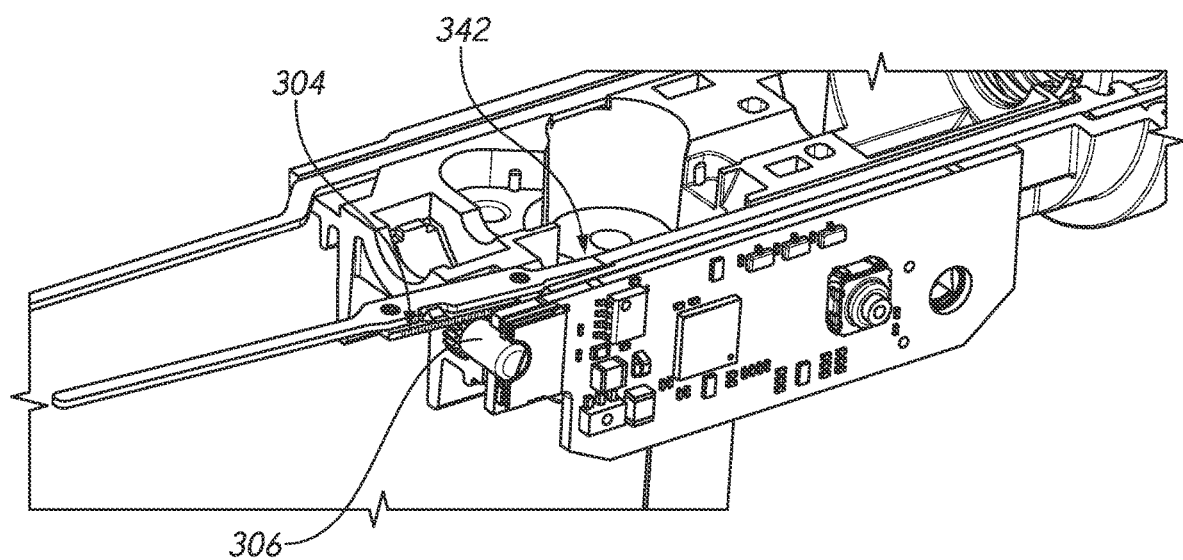
FIG. 19I is a cut away perspective view of the lockout links of the articulation and shaft recognition mechanisms of the powered handle of FIG. 2.

With reference to FIG. 19I, in certain embodiments, the lockout link 304, including a rack to engage the shaft recognition sensor 306, can comprise a bend 342 therein. Desirably, the bend 342 can enhance meshed engagement of the rack of the lockout link 304 with a corresponding pinion of the shaft recognition sensor 306, by reducing gear lash.

Figure 19J:
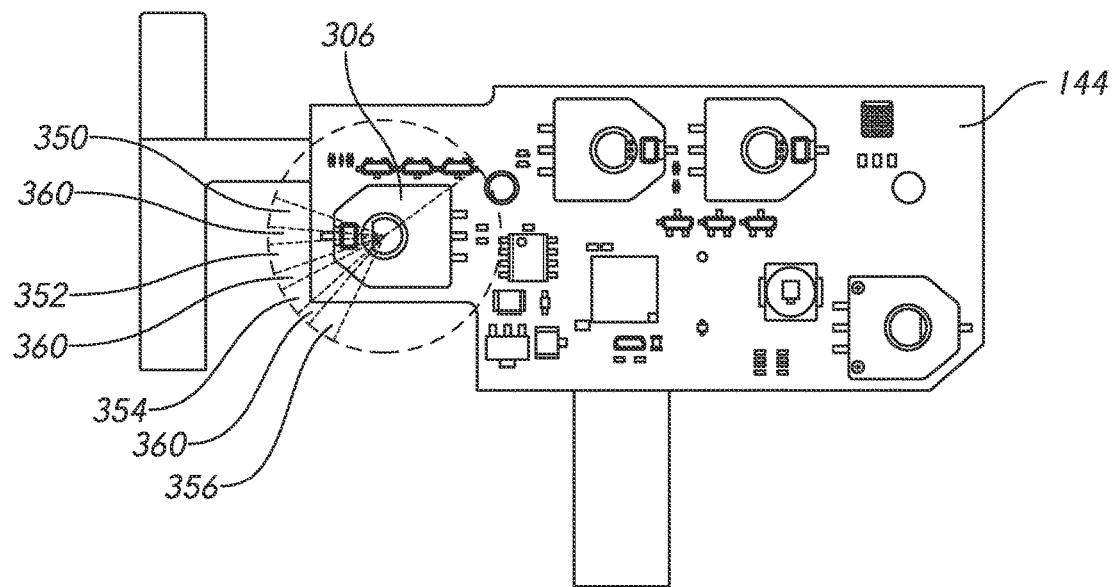
FIG. 19J is a side view of an embodiment of circuit board including a shaft recognition sensor for a shaft recognition mechanism of the powered handle of FIG. 2.
Figure 19K:
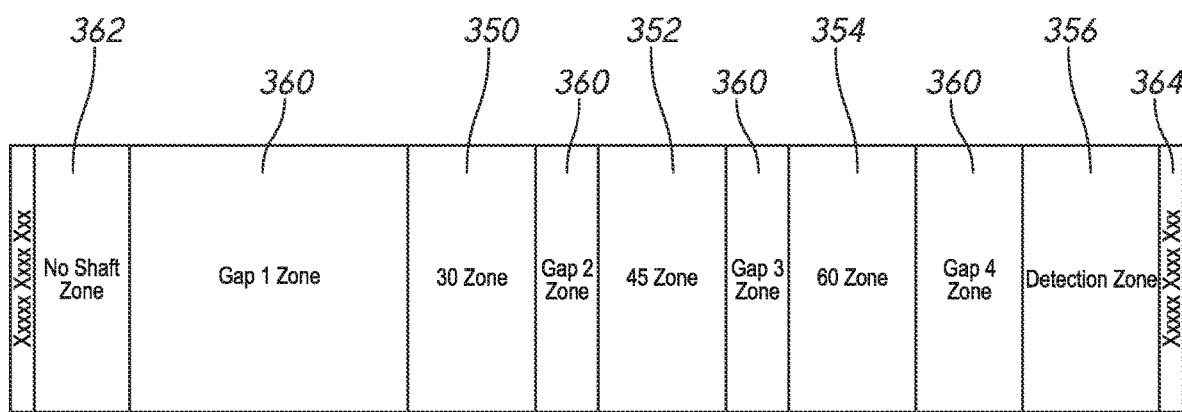
FIG. 19K is an exemplary distribution of shaft recognition zones for a shaft recognition sensor of FIG. 19J.

With reference to FIGS. 19J and 19K, in certain embodiments, a powered handle system can be configured for use with different reload shaft assemblies having corresponding different grasping and or firing characteristics. For example, the powered handle system can be configured for use with three reload shaft assemblies each having a different jaw assembly length. In these embodiments, the shaft recognition mechanism can be configured to position the shaft recognition sensor 306 in three distinct position ranges to recognize that a reload shaft is present and that it is a shaft recognizable by the control system of the powered handle assembly. FIG. 19J schematically illustrates a shaft recognition sensor 306 on a printed circuit board 144 of a powered stapler handle with angular position ranges for certain recognition zones identified.

With continued reference to FIGS. 19J and 19K, in certain embodiments the shaft recognition sensor 306 comprises a potentiometer including a variable resistor that can correlate voltage with angular displacement of an input member. In certain embodiments, the potentiometer can have approximately a 330 degree angular operating window and a 30 degree dead zone. In certain embodiments, the control system of the powered handle can comprise a shaft recognition module that assigns state criteria to a plurality of subdivided ranges within the operating window of the potentiometer, each of the subdivided ranges representing positioning of the potentiometer by the shaft recognition mechanism. In certain embodiments, the shaft recognition module can be configured to distinguish among positioning of the potentiometer in at least a shaft detection zone and a plurality of recognition zones, each zone corresponding to coupling of a recognizable reload shaft with the handle assembly. In other embodiments, the shaft recognition module can be configured to distinguish among shaft types, shaft versions, or another shaft attribute for which it is desirable to have corresponding operational profiles. The shaft recognition module can further be configured to distinguish a no shaft zone indicating no reload shaft coupled with a powered handle, and a plurality of gap zones between the shaft recognition zones to enhance accuracy in recognition of a recognizable reload shaft and identify misalignments in coupling reload shafts.

In use, the shaft recognition module in the control system can be configured, upon detection of the shaft recognition potentiometer in the detection zone, to monitor for positioning of one of the potentiometer in the no shaft zone (indicating decoupling of the reload shaft from the powered handle) or in one of the recognition zones (indicating coupling with a recognizable reload shaft) within a first predetermined time. When the shaft recognition mechanism has positioned the potentiometer in a recognition zone, the shaft recognition module can monitor the position of the potentiometer for departure from the recognized recognition zone for a second predetermined time longer than the first predetermined time to allow for further operational tolerance during use of the stapling system. If the shaft recognition module detects that the potentiometer is in a position corresponding to a predefined gap between recognition zones or between a recognition zone and the detection zone, if the position of the potentiometer is not moved from the gap within a third predetermined time, the shaft recognition module configures the control system in a shaft unrecognized state, which disables the handle and can trigger a user alarm or alert as further discussed with respect to the light ring user indicia discussed with reference to FIGS. 42-44.

The shaft recognition mechanism can be configured to position the potentiometer in one of three discrete recognition zones 350, 352, 354 when a reload shaft recognizable by the shaft recognition mechanism is coupled to the powered handle. As discussed above with reference to FIGS. 19G and 19H, as a recognizable reload shaft is installed, the shaft recognition mechanism is further configured to position the potentiometer in a shaft detection zone 356 corresponding to an initial proximal translation of the lockout sleeve 302 before the potentiometer is positioned in a recognition zone 350, 352, 354. The gaps 360 between the recognition zones can enhance operation of the shaft recognition mechanism and shaft recognition module.

With reference to FIG. 19K a schematic view of one embodiment of an arrangement of the various zones recognizable by a shaft recognition module of the control system is illustrated. In the illustrated schematic, the shaft recognition module further comprises a no shaft zone 362. The lockout sleeve can be biased to position the shaft recognition mechanism with the potentiometer in the no shaft zone when no shaft is connected to the handle assembly. In certain embodiments, when a handle assembly is initially powered on, the shaft recognition module can report a shaft unrecognized state if the potentiometer is not in the no shaft zone 362. Moreover, upon decoupling and removal of a reload shaft from the handle assembly, the shaft recognition module verifies that the potentiometer has entered the shaft detection zone 356 followed by entering the no shaft zone 362 for a predetermined time. Additionally, the arrangement of zones in the shaft recognition module can further comprise a maximum extension zone beyond the shaft detection zone. If the potentiometer is advanced to the maximum extension zone, the shaft recognition module can report an alert or error state to the control system as it may indicate a hardware fault with the shaft recognition mechanism or the attempted coupling of a nonrecognizable reload shaft.

With reference to FIG. 19K, desirably, in the illustrated arrangement of recognition zones, the position of the shaft detection zone and recognition zones within the shaft recognition design are ordered from shortest jaw assembly length to longest jaw assembly length adjacent the shaft detection zone such that the shaft recognition module is unlikely to misinterpret a longer length shaft for a shorter one. Thus, as illustrated the shaft recognition mechanism and shaft recognition module are configured to reduce a risk of an incomplete firing operation for a reload shaft having a relatively long jaw assembly.

Manual Override Return System

With reference to FIGS. 20-27 an embodiment of manual return mechanism for the powered handle is illustrated. A manual return mechanism can advantageously provide a redundant return mechanism in the event of a power supply failure, other powered component failure, or mechanical failure or binding.

Figure 20:
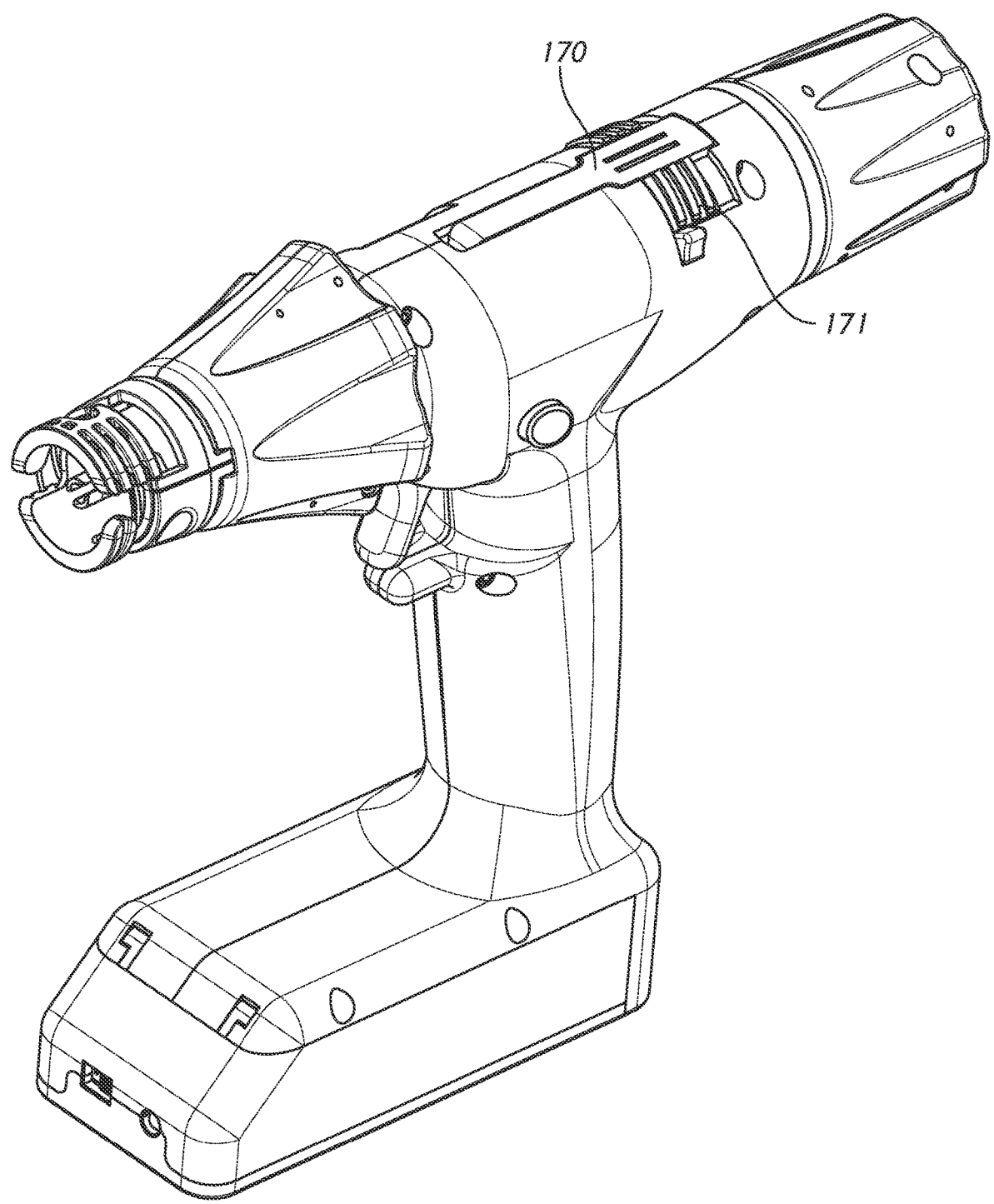
FIG. 20 is a perspective view of the powered handle of FIG. 2 with an override return mechanism in a disengaged configuration.

With reference to FIGS. 20-25, the manual return mechanism includes three separate, independently operable subassemblies that are operated in sequence to return the actuation shaft 120 to a proximal-most position within the handle, which corresponds to the open configuration of the jaw assembly. As illustrated, the manual return mechanism 170 comprises a return lock mechanism, a shaft rotation mechanism, and a shaft retraction mechanism. FIG. 20 illustrates the powered handle in a powered operation mode, with the return lock mechanism in a locked configuration. In operation, when it is desirable to manually return the stapler to the open configuration, the return lock mechanism is initially actuated to unlock the manual return mechanism.

Figure 21:
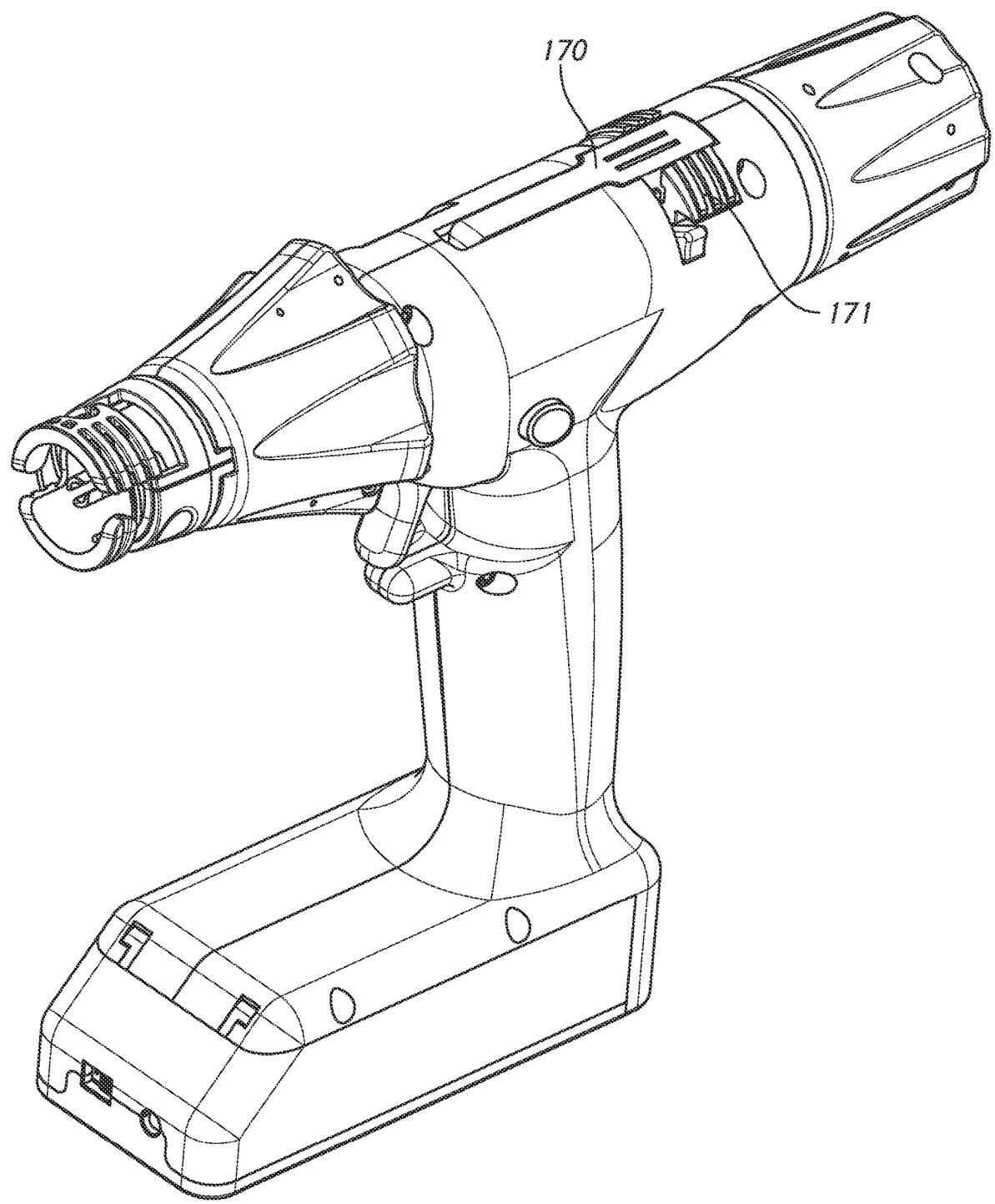
FIG. 21 is a perspective view of the powered handle of FIG. 2 with the override return mechanism unlocked for movement to a return configuration.
Figure 22:
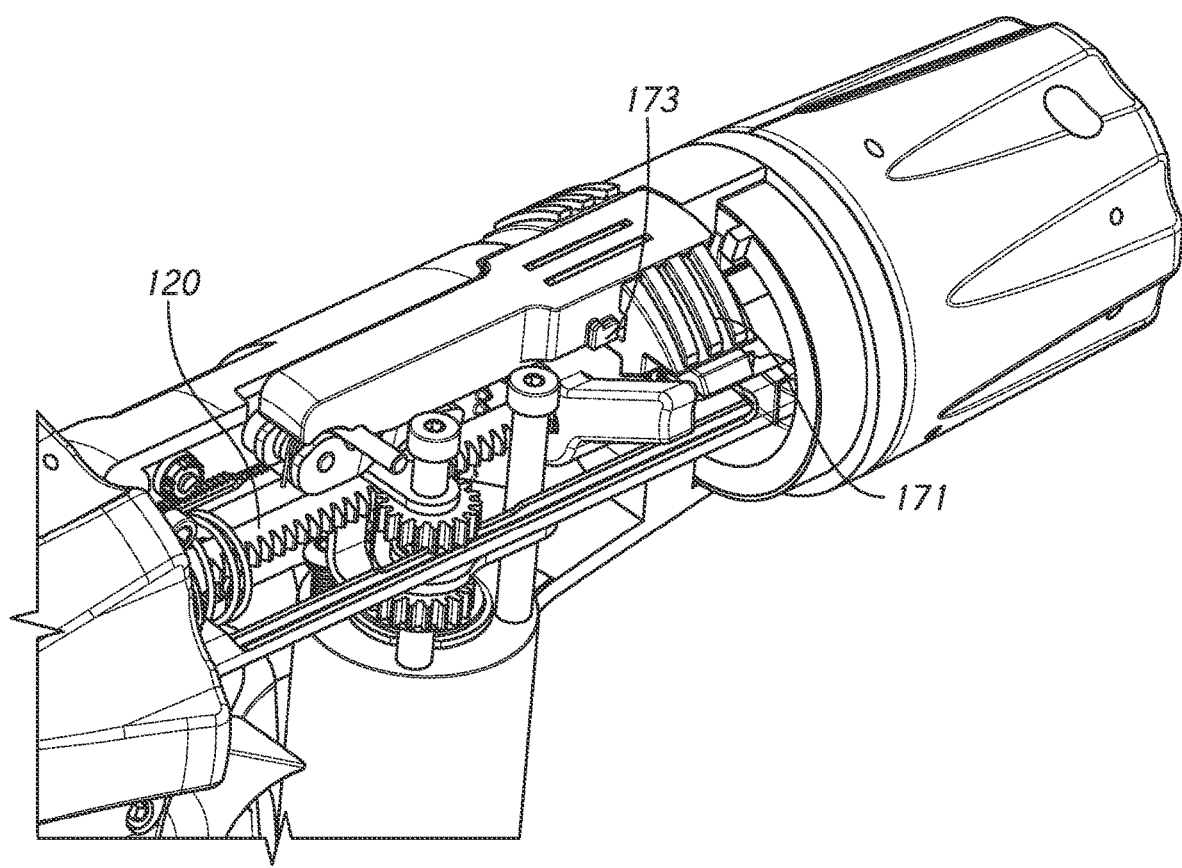
FIG. 22 is a perspective partial cut-away view of the powered handle of FIG. 2 with the override return mechanism unlocked for movement to a return configuration.

As illustrated in FIGS. 21-22, to actuate the return lock mechanism, a return lock 171 is initially slid proximally with respect to the housing of the handle assembly. This movement of the return lock 171 unlocks the shaft rotation mechanism and the shaft retraction mechanism. In the illustrated embodiment, the return lock 171 is moved off of a position in which it interfered with movement of the shaft rotation mechanism, exposing the shaft rotation mechanism for use. Simultaneously, the return lock 171 is disengaged from lock protrusions 173 or tabs on the shaft retraction mechanism allowing the shaft retraction mechanism to pivot away from the handle assembly. A lever of the shaft retraction mechanism can be biased away from the handle assembly, causing it to pivot away from the handle assembly when the return lock is slid proximally.

Figure 23:
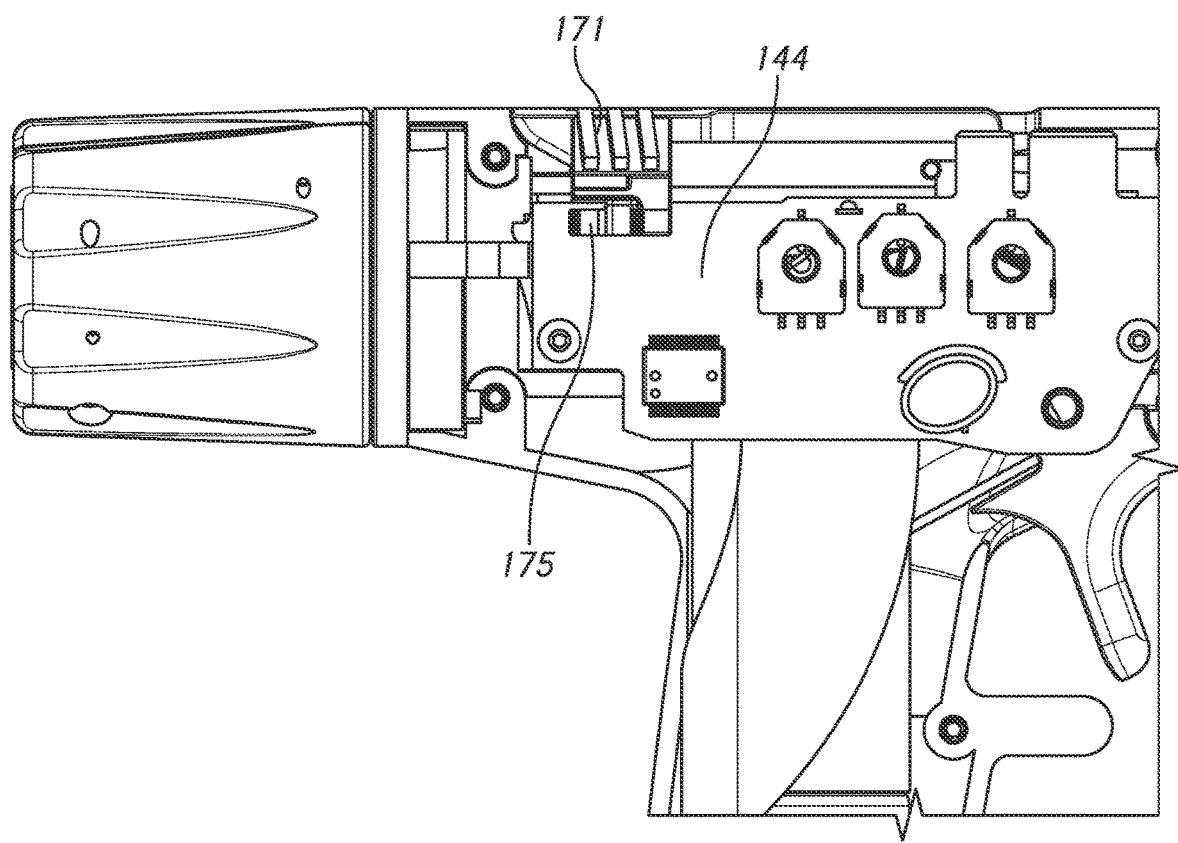
FIG. 23 is a partial cut-away side view of the powered handle of FIG. 2 with the override return mechanism in a disengaged configuration.
Figure 24:
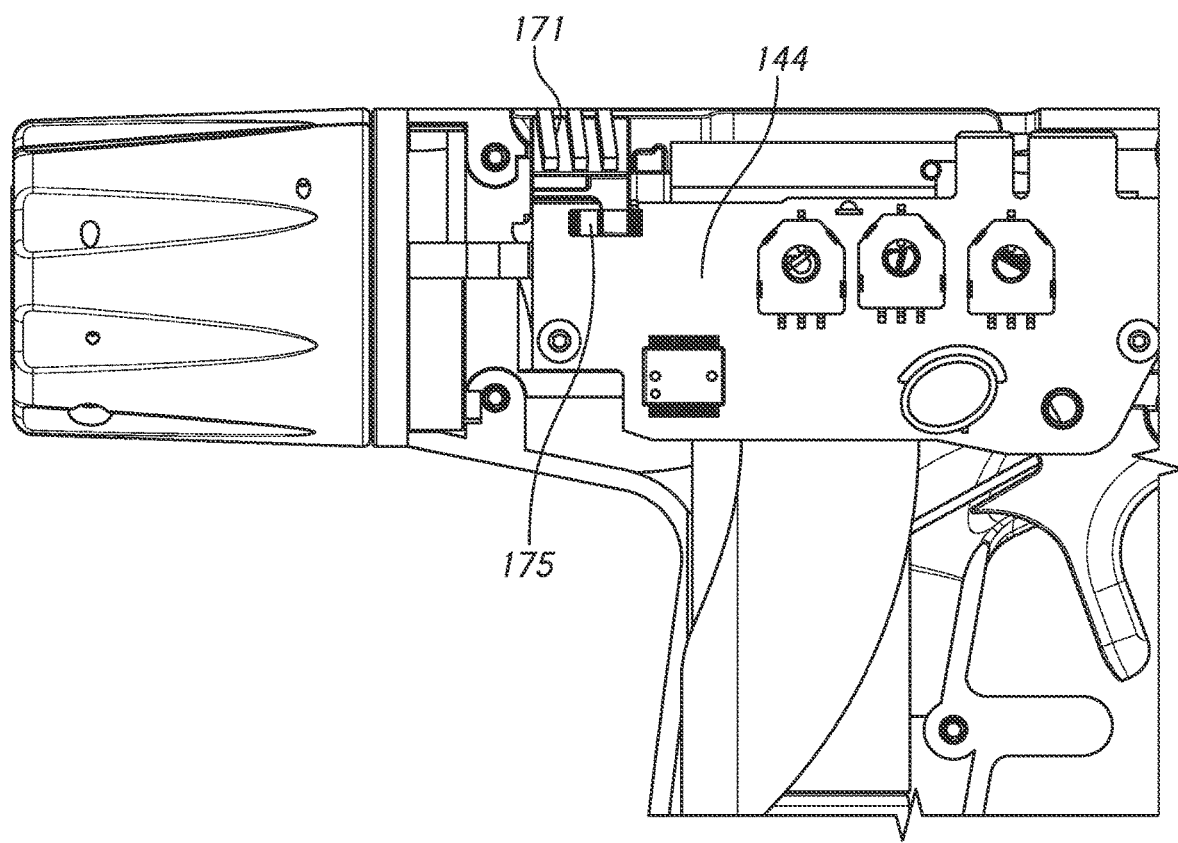
FIG. 24 is a partial cut-away side view of the powered handle of FIG. 2 with the override return mechanism unlocked for movement to a return configuration.

With reference to FIGS. 23 and 24, when the return lock is slid proximally to unlock the return mechanism, the return lock 171 can be electrically coupled to the control unit of the handle assembly to depower the handle assembly. Thus, once the return lock mechanism has been operated, the handle can be disabled from further use even if a user attempts to manually reposition the manual return mechanism and the drive system for repeat use. In the illustrated embodiment, when the handle assembly is configured for powered operation (FIG. 23), the return lock is electrically disengaged from the circuit board 144 having the control unit. When the return lock is slid proximally to unlock the return mechanism, the return lock proximally moves a stamped spring component 175 that electrically engages a circuit on the circuit board 144 to depower the handle assembly. The spring component 175 is configured for proximal movement only and does not return distally even if the return lock is returned distally to its initial position. Thus, unlocking the return mechanism by sliding the return lock 171 permanently disables the powered functionality of the handle assembly.

Figure 25:
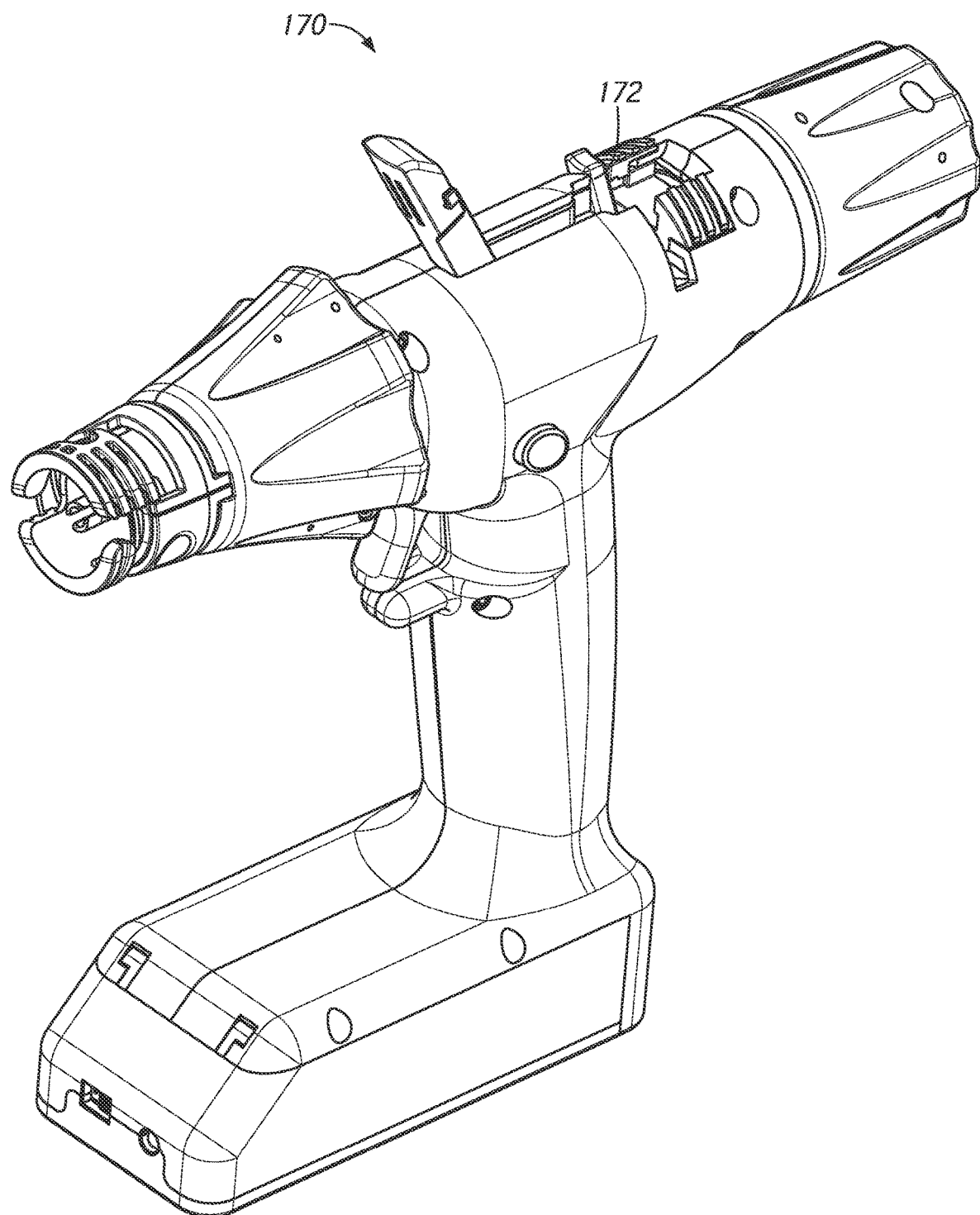
FIG. 25 is a perspective view of the powered handle of FIG. 2 with the override return mechanism in a return configuration.
Figure 26:
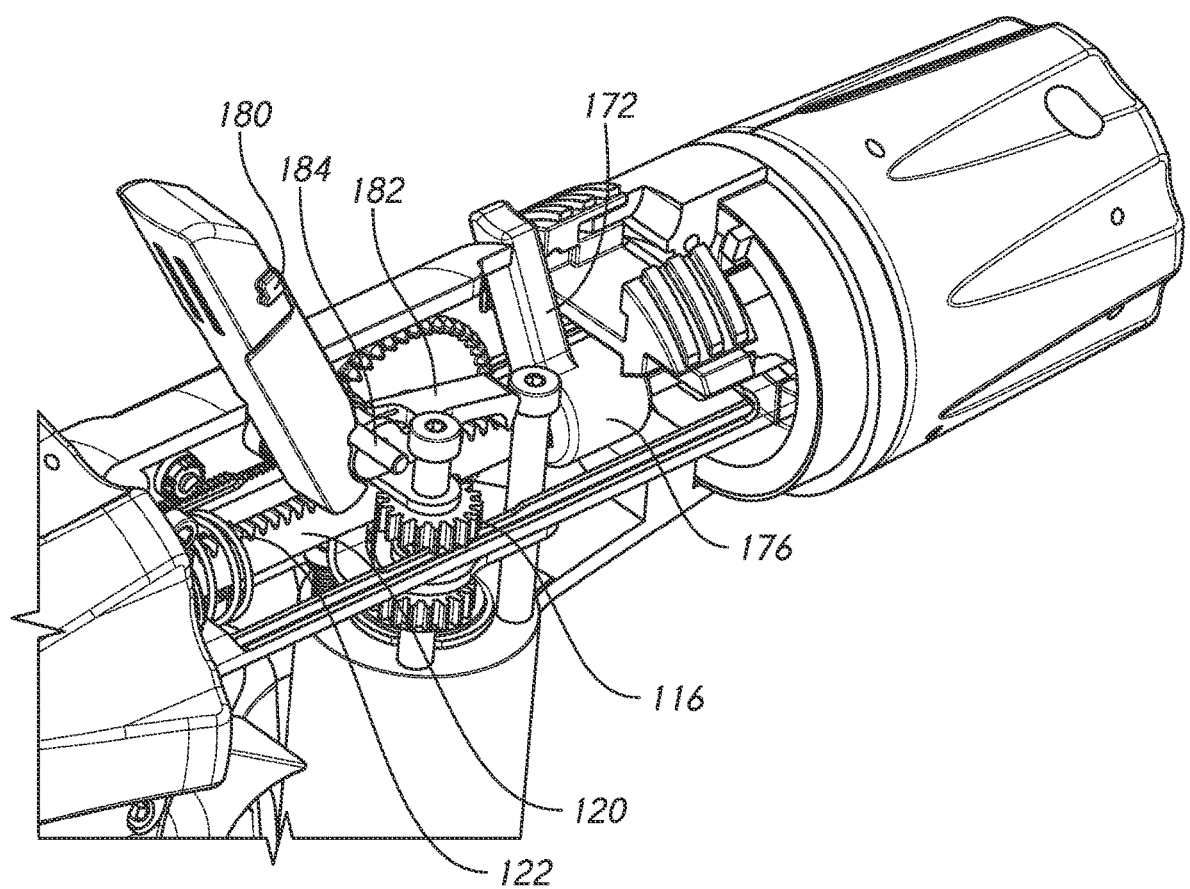
FIG. 26 is a perspective partial cut-away view of the powered handle of FIG. 2 with the override return mechanism in a return configuration.

With reference to FIGS. 25 and 26, to operate the shaft rotation mechanism of the manual return mechanism 170, a user rotates a rotation lever 172 extending to on an outer surface of the handle, now unblocked by movement of the return lock. The rotation lever 172 is coupled to a shaft rotation collar rotationally coupled to the actuation shaft. In the illustrated embodiment, the actuation shaft 120 extends through the shaft rotation collar 176 and is slideable therethrough. Thus, rotating the shaft rotation collar 176 rotates the actuation shaft 120 approximately 90 degrees about the longitudinal axis thereof. This rotation positions the rack 122 of the actuation shaft out of engagement with the auxiliary gear 116 of the drive system. This rotation can be accomplished without affecting the actuation adapter since the actuation shaft 120 is rotatably coupled to the actuation adapter (FIG. 5).

While the illustrated embodiment includes a shaft rotation mechanism having a rotation lever 172 rotated by a user, in other embodiments, the shaft rotation mechanism can be configured to self-deploy upon proximal movement of the return lock. For example, a self-deploying shaft rotation mechanism can include a shaft rotation collar having a torsional bias. In certain embodiments, the shaft rotation collar is coupled to the handle assembly by a torsion spring. When the return lock is slid proximally, the torsional bias of the shaft rotation tends to rotate the actuation rack to disengage the actuation rack from the auxiliary gear and to engage the actuation rack with the shaft retraction mechanism.

Figure 27:
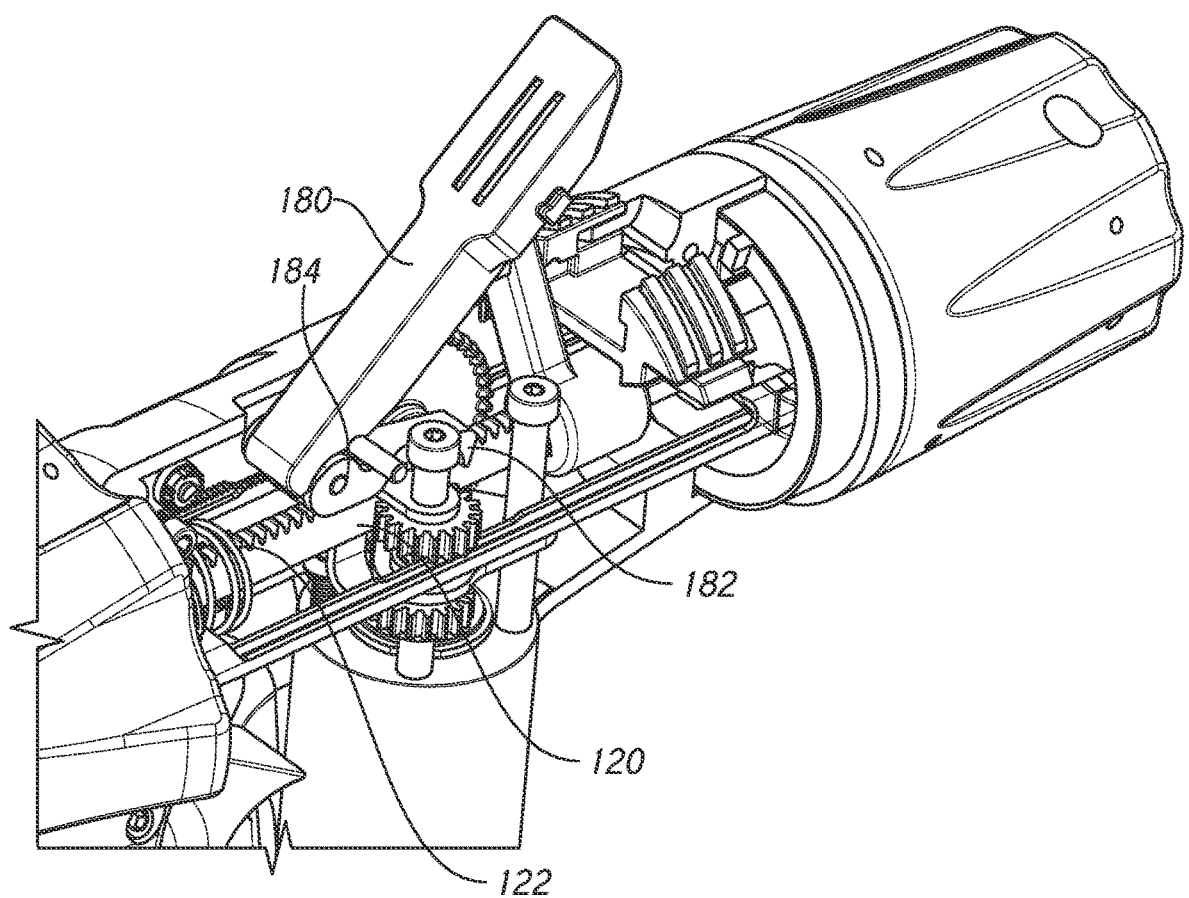
FIG. 27 is a perspective partial cut-away view of the powered handle of FIG. 2 with the override return mechanism in a return configuration and a manual return cycle initiated.

With reference to FIGS. 26 and 27, once the shaft rotation mechanism has been operated, the shaft retraction mechanism can be operated to return the actuation shaft proximally within the handle. Sliding the return lock proximally within the handle assembly unlocks a return lever 180 on the powered handle. The return lever 180 is pivotably coupled to a return pawl 182 at a pivot joint 184. When the rack 122 of the actuation shaft 120 was rotated out of engagement with the drive system, it was rotated into engagement with the shaft retraction mechanism. The return lever 180 can be rotated through one or a series of return cycles (FIGS. 26, 27) to engage the return pawl 182 with the rack 122 on the actuation shaft 120 and retract the actuation shaft 120 proximally within the handle in a ratchet-type operation.

Figure 27A:
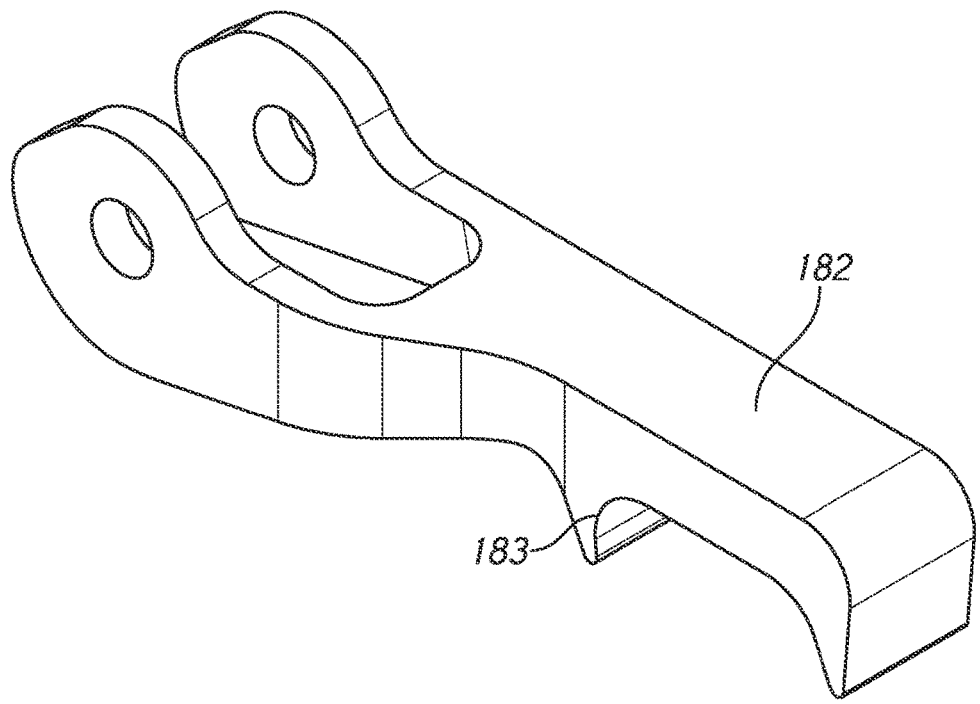
FIG. 27A is a perspective view of a return pawl of the override return mechanism of the powered handle of FIG. 2.
Figure 27B:
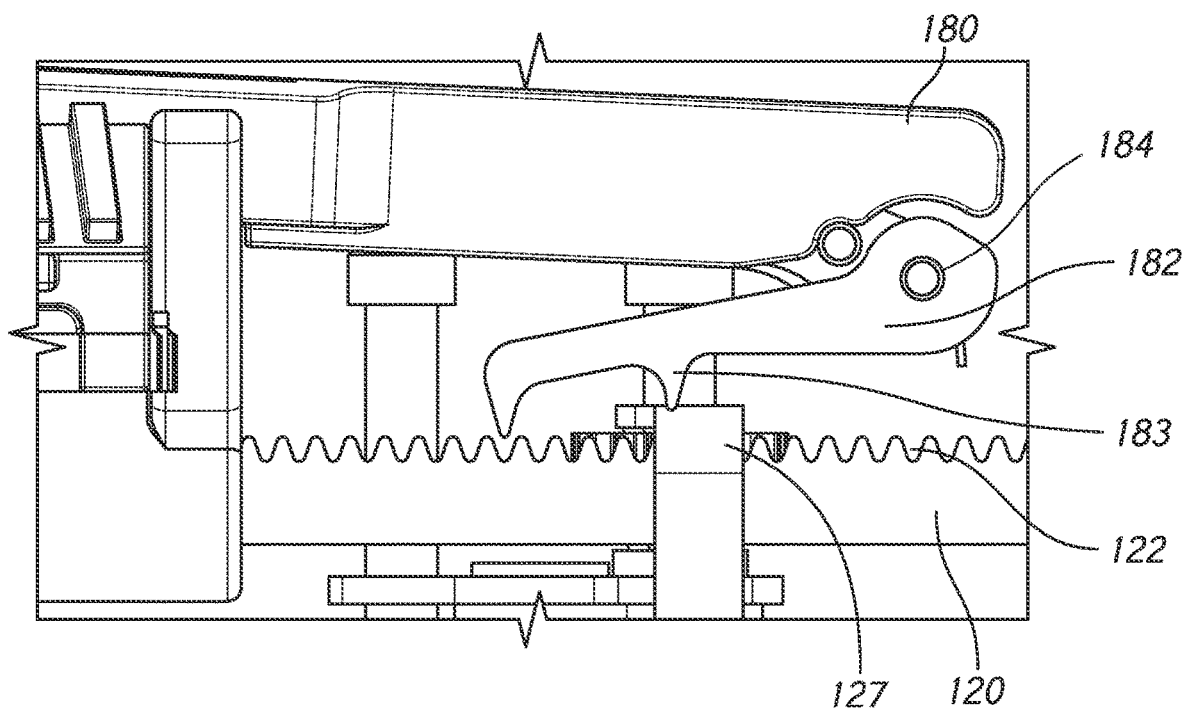
FIG. 27B is a side view of the override return mechanism of the powered handle of FIG. 2.
Figure 27C:
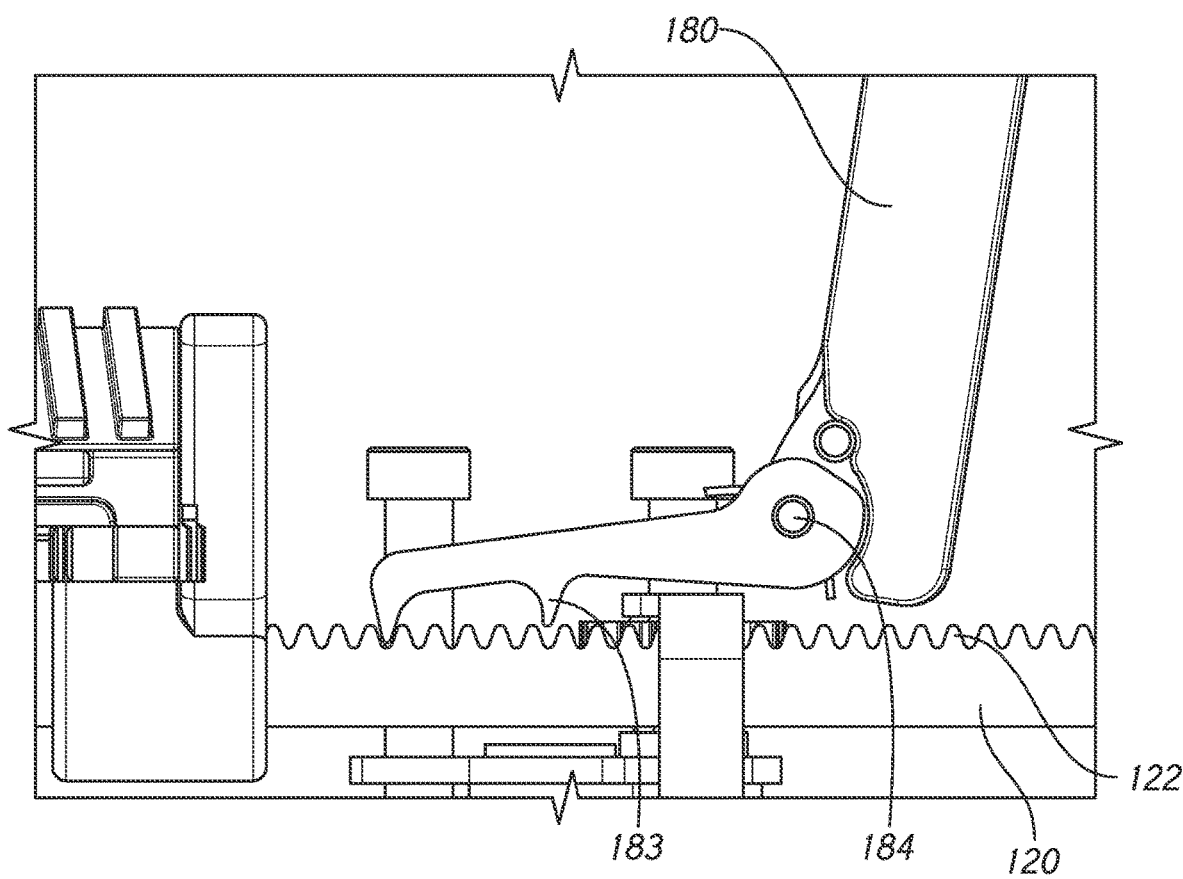
FIG. 27C is a side view of the override return mechanism of the powered handle of FIG. 2.
Figure 28:
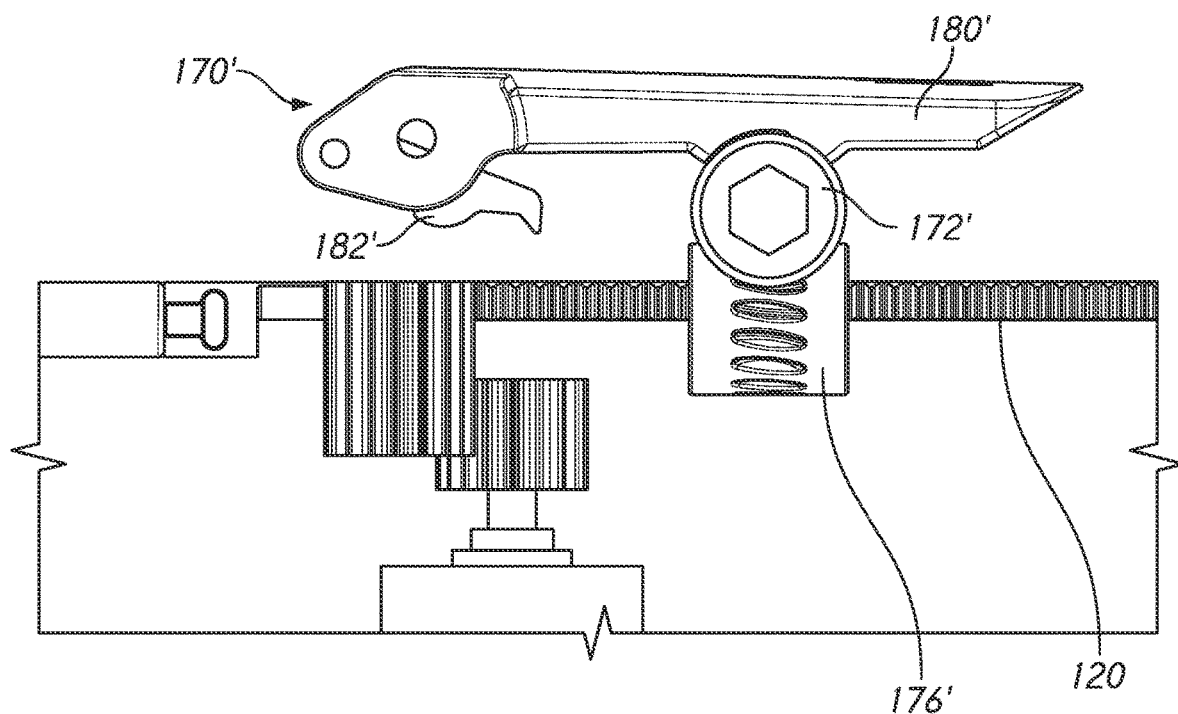
FIG. 28 is a side view of another embodiment of override return mechanism for a surgical stapler.
Figure 29:
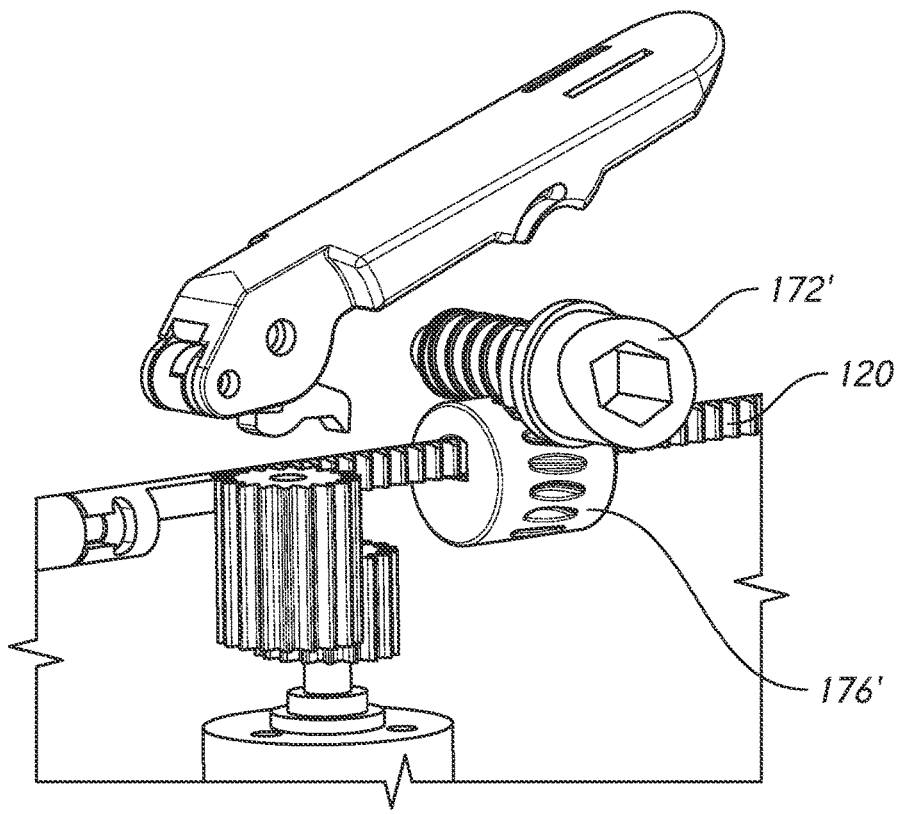
FIG. 29 is a perspective view of the override return mechanism of FIG. 28.
Figure 30:
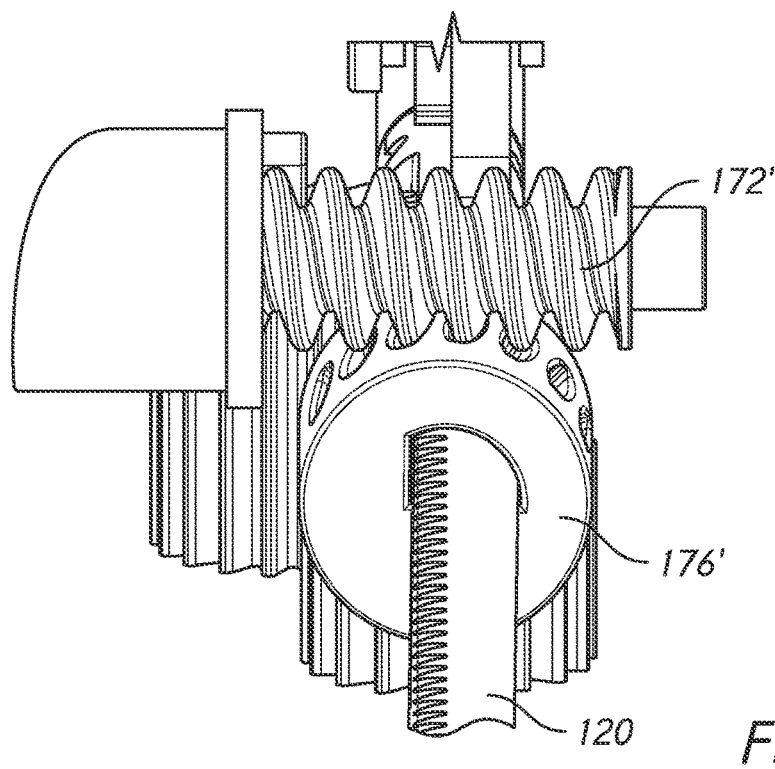
FIG. 30 is a perspective view of the override return mechanism of FIG. 28.

With reference to FIGS. 27A-27C, the return pawl 182 can be configured to facilitate actuation shaft retraction. In the illustrated embodiment, the return pawl 182 comprises a protruding boss or second pawl tooth 183 that is positioned to interact with the guide member 127 of the motor mount during a portion of the return cycle. During powered operation of the handle assembly, the second pawl tooth 183 contacts the guide member 127, and the return pawl 182 is limited from engaging the rack 122 of the actuation shaft 120 (FIG. 27B). Desirably, during operation of the manual return mechanism, the second pawl tooth 183 can be positioned to limit engagement of the return pawl 182 with the rack 122 during a portion of the return cycle where a user would otherwise have relatively low mechanical advantage. As illustrated, the second pawl tooth 183 prevents the return pawl 182 from engaging the rack 122 until the return lever 180 is positioned at a predetermined angle relative to a longitudinal axis of the actuation shaft 120 to provide a desired mechanical advantage (FIG. 27C).

Figure 31:
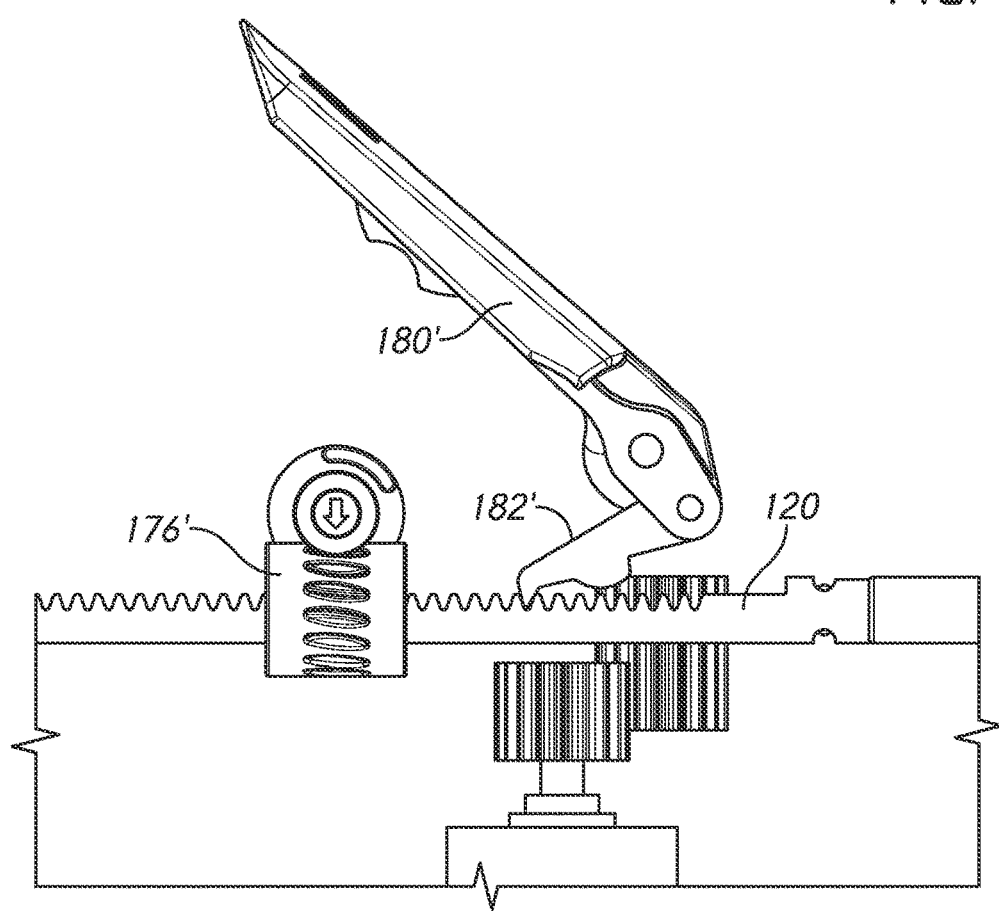
FIG. 31 is a side view of the override return mechanism of FIG. 28.

With reference to FIGS. 28-31, another embodiment of manual return mechanism for the powered handle is illustrated. The components and operation of the manual return mechanism 170' are similar to that described above with respect to the manual return mechanism 170 of FIGS. 20-27. However, in use of the manual return mechanism 170', the return lock and shaft rotation mechanism functionality can be provided by a worm gear-driven shaft rotation collar 176'. Thus, a user can initially rotate the actuation shaft 120 away from the powered drive system by rotating a worm gear drive such as, for example, with a hexagonal key. Through rotation of the worm gear, the shaft rotation mechanism releases a shaft retraction mechanism, disengages the actuation rack from the powered drive, and positions the actuation rack into engagement with the shaft retraction mechanism (FIG. 31). The shaft retraction mechanism of the manual return mechanism 170' includes similar ratchet-type operation with a return lever 180' pivotably coupled to a return pawl 182' as that discussed above with respect to the manual return mechanism 170.

Two-Position Lockout Mechanism

Figure 32:
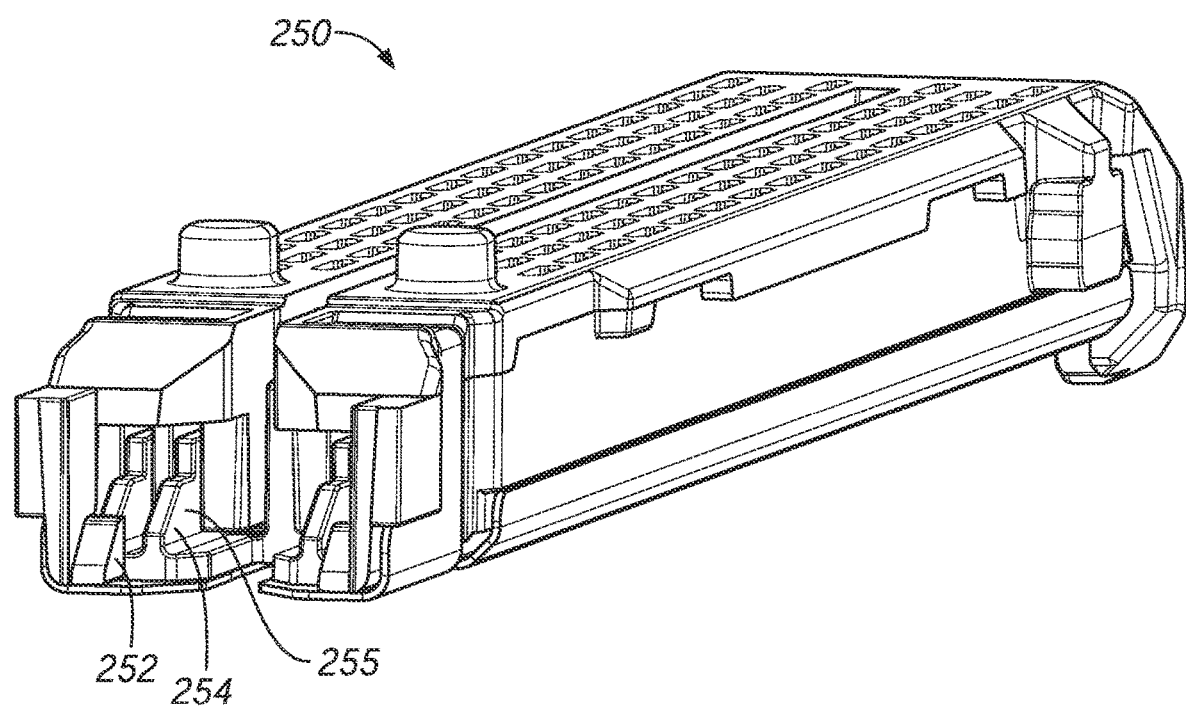
FIG. 32 is a perspective view of a reload cartridge for use in certain embodiments of surgical stapling device.

With reference to FIG. 32, a reload cartridge 250 for use with an elongate shaft of a surgical stapler device having separate empty jaw assembly and fired reload lockout mechanisms is illustrated. As further described below, if no reload cartridge 250 is present in the jaw assembly and a user attempts to grasp the jaw assembly in an open-close stroke, a two-position lockout lever will move to a first, locked position. As illustrated, the reload cartridge includes a first lockout actuator sized and positioned to position a two-position lockout lever in a second position to defeat the empty jaw assembly lockout mechanism when a reload is positioned in the reload support of the jaw assembly. The first lockout actuator can comprise a ramped boss 252 extending laterally inwardly from a side wall of a body of the cartridge.

With continued reference to FIG. 32, in the illustrated embodiment the reload cartridge 250 includes a second lockout actuator sized and configured to position a two-position lockout lever in an unlocked position to defeat the fired reload lockout mechanism when an unfired reload is positioned in the jaw assembly. Thus, in addition to the two lockout positions, the two-position lockout lever is pivotable to an unlocked position. In certain embodiments, the second lockout actuator comprises a tail 254 extending proximally from a slider 255 of the reload cartridge 250. When the reload cartridge 250 is in an unfired state, the slider 255 is in a proximal position such that the slider tail 254 extends proximally to engage the lockout lever. As the firing member is advanced distally in a firing stroke, it abuts the slider within the reload cartridge and advances the slider distally. Thus, once the reload cartridge 250 is in a partially fired (or fully fired) state, the proximally-extending slider tail 254 is not in position to defeat the fired reload lockout mechanism.

Figure 33:
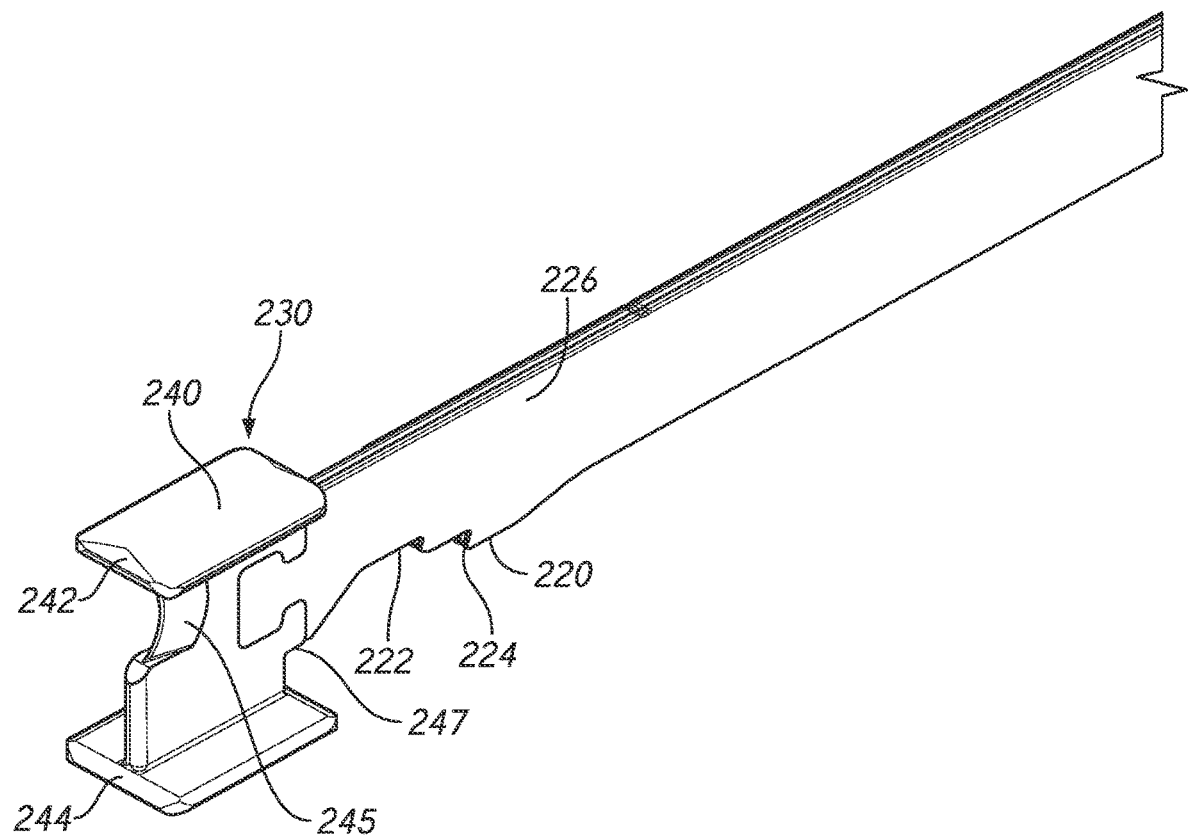
FIG. 33 is a perspective view of a firing beam and firing member for use in certain embodiments of elongate shaft assembly of a surgical stapling device.

With reference to FIG. 33, a firing beam 226 for use with an elongate shaft assembly of a surgical stapler device having separate empty jaw assembly and fired reload lockout mechanisms is illustrated. The firing beam 226 extends from a proximal end to a distal end 230. A firing member 240 having a generally I-beam configuration is disposed at the distal end 230 of the firing beam 226. Upper and lower horizontal flanges 242, 244 of the I-beam firing member 240 ride in channels in the first and second jaws of the jaw assembly to approximate the jaws, then maintain spacing of the jaws during staple firing. A cutting blade 245 is positioned on the vertical portion of the I-beam profile to transect tissue between rows of staples. The I-beam firing member 240 can be attached to the distal end of the firing beam 226 by an interlock fit, welding, another joining technique, or some combination thereof. A proximal edge of the I-beam firing member 240 can have a proximally-extending projection or tail 247 that can rest on a proximal portion of a lockout lever with the firing beam 226 in a fully retracted position corresponding to an open jaw assembly.

With continued reference to FIG. 33, the firing beam can include a first lockout notch 222 for use in conjunction with the empty jaw assembly lockout mechanism and a second lockout notch 224 for use in conjunction with the fired reload lockout mechanism. In the illustrated embodiment, the first lockout notch 222 extends a first height from an adjacent lower edge 220 of the firing beam 226. As further described below, the first height is selected to correspond to a height of the proximal end of the lockout lever when the empty jaw assembly lockout has been actuated by an attempt to approximate a jaw assembly without a reload cartridge present.

With continued reference to FIG. 33, in the illustrated embodiment, the second lockout notch 224 is positioned on the firing beam proximal of the first lockout notch 222. The second lockout notch 224 extends a second height from the adjacent lower edge 220 of the firing beam 226. As further described below, the second height is selected to correspond to a height of the proximal end of the lockout lever when the fired reload lockout mechanism has been actuated by an attempt to fire a previously fired or partially fired reload.

The illustrated embodiment of firing beam 226 has a first lockout notch 222 and a second lockout notch 224 that are substantially contiguous such that the adjacent lower edge 220 of the firing beam is relieved over a longitudinal span corresponding to the first lockout notch 222 and the second lockout notch 224. It is contemplated that in other embodiments, the first lockout notch and the second lockout notch can be spaced from one another by an unrelieved segment of the lower edge of the firing beam. As further described herein, the heights and longitudinal positions of the first lockout notch and the second lockout notch can be configured to achieve desired operational characteristics of a stapler handle assembly.

Figure 34:
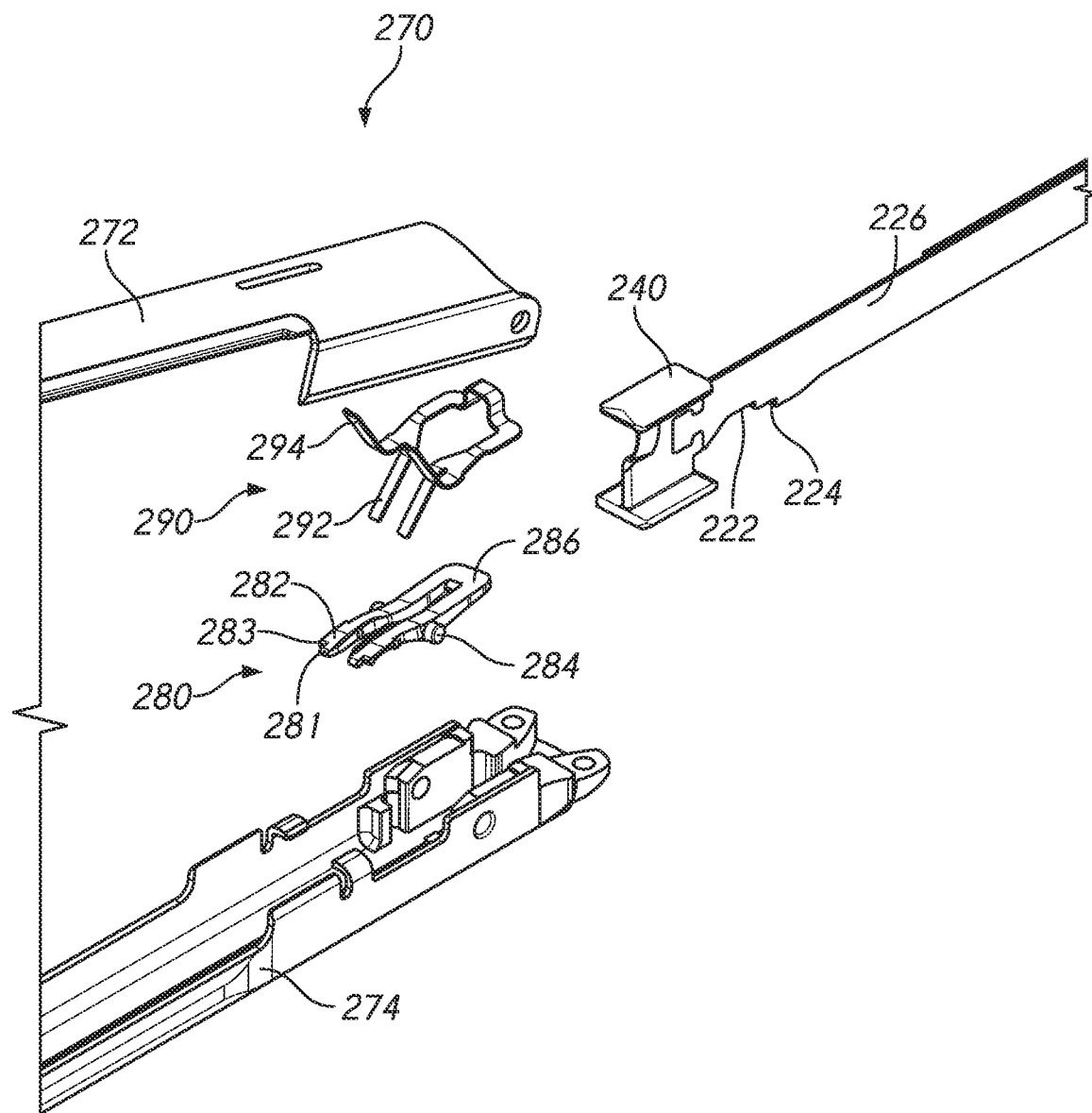
FIG. 34 is a partially exploded perspective view of a proximal end of a jaw assembly of certain embodiments of elongate shaft assembly of a surgical stapling device.
Figure 35:
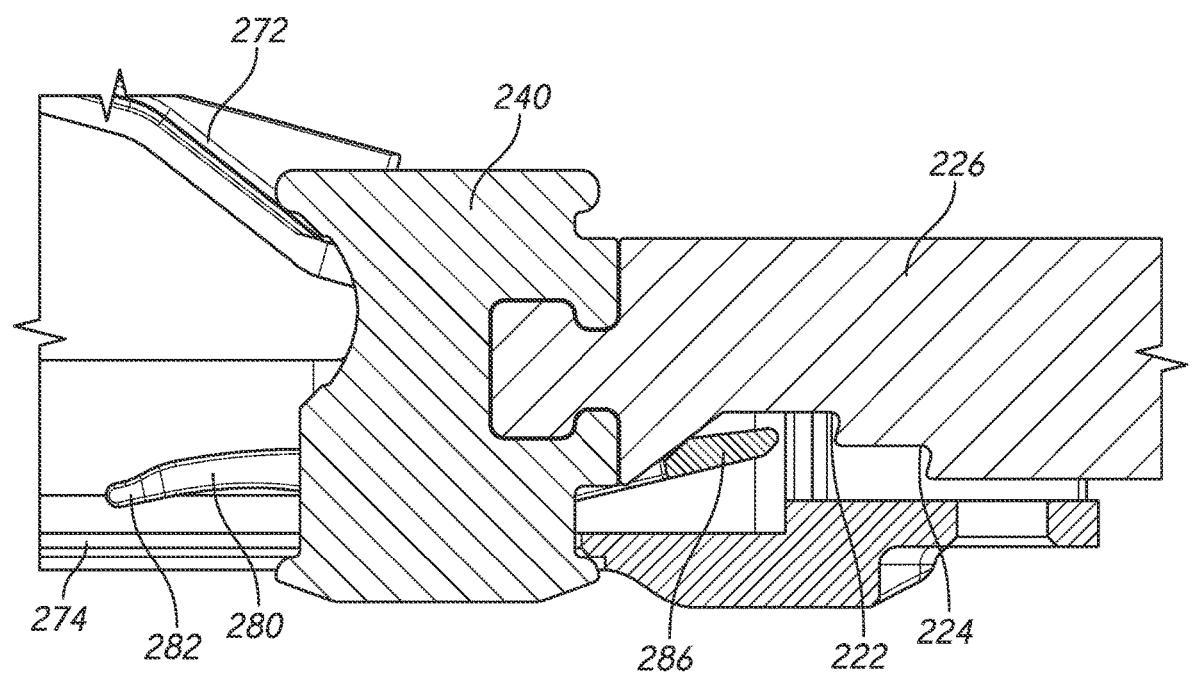
FIG. 35 is a cut away side view of a proximal end of a jaw assembly of certain embodiments of elongate shaft assembly of a surgical stapling device.

With reference to FIGS. 34 and 35, a portion of the jaw assembly 270 is illustrated in partially exploded (FIG. 34) and cut away side views (FIG. 35), with various components hidden for illustration of the empty jaw assembly lockout mechanism and the fired reload lockout mechanism. In certain embodiments, the lockout mechanisms comprise a two-position lockout lever 280, a biasing spring 290, a first lockout notch 222, and a second lockout notch 224. The three position lockout lever 280 has a distal end 282 configured to engage a first lockout actuator and a second lockout actuator on a reload cartridge, a pivot 284 proximal the distal end, and a proximal end 286 configured to engage either the first lockout notch, the second lockout notch, or neither. The biasing spring 290 has at least one lower spring arm 292 biasing the end of the lockout lever 280 distal the pivot 284 in a downward direction towards the reload support of the second jaw 274. In the illustrated embodiment, the biasing spring has two lower spring arms 292 with a gap therebetween allowing passage of the firing member 240 and the firing beam 226. The biasing spring 290 can have at least one upper spring arm 294 that biases the first jaw 272 towards an open configuration. The biasing spring 290 can be configured to sit astride the firing beam 226 and can have a central saddle member from which the at least one lower spring arm 292 and the at least one upper spring arm 294 extend.

Figure 38:
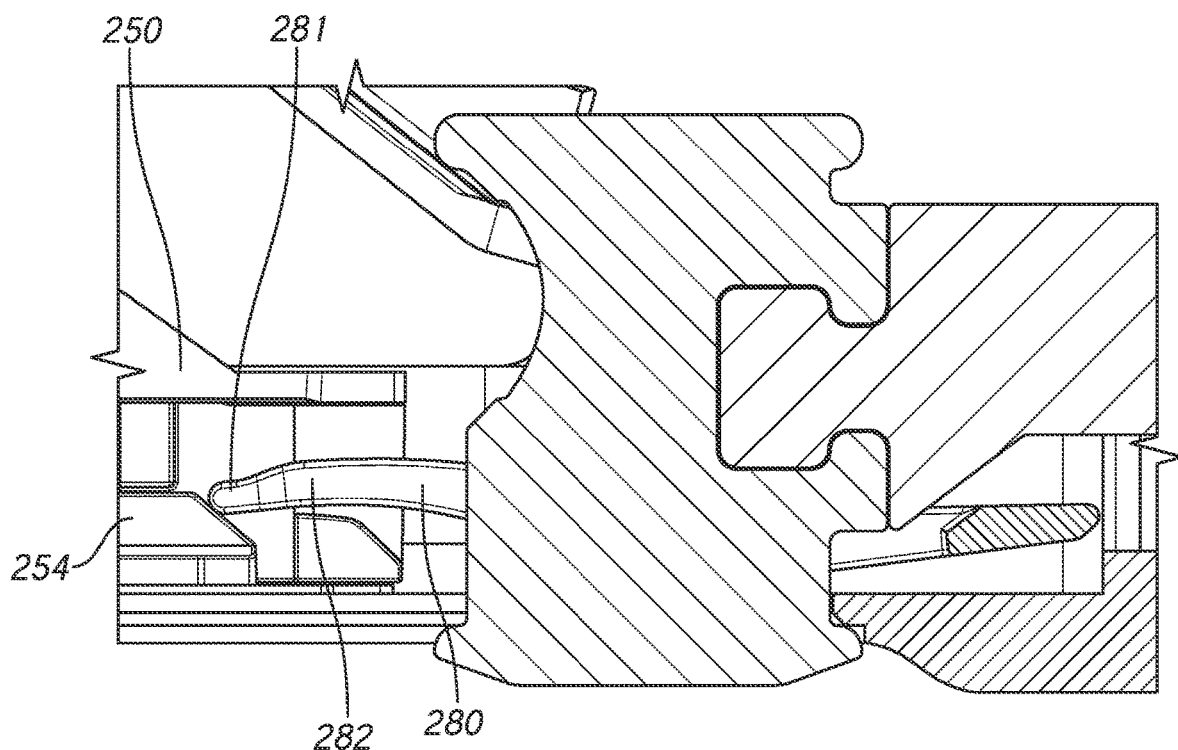
FIG. 38 is a cut away side view of the proximal end of the jaw assembly of FIG. 35 with an unfired reload partially inserted.
Figure 39:
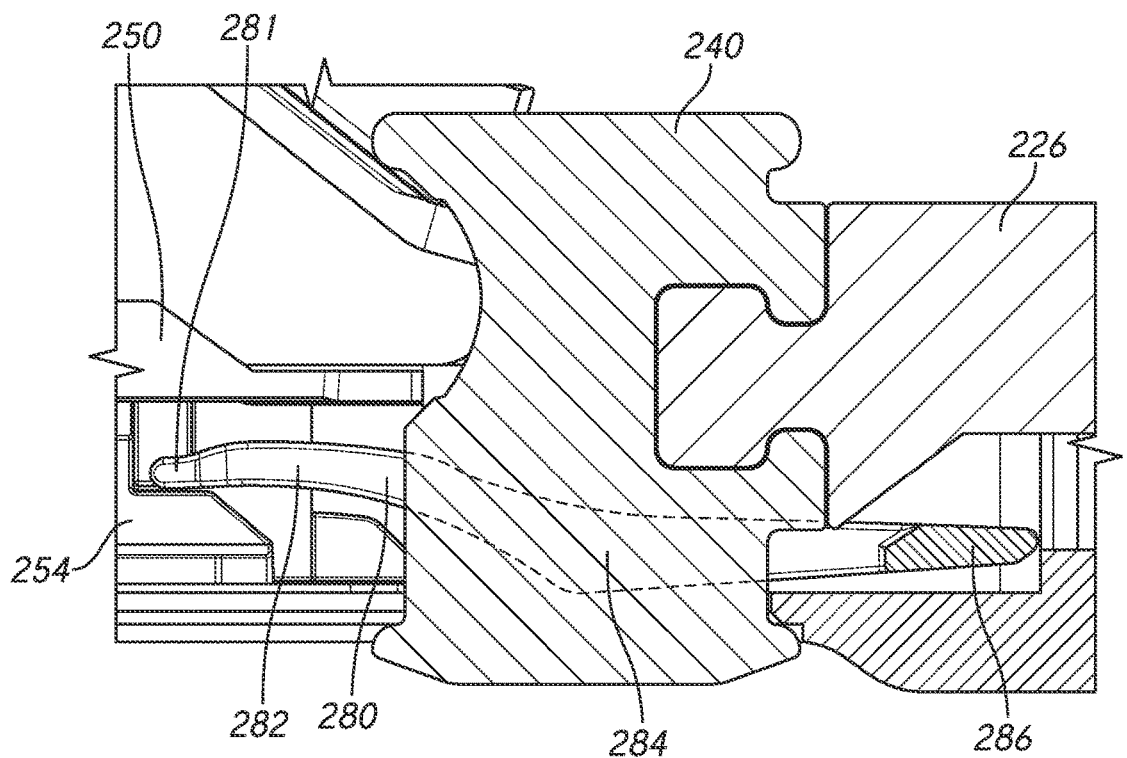
FIG. 39 is a cut away side view of the proximal end of the jaw assembly of FIG. 35 with an unfired reload inserted.
Figure 40:
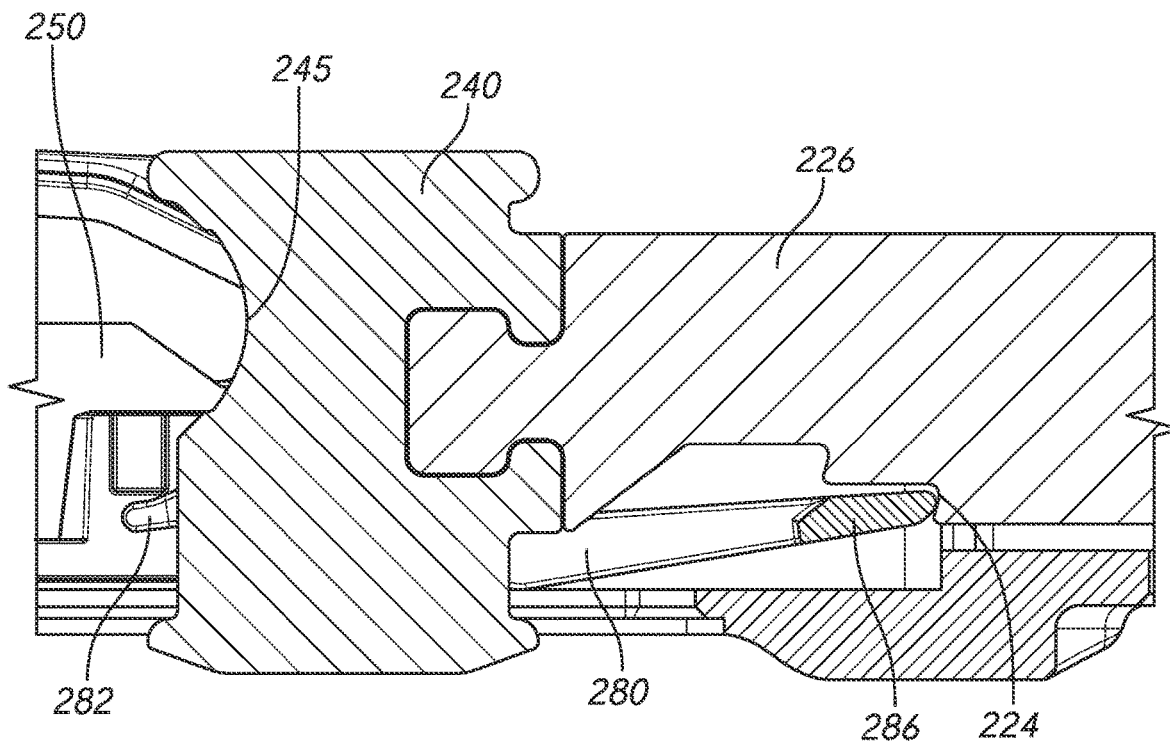
FIG. 40 is a cut away side view of the proximal end of the jaw assembly of FIG. 35 with an at least partially fired reload inserted.
Figure 41:
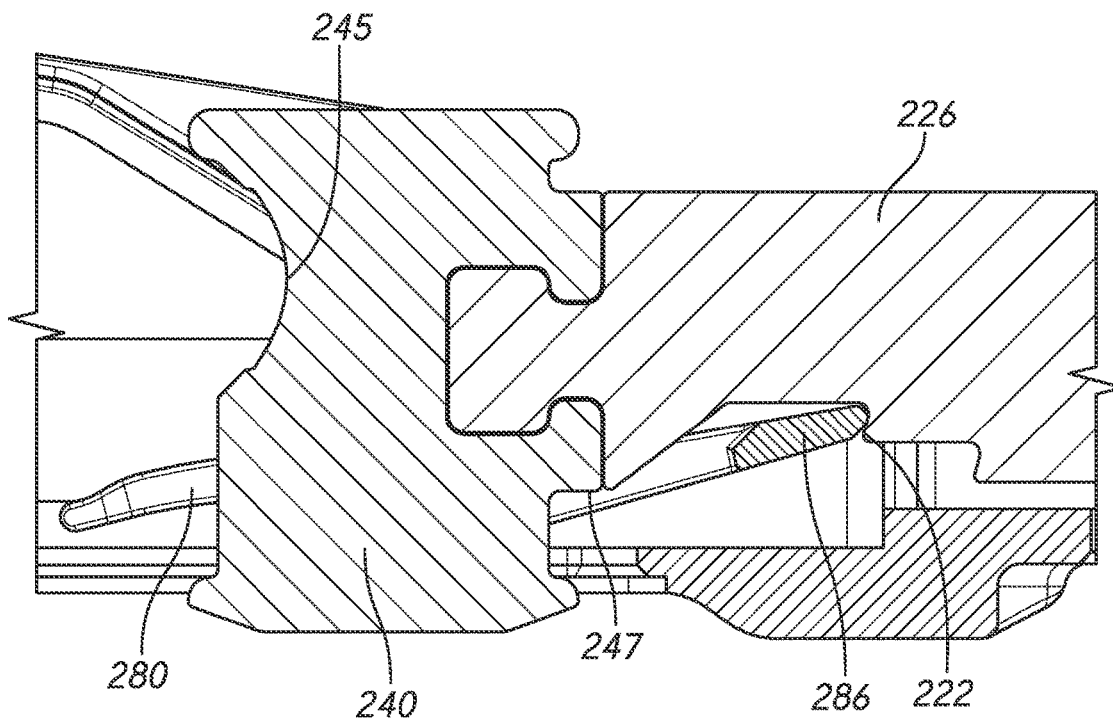
FIG. 41 is a cut away side view of the proximal end of the jaw assembly of FIG. 35 with no reload inserted.

With reference to FIGS. 36-41, operation of the two lockout mechanisms is illustrated. In these partial cut away side views of a proximal end of certain embodiments of jaw assembly, certain elements of the jaw assembly (such as biasing spring) are not illustrated, and certain components (such as firing member 240) are illustrated as transparent elements to enhance visibility of the operation of the lockout mechanisms. FIGS. 36-39 illustrate functioning of the lockout mechanisms as a full, unfired staple reload 250 cartridge is positioned in the reload support of the second jaw 274. FIG. 40 illustrates operation of the fired reload lockout mechanism. FIG. 41 illustrates operation of the empty jaw assembly lockout mechanism.

Figure 36:
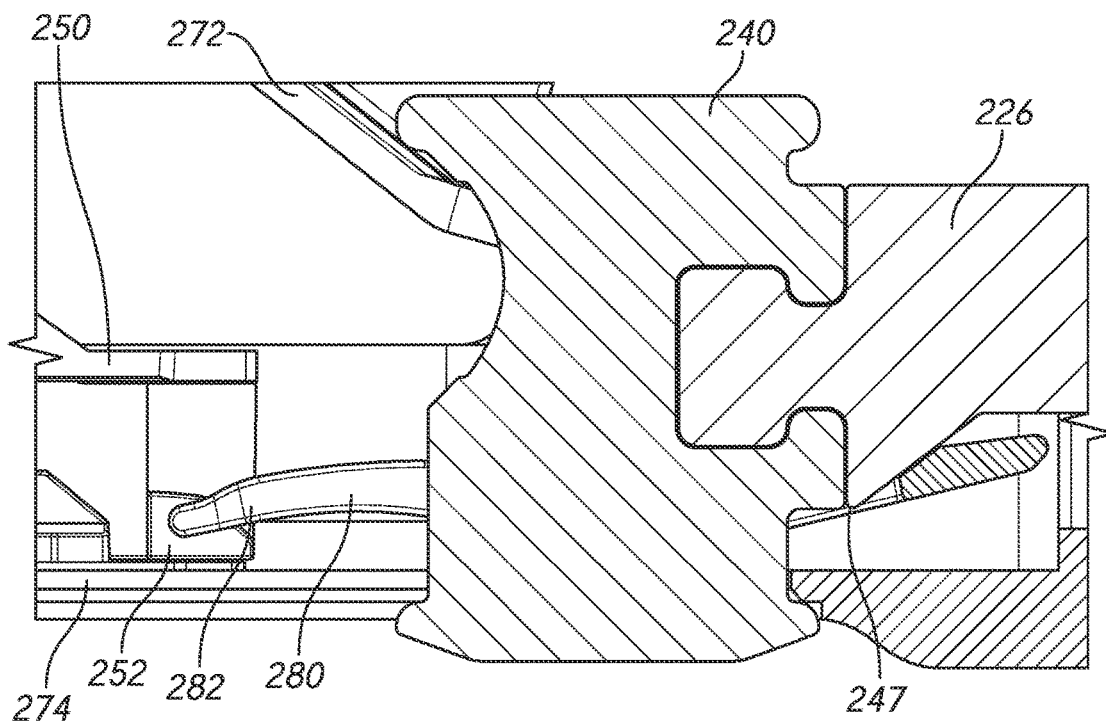
FIG. 36 is a cut away side view of the proximal end of the jaw assembly of FIG. 35 with an unfired reload partially inserted.

With reference to FIG. 36, a cut away view of the proximal end of the jaw assembly is illustrated. The jaw assembly is in an open configuration such that the first jaw 272 is biased to an open position relative to the second jaw 274. The firing member 240 and firing beam 226 are in a fully proximally retracted position such that a proximal surface of the lockout lever 280 rests on a proximally extending tail 247 of the firing member 240. Thus, the distal end 282 of the lockout lever 280 is raised slightly away from the reload support such that a lockout actuator can be positioned between the reload support and the lockout lever 280.

With continued reference to FIG. 36, the slight raise of the distal end 282 of the lockout lever 280 can accept a ramped proximal surface of the first lockout actuator or ramped boss 252 formed on the reload cartridge body. The distal end 282 of the lockout lever 280 has a lateral extension 283 (FIG. 34) positioned to engage the first lockout actuator and a medial surface 281 (FIG. 34) positioned to engage the second lockout actuator as the reload cartridge 250 is slid proximally upon insertion to the reload support of the jaw assembly.

Figure 37:
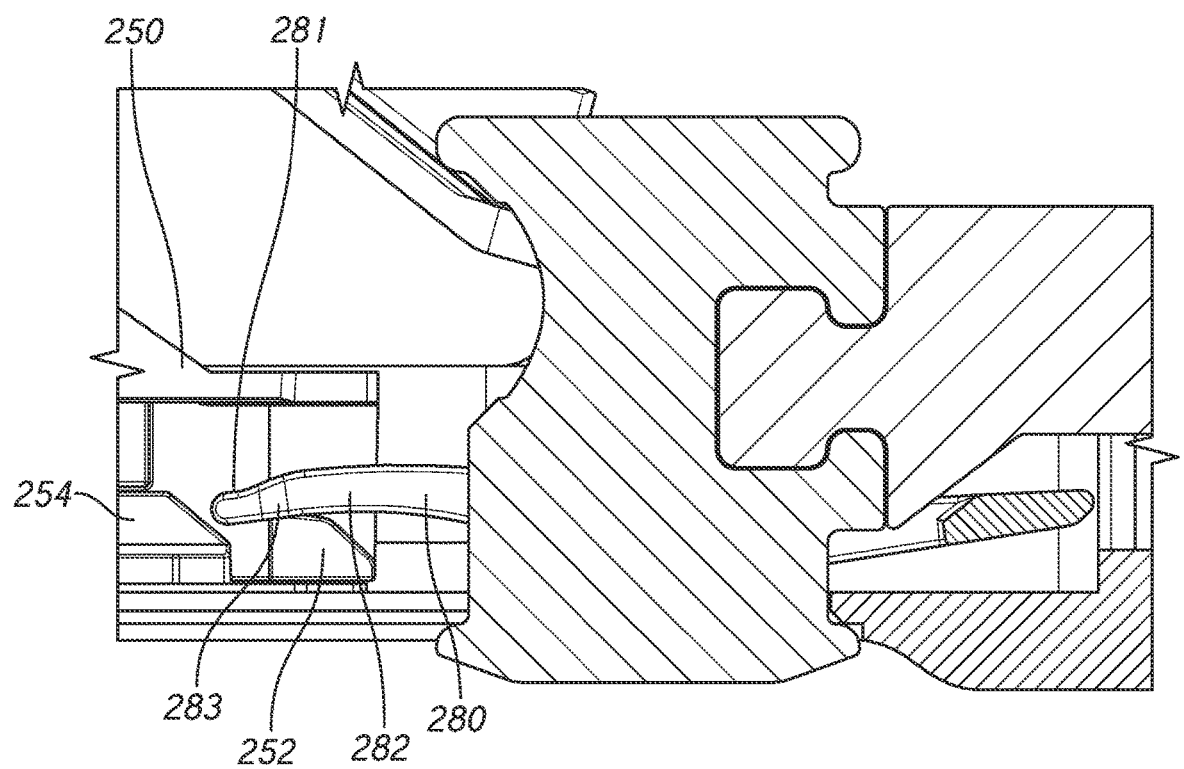
FIG. 37 is a cut away side view of the proximal end of the jaw assembly of FIG. 35 with an unfired reload partially inserted.

With reference to FIG. 37, a cut away view of the proximal end of the jaw assembly is illustrated with the reload 250 cartridge partially inserted. As illustrated, the lateral extension 283 of the distal end 282 of the lockout lever 280 has engaged a ramped proximal surface 283 of the ramped boss 252. As the reload 250 cartridge is further slid proximally, the lateral extension 283 travels up the ramped surface to a first height relative to the reload support, pivoting the lockout lever 280 into the second position and defeating the empty jaw assembly lockout mechanism. Operation of the empty jaw assembly lockout mechanism is further described below with reference to FIG. 41. In the illustrated embodiment, the second lockout actuator or slider tail 254 of an unfired reload 250 cartridge is positioned just distal of the first lockout actuator at a height positioned to engage with the medial surface 281 of the distal end 282 of the lockout lever 280 once the distal end 282 of the lockout lever 280 has been raised to the first height from the reload support by the first lockout actuator. Accordingly, when viewed in a cut away side view, as illustrated in FIG. 37, the first lockout actuator and second lockout actuator define a progressive ramped profile arranged to elevate the distal end 282 of the lockout lever 280 to two predefined positions as a reload 250 cartridge is inserted into the reload support.

With reference to FIG. 38, a cut away view of the proximal end of the jaw assembly is illustrated with the reload 250 cartridge almost fully inserted. As illustrated, the medial surface 281 on the distal end 282 of the lockout lever 280 has engaged a ramped proximal surface of the second lockout actuator or slider tail 254. In the illustrated embodiment, the proximally extending tail 254 of the slider of the reload 250 has a lead-in ramped surface that, with the reload cartridge in an unfired state, engages the distal end 282 of the lockout lever 280. In certain embodiments, the lockout lever 280 and slider tail 254 can be configured to provide a smooth, relatively low friction reload insertion and reduce the possibility of binding or inadvertent advancement of the slider during insertion of the cartridge. For example, in certain embodiments, the medial surface 281 of the distal end 282 of the lockout lever 280 can have a radiused distal tip such that the lockout lever 280 will be pivoted by interaction with the slider tail despite potential slight angular misalignments between the reload 250 cartridge and the reload support. Moreover, in certain embodiments, the ramped proximal surface of the slider tail 254 can extend from a first height relative to the reload support at a proximal end that is smaller than a height of the first lockout actuator relative to the reload support. Accordingly, as an unfired reload 250 cartridge is positioned in the reload support, the distal end 282 of the lockout lever 280 can transition from the first lockout actuator to the second lockout actuator smoothly at a wide range of angular alignments between the reload cartridge and reload support.

With reference to FIG. 39, a cut away view of the proximal end of the jaw assembly is illustrated with the reload 250 cartridge fully inserted. As illustrated, the medial surface 281 on the distal end 282 of the lockout lever 280 has been advanced along the ramped proximal surface of the second lockout actuator and onto the second lockout actuator or slider tail 254. This advancement along the ramped surface of the slider tail 254 pivots the lockout lever 280 about the pivot 284 such that the distal end 282 of the lockout lever 280 is at a second height with respect to the reload support. With the distal end of the lockout lever 280 at the second height, the lockout lever is in an unlocked position, corresponding to an unlocked state of the empty jaw assembly lockout mechanism and an unlocked state of the fired reload lockout mechanism.

With continued reference to FIG. 39, with the lockout lever 280 in the unlocked position, the proximal end 286 of the lockout lever 280 is positioned at a height below a lower edge of the firing beam. Accordingly, the firing member 240 and firing beam 226 can be distally advanced through an open-close stroke and a firing stroke responsive to user input from an operatively coupled mechanical or powered handle assembly (FIGS. 1-5). Accordingly, when an unfired reload cartridge is inserted to the reload support of the jaw assembly, both the empty jaw assembly lockout mechanism and the fired reload lockout mechanism are defeated to allow a user to operate a stapler handle assembly to grasp tissue with the jaw assembly and fire staples from the jaw assembly by distal translation of the firing beam and firing member within the jaw assembly.

With reference to FIG. 40, once a reload 250 cartridge has been at least partially fired, the slider within the reload 250 is advanced distally from a proximal, unfired position. Upon completion of a firing stroke, the slider remains at a distal location within the reload cartridge while the firing beam 226 and firing member 240 can be retracted proximally responsive to operation of a handle assembly in a return or retraction stroke. Thus, once a reload 250 cartridge has been partially or fully fired the second lockout actuator or slider tail is not in position to engage the distal end 282 of the lockout lever 280. In certain embodiments, the first lockout actuator or ramped boss 252, however, is stationary relative to a body of the cartridge. Thus, with a partially or fully fired reload 250 positioned in the reload support, the distal end 282 of the lockout lever 280 is engaged by the first lockout actuator to position the distal end 282 of the lockout lever 280 at the first height relative to the reload support. With the distal end 282 of the lockout lever 280 at the first height, corresponding to the second position of the lockout lever, the empty jaw assembly lockout mechanism is defeated, but the fired reload lockout mechanism is locked.

With continued reference to FIG. 40, with the lockout lever 280 in the second position, the proximal end 286 of the lockout lever 280 is at a height corresponding to the second lockout notch 224 on the firing beam 226. Moreover, in certain embodiments, the biasing spring 290 (FIG. 34) exerts a force on an upper surface of the distal end 282 of the lockout lever 280, tending to maintain the proximal end 286 of the lockout lever 280 at the height corresponding to the second lockout notch 224 on the firing beam 226. Accordingly, if a user attempts to actuate the jaw assembly with a fired reload cartridge present in the jaw assembly, the firing beam 226 can be distally advanced until the proximal end 286 of the lockout lever 280 seats within the second lockout notch 224 of the firing beam 226, indicating engagement of the fired reload lockout mechanism and preventing further distal motion of the firing beam and the firing member.

With continued reference to FIG. 40, in certain embodiments the fired reload lockout mechanism can be configured to permit operation of the jaw assembly of the stapling device in at least a portion of an open-close stroke. For example, in certain embodiments, the position of the second lockout notch 224 and the length of the lockout lever 280 can be sized and configured such that the firing beam 226 is arrested upon engagement of the fired reload mechanism at a position corresponding to a fully closed or almost fully closed configuration of the jaw assembly. With the jaw assembly in such a configuration, the firing member 240 has advanced to a distal position that approximates the first jaw and the second jaw but maintains the cutting edge 245 in a substantially recessed location. Advantageously, with the fired reload lockout configured to permit an open-close stroke, after firing staples from a reload cartridge, a user can operate the jaw assembly in one or more open-close strokes to assess tissue thicknesses and consistency at various locations for application of a potential second reload. Likewise, as insertion of a stapling device through a surgical access port such as a trocar can typically require the jaw assembly to be in a closed configuration, a user could withdraw and reinsert the jaw assembly through one or more surgical access ports to evaluate tissue thicknesses and consistency at various locations in a surgical site.

With continued reference to FIG. 40, in certain embodiments, the fired reload lockout mechanism can be further configured to prevent operation of the stapling device in a firing stroke. Mechanical and powered stapler handle assemblies configured for use with an elongate shaft and jaw assembly as described herein, such as those discussed above with respect to FIGS. 1-5, typically include firing mode selector mechanisms or firing safety switches to allow a user to affirmatively select operation of a firing stroke of the jaw assembly only once the jaw assembly has been positioned in a closed configuration. Thus, in certain embodiments, the position of the second lockout notch 224 and the length of the lockout lever 280 can be sized and configured such that the firing beam is arrested upon engagement of the fired reload lockout mechanism at a position corresponding to a position proximal to a fully closed configuration of the jaw assembly. Thus, in these embodiments, once the fired reload lockout mechanism has been engaged, a user would be unable to select operation of the firing stroke on the handle assembly. Advantageously, operation of the fired reload lockout mechanism to prevent selection of the firing stroke on the handle assembly would serve as an indication to the user that a lockout had been engaged.

With reference to FIG. 41, a cut away view of the proximal end of the jaw assembly is illustrated with no reload cartridge inserted and the firing member and firing beam slightly longitudinally advanced. With no reload present, once the tail 247 of the firing member 240 advances off of the proximal end 286 of the lockout lever 280, the biasing spring 290 (FIG. 34) exerts force on the upper surface of the distal end 282 of the lockout lever 280 towards the reload support. Thus, upon initial advancement of the firing beam 226 responsive to a user actuating a handle assembly to advance the jaw assembly in an open-close stroke, the lockout lever 280 is pivoted into a first position corresponding to a locked configuration of the empty jaw assembly lockout mechanism. As the firing beam 226 is advanced distally, the proximal end 286 of the lockout lever 280 seats in the first lockout notch 222 on the firing beam 226 and engages the empty jaw assembly lockout mechanism, preventing further distal translation of the firing beam 226 and firing member 240.

With continued reference to FIG. 41, in certain embodiments the empty jaw assembly lockout mechanism can be configured to arrest motion of the firing beam at a position corresponding to a substantially open configuration of the jaw assembly. For example, the position of the first lockout notch 222 on the firing beam 226, the length of the lockout lever 280, and the length of the tail 247 of the firing member 240 can be sized and configured such that the empty reload lockout mechanism is locked early in an open-close stroke of the jaw assembly. Advantageously, with the empty jaw assembly lockout mechanism configured to lock during an initial portion of the open-close stroke, a user would be unable to actuate a handle assembly to close the jaw assembly sufficiently to be inserted through a surgical access port if no reload cartridge were present in the jaw assembly. Thus, with an empty jaw assembly lockout mechanism so configured, a user would have a tactile indication that no reload cartridge is present in the jaw assembly before inadvertently introducing an empty jaw assembly to a surgical site. Moreover, such an empty jaw assembly lockout desirably maintains the cutting edge 245 of the firing member 240 in a substantially retracted, shielded position relative to the jaw assembly with no reload present in the jaw assembly.

Light Ring User Display

In certain embodiments, the handle assembly can include a control unit that processes and, in some instances stores or saves to a memory module, operating data including information about difficulty of firing, information about the test time, and state of the device. It can thus be desirable that the stapler include a user display to convey certain operational information to a surgeon so that he or she can make an intelligent decision about the firing they are about to perform. For example, in some instances, it can be desirable to provide a user with certain information regarding clamping time and whether the clamped tissue has a thickness that is appropriate to staple over within the operational parameters of the staple reload cartridge in the end effector of the stapler.

Figure 42:
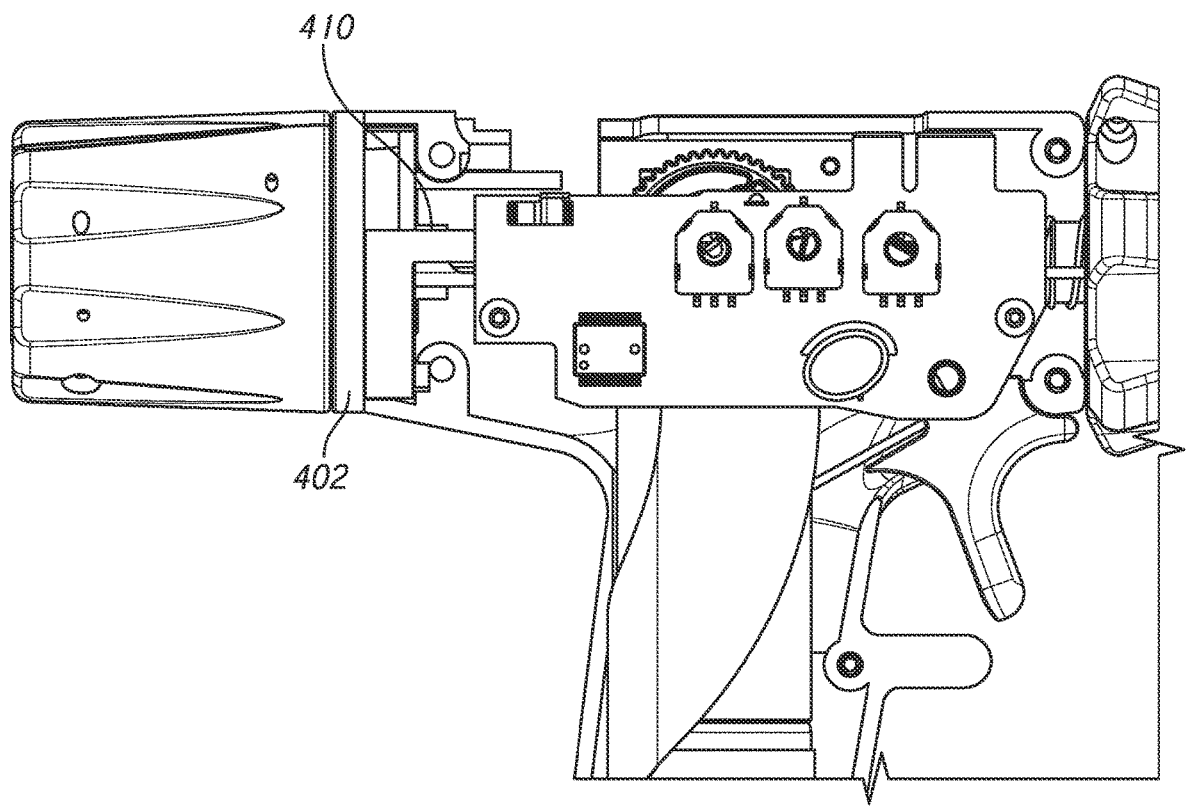
FIG. 42 is a partial cut-away side view of the powered handle of FIG. 2 with an electrically coupled light ring user display.

With reference to FIG. 42, in certain embodiments, the handle assembly can include a multifunction illuminated display such as an annular illuminated "light ring" user display 402 subassembly as a user display. Advantageously, the annular configuration of the light ring subassembly provides high visibility of the user display to the operator from any device orientation as the handle assembly is repositioned and manipulated to various angular orientations during a surgical procedure.

Figure 43:
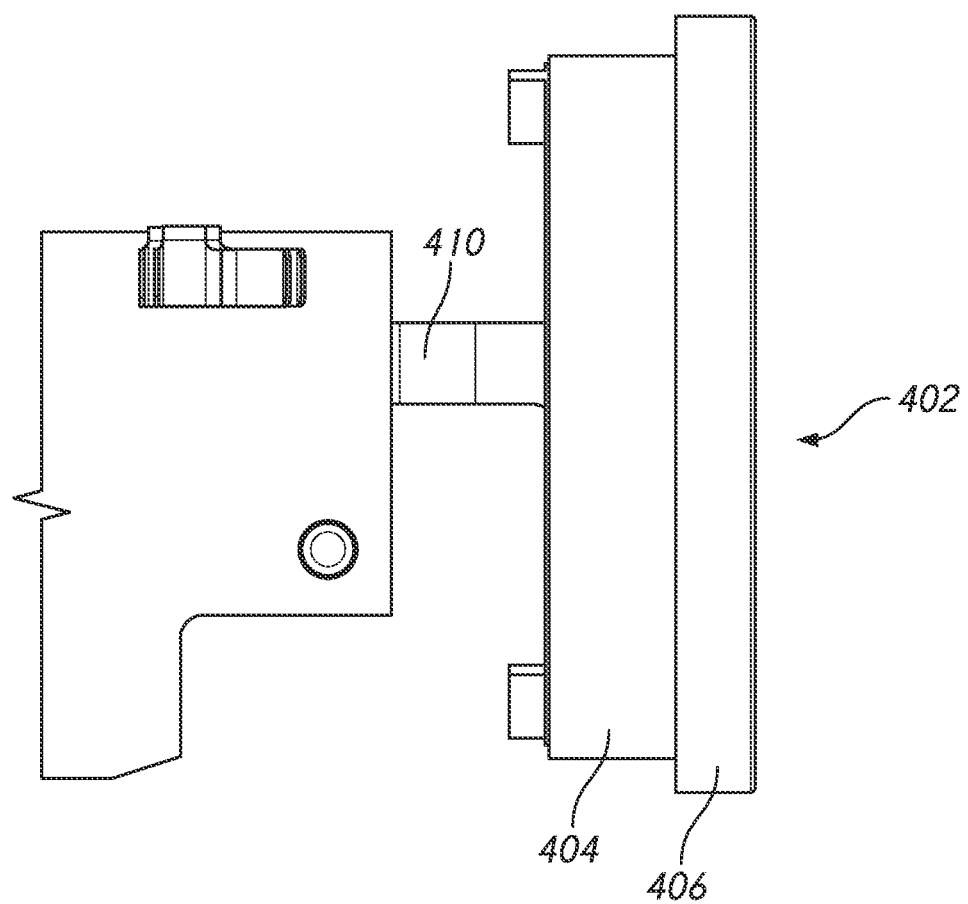
FIG. 43 is a side view of the light ring user display of the powered handle of FIG. 2.
Figure 44:
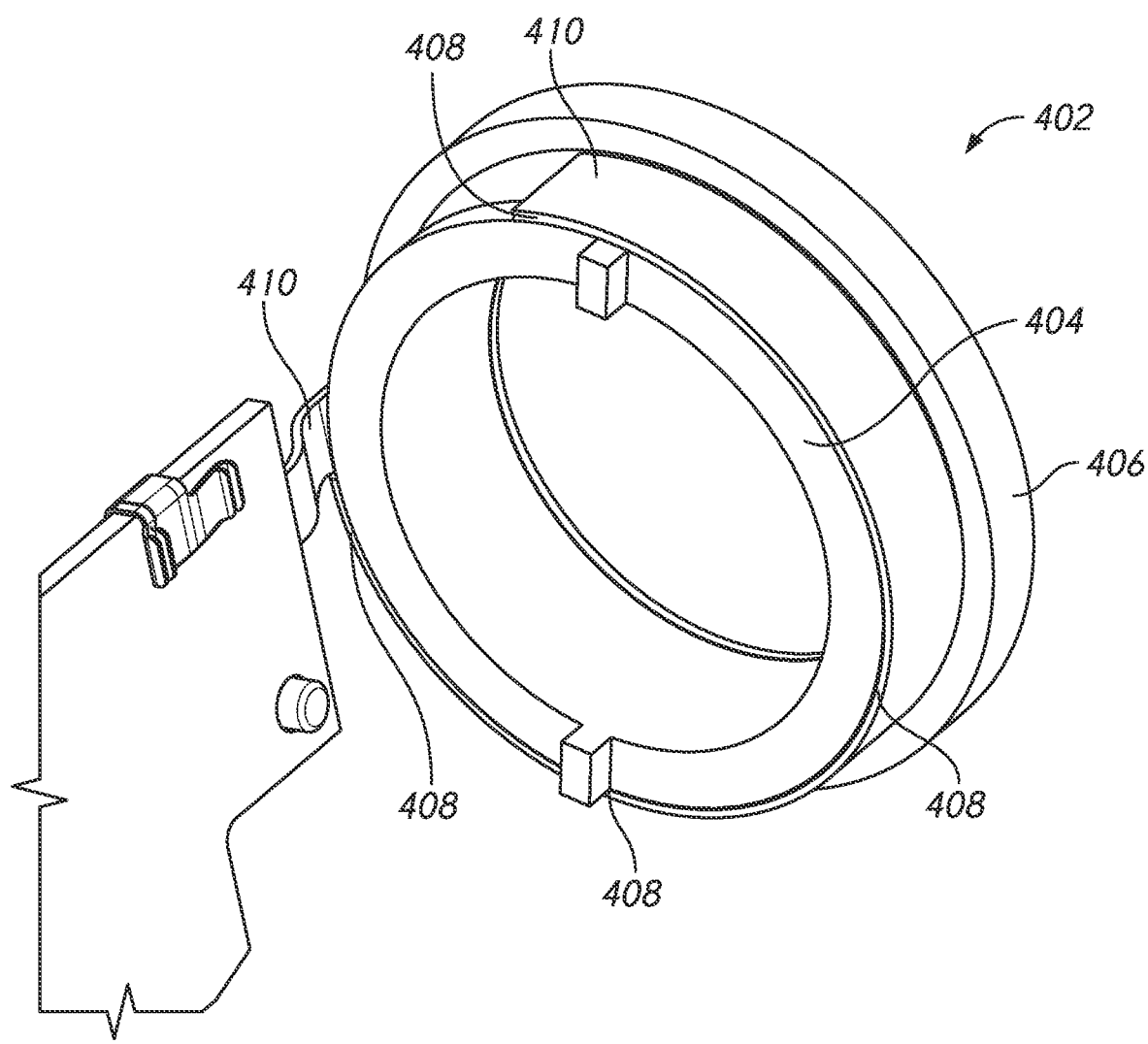
FIG. 44 is a perspective view of the light ring user display of the powered handle of FIG. 2.

With reference to FIGS. 43-44, in the illustrated embodiment, the light ring user display 402 comprises an annular light reflector 404, an annular light ring 406, and a plurality of light sources 408. The annular light reflector 404 is positioned radially inwardly of the annular light ring 406 such that illumination from light sources 408 shining radially inwardly reflect off of the annular light reflector and are transmitted through the annular light ring. The material of the light ring 406 can be selected to allow a high degree of light transmission while controlling light dispersion to avoid external bright spots visible to the user. As illustrated, the user display 402 comprises four light sources 408, approximately equally spaced about the light ring user display 402. In certain embodiments, the light sources can each comprise an RGB light emitting diode that is capable of illuminating in a wide variety of colors and brightnesses. The light ring user display 402 can be electrically coupled to the control unit of the handle assembly, such as a circuit board over a flexible printed circuit board such as a Rigid Flex printed circuit board. As illustrated, the flexible printed circuit board 410 can be formed into an annular configuration and positioned between the annular light ring 406 and the annular light reflector 404. The light sources 408 can be mounted to an inner surface of the flexible electrical cable 410 to emit light radially inwardly towards the annular light reflector 404. Desirably, the shape of the flexible printed circuit board and the housing reflector can easily allow the light sources to be held at any angle to maximize reflected light and minimize bright spots.

Although one embodiment of a light ring user display 402 is illustrated and discussed above, it is contemplated that other embodiments of light ring user display can include other aspects. For example, in certain embodiments, more or fewer than four light sources 408 can be used in the light ring user display and different or additional illuminating technologies can be used. In some embodiments, the light sources can be positioned on an outer surface of the flexible electrical cable 410 to emit directly through the annular light ring 406 with no annular light reflector in the light ring user display. In other embodiments, a surface formed on one or both halves of a housing of the handle assembly can be used to emit light from the light sources without the use of a separate annular light ring.

With reference to FIG. 42, it is contemplated that the light ring user display 402 can be electrically coupled to the control unit and configured to display a variety of status messages to a user. For example the color, brightness, flashing sequence, or steady on/off illumination can be controlled to convey desired information to a user. Additionally, in some embodiments, the occurrence of and/or speed of a particular color transition, or brightness transition can be used to convey information to a user. In some display control profiles, a first color can be used to indicate the handle is in an open-to-clamp functionality with no possibility of a firing actuation while a second color can be used to indicate the stapler is in a firing mode configured to fire staples. Additional colors or other indicia can be used to represent other events or operational states of the stapler such as: a firing has been completed and the firing mechanism is being reversed; and that a firing error has occurred.

In certain embodiments, a user display for a powered handle comprises two groups of RGB LEDs: (1) The status indicator, and (2) the LED ring. The status indicator is an "always-on" light that indicates to users that sufficient power to the microcontroller is being correctly supplied. Thus, the status indicator can quickly indicate to the user that the powered handle is "off" or "on."

In embodiments having a separate status indicator and LED ring, the status indicator can be an RGB LED assembly currently commercially available as Sun LED part number XZFBBM2ACRDG92W-3 and the LED ring can comprise an additional four of these RGB LED assemblies. In an exemplary circuit to drive the status indicator and LED ring, each RGB LED assembly has three shunt resistors, one corresponding to each color. The shunt resistors have the same value for each color on each RGB LED assembly. The shunt resistors are in 0603 packages which are available up to ¼ Watt so that the brightness can be altered by increasing or decreasing the current. Current to the RGB LED assemblies can be controlled through MMBT2222A transistors each with 1.00 kΩ base, with all LEDs of the same color being controlled by a single transistor such that the status indicator comprises three transistors corresponding to the red, green, and blue LEDs thereof, and the LED ring comprises three transistors, each transistor electrically coupled to all of the red, green, and blue LEDs thereof.

In certain embodiments, the LED ring is the system's primary user interface for indicating handle operational status, which is determined by a light control scheme in a control system for the handle assembly. Specific device states correlate with an indication color (white/blue/green/yellow/red/off), brightness, and duty cycle. Operators and assistants are instructed to use the indications supplied through the LED for setup, use, and troubleshooting of the device. Advantageously, the LED ring, positioned at a proximal end of the handle assembly and extending radially around the handle clearly indicates the condition of the powered handle to the operator and other members of the surgical staff with the handle in any orientation relative to the surgical site. Previous staplers in field are known to have too many notifications that can be positioned at a single location that can be difficult to see in certain orientations and can thus be hard for users and other medical personnel to interpret. In contrast, the led indication system coupled with the light control scheme (state machine/alarm tables) offers clear, simplified indications of all necessary device operational statuses.

The light control scheme can be configured to alert users of invalid manufacturing or calibration data, device damage and/or incorrect setup prior to use in a procedure. Desirably, the light control scheme and LED light ring can allow for faster device troubleshooting and use by interpreting device status to user. Advantageously, the light control scheme implemented in a control microcontroller can turn on each color on and off and can pulse width modulate each color to achieve a range of brightnesses.

In certain embodiments, the light control scheme can apply a first indicia to indicate a user alarm state in the powered handle system. For example, the first indicia can comprise a flashing red color of the LED ring. In some embodiments, the user alarm state can comprise an indication that the handle has exceeded a predetermined number of firings, an indication that the handle has been powered in excess of a predetermined time, or an indication that the handle has a battery with a relatively low battery life. Moreover, a user alarm state can comprise an indication that the trigger appears stuck over a predetermined time threshold, that a fire button appears stuck over a predetermined time threshold, that the actuation shaft position is out of range or doesn't appear to be changing, or that the motor current exceeds a predetermined maximum limit. Moreover, a user alarm state can comprise an indication that a manual return mechanism has been actuated or that a hardware or control system fault has been encountered. In addition to alerting a user through the light control scheme, upon encountering a user alarm state, the control system can disable all handle functionality.

In certain embodiments, the light control scheme can display a second indicia to indicate a handle end of life state in the powered handle system during operation. The second indicia can comprise a solid red illumination of the LED ring. Should a handle assembly encounter an end of life state during operation, which can correspond to a maximum number of firings having been made, a maximum powered time having elapsed, or a depleted battery. The control system can alert a user of the handle end of life condition with the light control scheme displaying a second indicia and can allow the handle assembly to operate in a grasping mode until a subsequent power cycle at which point, the control system can disable the handle assembly.

In certain embodiments, the light control scheme can display a third indicia to indicate user attention is desired to continue a stapling operation. The third indicia can comprise a flashing yellow illumination of the LED ring. Certain instances during operation of the powered stapler can be advanced with further user input. For example, if a firing button or trigger is being depressed during certain operational sequences for a length of time that is below a predetermined threshold indicating a stuck button or trigger, the third indicia can indicate to a user that the button or trigger should be released to allow the sequence to proceed. For example, if the trigger is depressed for a time less than a threshold indicting a stuck trigger when a reload shaft assembly is initially loaded, when the jaws are fully closed prior to a staple firing, or once the stapler has been fully fired, the light control scheme can indicate a flashing yellow illumination of the LED ring to indicate to a user that the trigger should be released. If the fire button is depressed for a length of time less than a threshold indicating a stuck fire button when the jaw assembly is in an open state or when the device is ready to fire, the light control scheme can indicate a flashing yellow illumination of the LED ring indicating that the fire button should be released.

The light control scheme can further include a fourth indicia comprising a solid yellow illumination of the LED ring to indicate further user intervention is desired to continue a stapling operation. For example, if a reload shaft assembly is installed that is not recognized by the control system is installed or if a motor current above a predetermined high threshold is encountered during jaw closure (indicating the presence of overly thick or dense tissue or other items such as clips in the grasped specimen), or a reload shaft lockout is engaged, the light control scheme can illuminate the LED ring with a solid yellow color.

The light control scheme can further include additional indicia indicating certain instances indicating the handle assembly is operating normally. For example, in certain embodiments, the light control scheme can illuminate the LED ring solidly blue to indicate tissue has been grasped and the jaw assembly latched in preparation for a firing operation. The light control scheme can illuminate the LED ring flashing blue if the jaw assembly is subsequently unlatched. The light control scheme can illuminate the LED ring flashing green if a firing operation is canceled.

Control Unit

As previously discussed with respect to certain features of the illustrated handle assembly, the handle assembly can further comprise a control unit. As illustrated, the control unit can comprise a microcontroller electrically coupled to a circuit board to which various additional sensor, power supply, and user display components are electrically coupled. The control unit can be configured to drive the motor to provide open-to-clamp functionality followed by staple firing functionality at a stapler jaw assembly. The control unit can additionally be configured to modify the operational parameters of the motor based on sensory data from one or more of: a motor load sensor, an actuation rack position sensor, a shaft recognition sensor, and an articulation position sensor.

Figure 45A:
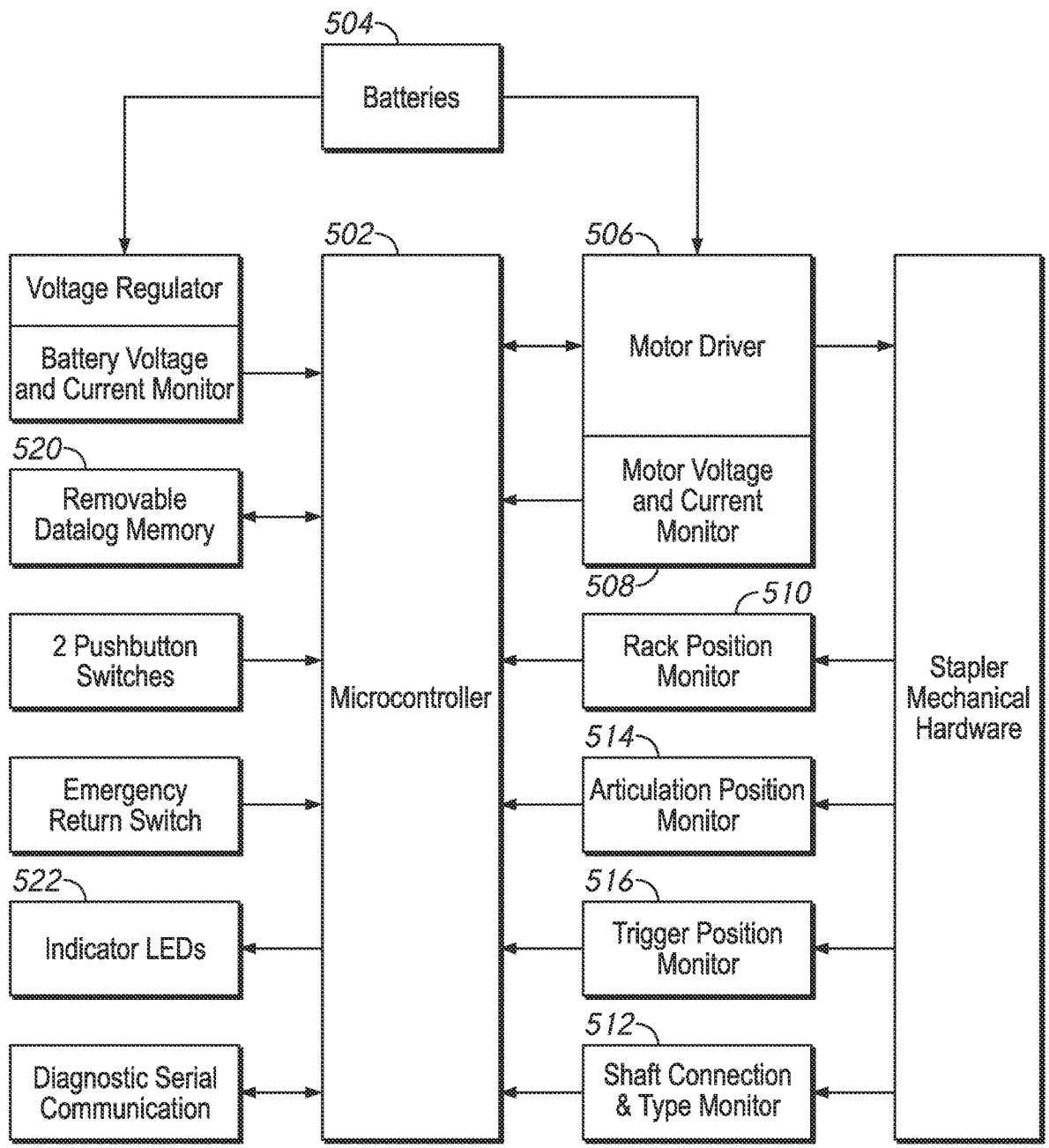
FIG. 45A is a block diagram of information and power flow for an embodiment of control system for the powered handle of FIG. 2.

With respect to FIG. 45A, a schematic flow diagram indicating data and power flow for an exemplary control system for a powered handle is illustrated. In the illustrated flow diagram, the control system comprises the illustrated microcontroller 502. In various embodiments, the microcontroller can comprise an application specific integrated circuit or a general purpose microcontroller running application specific firmware and/or software. As illustrated, the microcontroller receives power and data regarding battery status from the batteries 504 in the power supply. The microcontroller further receives data from various mechanical hardware of the stapler such as a motor driver 506 and current monitor 508, an actuation rack position sensing mechanism 510, and a shaft connection and type monitor 512. As discussed above with respect to the articulation mechanism, the microcontroller 502 can additionally receive articulation position information from an articulation position sensing mechanism 514. The microcontroller can further receive data from a user via a trigger position sensor 516, and pushbutton switches. The control system can output a control signal to actuate the drive system of the powered handle through a motor driver 506. The control system can also output certain operational parameter information to a memory module 520, which, in certain embodiments, can comprise a removable module, and can output certain data for user viewing through LED lights 522 on the handle, such as the light ring user display discussed herein. In some embodiments, the control system can be configured to provide haptic feedback to a user such as by actuation of a separate haptic module or by actuation of a haptic generation motor drive profile that can direct rotation of the motor one or more small displacements in forward and reverse directions, such that a user would feel a feedback sensation but the position of the actuation rack would not be significantly affected. In some embodiments, the microcontroller can be configured to transmit and receive information wirelessly, such as, for example over a Bluetooth, WiFi, or another wireless protocol.

In certain embodiments, the control system is also configured to further define operational parameters of the powered handle. For example, by querying a memory module on the power supply or on the control system itself, the control system can detect whether the powered handle has been used for more than a single procedure. In some embodiments, the stapling system is designed for use in a single procedure and is not designed for resterilization. Additionally, the control system can also query the memory modules on the power supply or the control system to detect a number of staple firings to assess whether sufficient battery power remains to complete an additional firing.

In certain embodiments, the control system can comprise one or more modules directed to certain aspects of powered handle operation. For example, the control system can comprise a shaft recognition module such as is discussed with reference to FIGS. 19B-19K that is configured to recognize certain reload shaft characteristics and apply a corresponding control signal to the motor. In certain embodiments, the control system can comprise a lockout control module that can be arranged to detect when a jaw assembly lockout has been actuated, such as is discussed with reference to FIGS. 47-53. Moreover, the control system can comprise a light control scheme for a light ring display such at is described with reference to FIGS. 42-44 configured to provide visual indicia to a user when certain operational conditions have been encountered.

In certain embodiments, the control system is configured to detect tissue having characteristics that are conducive to staple formation. In certain embodiments, the control system is configured to detect tissue characteristics that can prevent staple firing. In some embodiments, the control system can monitor position, velocity, and supplied torque of the motor in the drive system. The control system can detect whether excessive torque is required to close the jaw assembly, if excess time is needed to close the jaw assembly, or if the jaws are closing at a low speed. These conditions may indicate that the tissue in the jaw assembly is too thick or too dense for the stapler to be effective. In certain embodiments, the control system can monitor the position of the actuation shaft with respect to time and evaluate this monitored position and time with respect to a baseline 'zero load' time reference position and time to assess the tissue characteristics such as thickness and density. In instances where the drive system exceeds predetermined operational parameters, the control system can indicate an error condition and stop a firing operation.

Figure 45B:
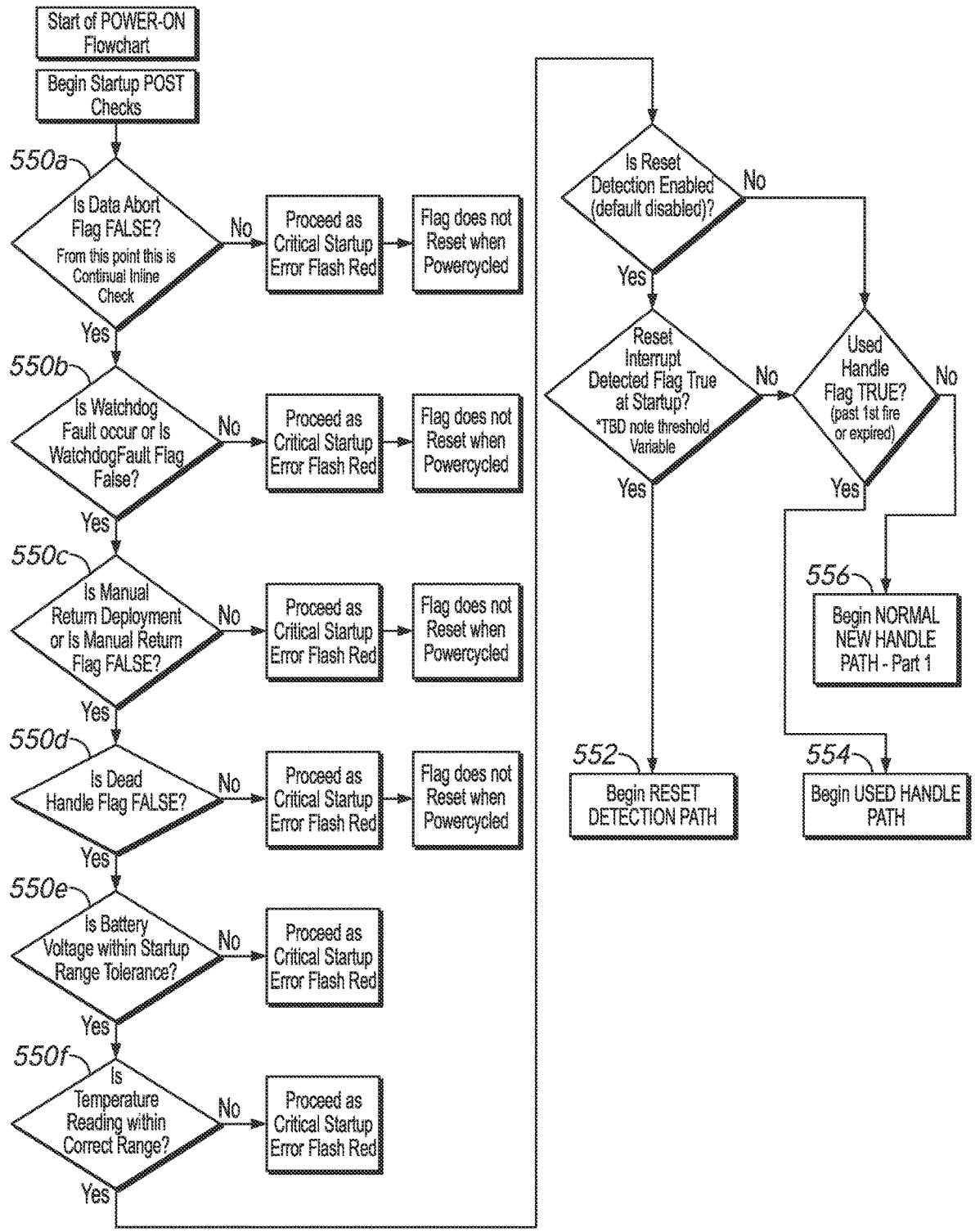
FIG. 45B is a block diagram of a process flow for an initiation portion of an embodiment of a startup module of the control system for the powered handle of FIG. 2.

With reference to FIGS. 45B-45F, in certain embodiments, the control system can comprise an initialization or startup module. The startup module can verify that certain operational parameters of the handle assembly hardware, microcontroller, and memory are at predetermined values or within predetermined ranges before the control system enables the handle assembly to operate in a grasping and firing operation. FIG. 45B illustrates a process flow sequence for one example of an initiation portion of a startup module for the control system. The initiation portion can be run by the control system initially upon a power up of the handle assembly. In use, a power up operation can occur upon the first time a new handle assembly is powered on, when a handle that has previously been used has been powered on, or if a handle assembly experiences a loss of power during an operational sequence. In the illustrated example of process flow sequence, upon assessment of certain initial parameters, the initial portion of the startup module enters one of a new handle submodule, a used handle submodule, or a reset detected submodule.

With reference to FIG. 45B, upon powering on, the initiation portion of the startup module is executed by the microcontroller. The initiation portion queries operational parameters 550a-550f of the handle assembly. In various embodiments, the operational parameters may be stored in a memory register of the microcontroller or a memory module on the printed circuit board. In the illustrated example, the operational parameters 550a-550f can indicate that the handle has previously encountered a hardware or control system fault that could hinder operation of the handle assembly. For example, in the illustrated process flow, the operational parameters comprise stored values for certain defined operational conditions: a data abort flag 550a, a watchdog fault flag 550b, a manual return flag 550c, a dead handle flag 550d, battery voltage within a predetermined range 550e, and a microcontroller temperature within an operational range 550f. If any of the queried operational parameters 550a-550f do not return an operational value or a value within an operational range, the initiation portion of the startup module configures the control system to a critical startup error state. The operational parameters for battery voltage 550e and microcontroller temperature 550f can be reset in a subsequent power cycle, but the various flags representing hardware or control system faults in the other operating parameters 550a-550d are stored during subsequent power cycles.

With reference to FIG. 45B, provided that the queried operational parameters 550a-550f have all returned operational values, the initiation portion assesses the status of the handle and selects a corresponding submodule of the startup module to execute. The control system is configured with a reset detection module to detect a power reset occurrence and store a true value in a memory location if a reset has been detected. The PCB can comprise a reset detection line electrically coupled to the control system. In the illustrated process flow, this reset detection module can be disabled by the control system. Thus, the initiation portion of the startup module assesses whether the reset detection module is enabled. If the reset detection module is enabled, the initiation portion queries a reset detection flag value to assess whether the handle assembly is powering on following a transient power condition that may have been caused by a brief power interruption to the microcontroller or ambient electromagnetic interference. If the stored value for a reset detection flag indicates that a reset has occurred, the reset detected submodule 552 is selected for execution. If the reset detection module is disabled or if the queried flag of the reset detection module indicates no reset has occurred, the initiation portion queries a stored value representing whether the handle has been previously used. If the stored value indicates the handle has been previously used, used handle submodule 554 of the startup module is selected. If the stored value indicates that the handle has not been previously used, the new handle submodule 556 is selected.

Figure 45C:
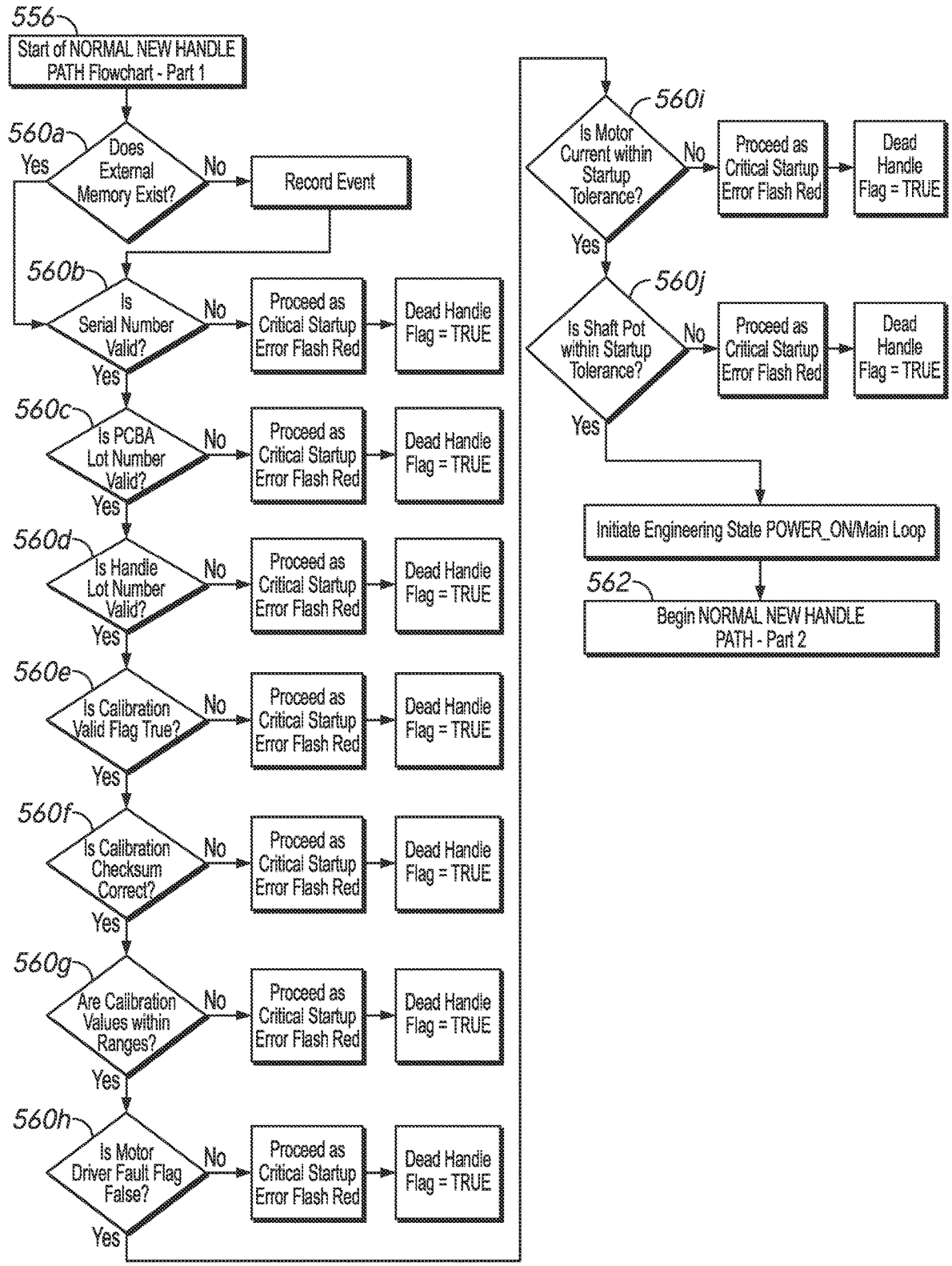
FIG. 45C is a block diagram of a process flow for a first portion of a new handle submodule for an embodiment of startup module for the control system for the powered handle of FIG. 2.

With reference to FIG. 45C, one example of a process flow of a first portion for a new handle submodule 556 is schematically illustrated. In the first portion, the new handle submodule queries various operational parameters to assess whether the handle hardware and control system are in condition for operation. In the illustrated example, the new handle submodule can identify the presence of an external memory module 560a, recording a value if none is present. The new handle submodule can query operational parameter values to authenticate the handle device, including a valid device serial number 560b, a printed circuit board assembly (PCBA) lot number 560c, and a handle lot number 560d. If any of these operational parameters are not valid, the new handle submodule can set a critical startup error state in the control system and can set a dead handle flag value to true such that the handle can not be power cycled and restarted (as an indication of dead handle flag having a true value when queried during the initial portion of the startup module will arrest a startup operation). The new handle module can then verify certain hardware and control system operational parameters including verifying that the device is properly calibrated 560e, 560f, 560g, that the motor is operational 560h, 560i, and that a sensor for the actuation shaft position is within a startup range 560j. If any of these operational parameters are not valid, the new handle submodule can set a critical startup error state in the control system and can set a dead handle flag value to true such that the handle can not be power cycled and reused. Provided that the queried operational parameters 560a-560j are all at operational values or within operational ranges, the new handle submodule sets a powered on operational state in the control system and initiates a second portion 562 of the new handle submodule.

Figure 45D:
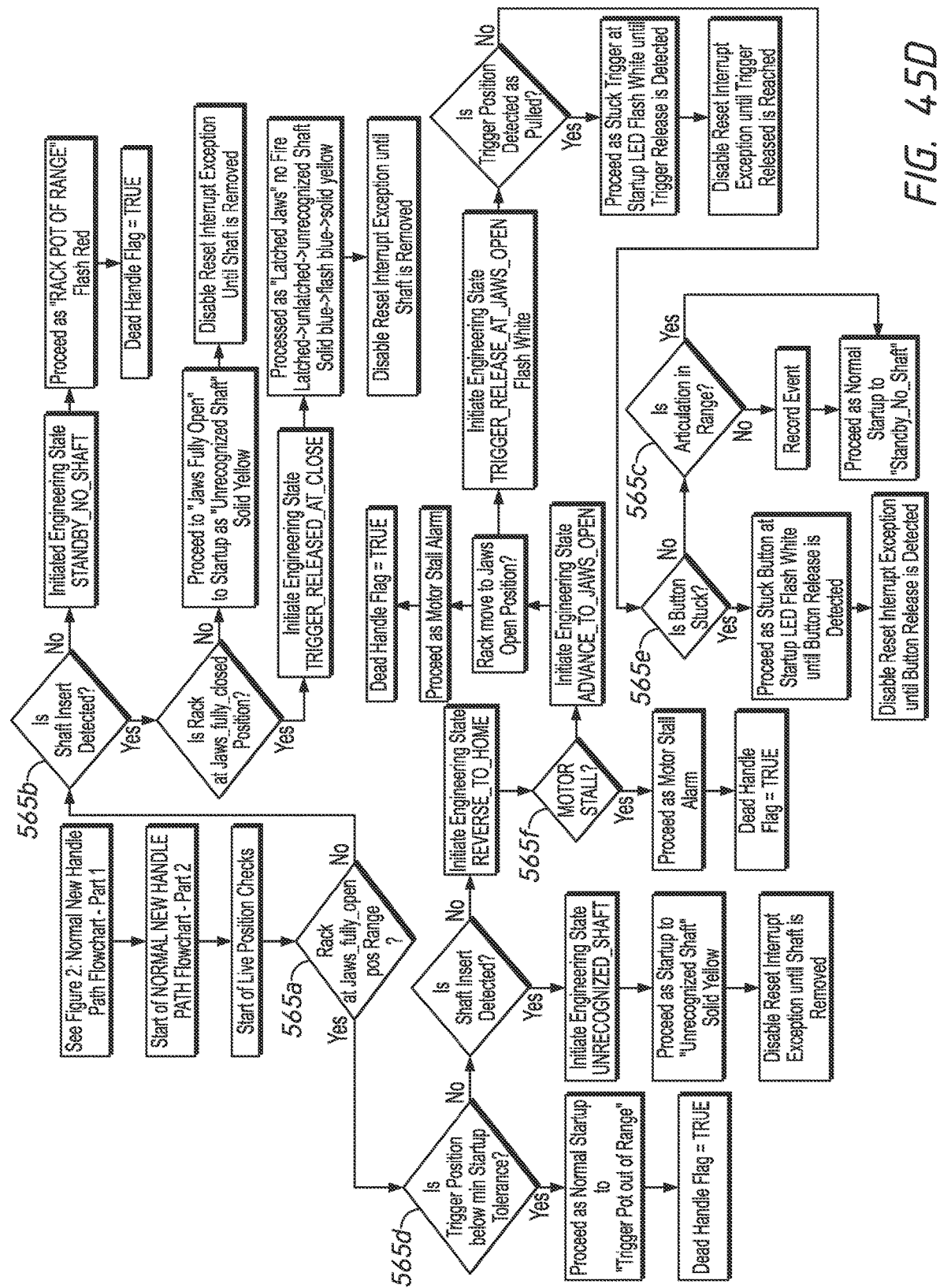
FIG. 45D is a block diagram of a process flow for a second portion of a new handle submodule for an embodiment of startup module for the control system for the powered handle of FIG. 2.

With reference to FIG. 45D, an example of a process flow for the second portion 562 of the new handle submodule is illustrated. In the illustrated example, in the second portion 562, the new handle submodule queries the position of the actuation shaft 565a, shaft recognition module 565b, articulation sensor 565c trigger 565d and firing button 565e and motor operational characteristics 565f to verify that the handle is in an operational state. If certain position values or combinations of position values are returned when the second portion of the new handle submodule executes position queries, the new handle submodule can identify certain hardware failures such as trigger and actuation shaft position failures, or motor stall failures and can determine whether an unrecognized reload shaft has been installed to the handle.

Figure 45E:
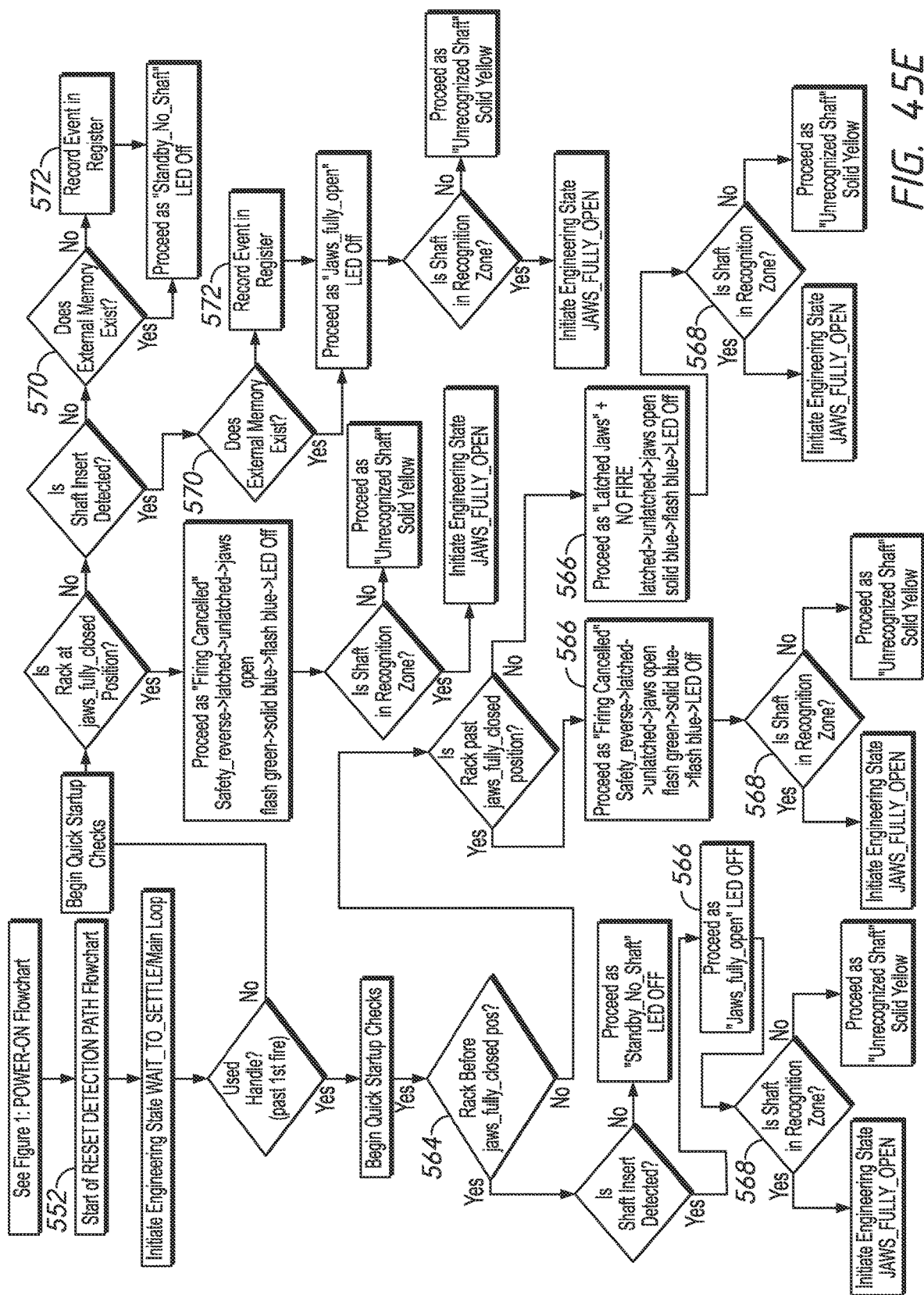
FIG. 45E is a block diagram of a process flow for a reset detected submodule for an embodiment of startup module for the control system for the powered handle of FIG. 2.

With reference to FIG. 45E, an example of a process flow for the reset detected submodule 552 is illustrated. In the illustrated example, if a reset has been previously detected, the reset detected submodule initially queries whether the handle has previously completed a first firing and thus has a used handle operational parameter. If the handle has previously been fired, the reset detected submodule queries a position of the actuation shaft to determine a position of the actuation shaft rack 564: assessing whether it is positioned such that the jaws are fully closed, open or partially closed, or advanced beyond the fully closed position. The reset detected submodule then returns the actuation shaft to a position corresponding to jaws open 566. The reset detected submodule then queries the shaft recognition module to assess whether a recognized reload shaft is coupled with the handle assembly 568. If the handle has not been previously fired, the reset detected submodule 552 executes a similar process flow to determine a position of the actuation shaft, return the actuation shaft to a position corresponding to jaws open, then query whether a recognized reload shaft is coupled to the handle assembly. In certain conditions, the reset detected submodule 552 can further query whether an external memory is present 570 and record an event 572.

Figure 45F:
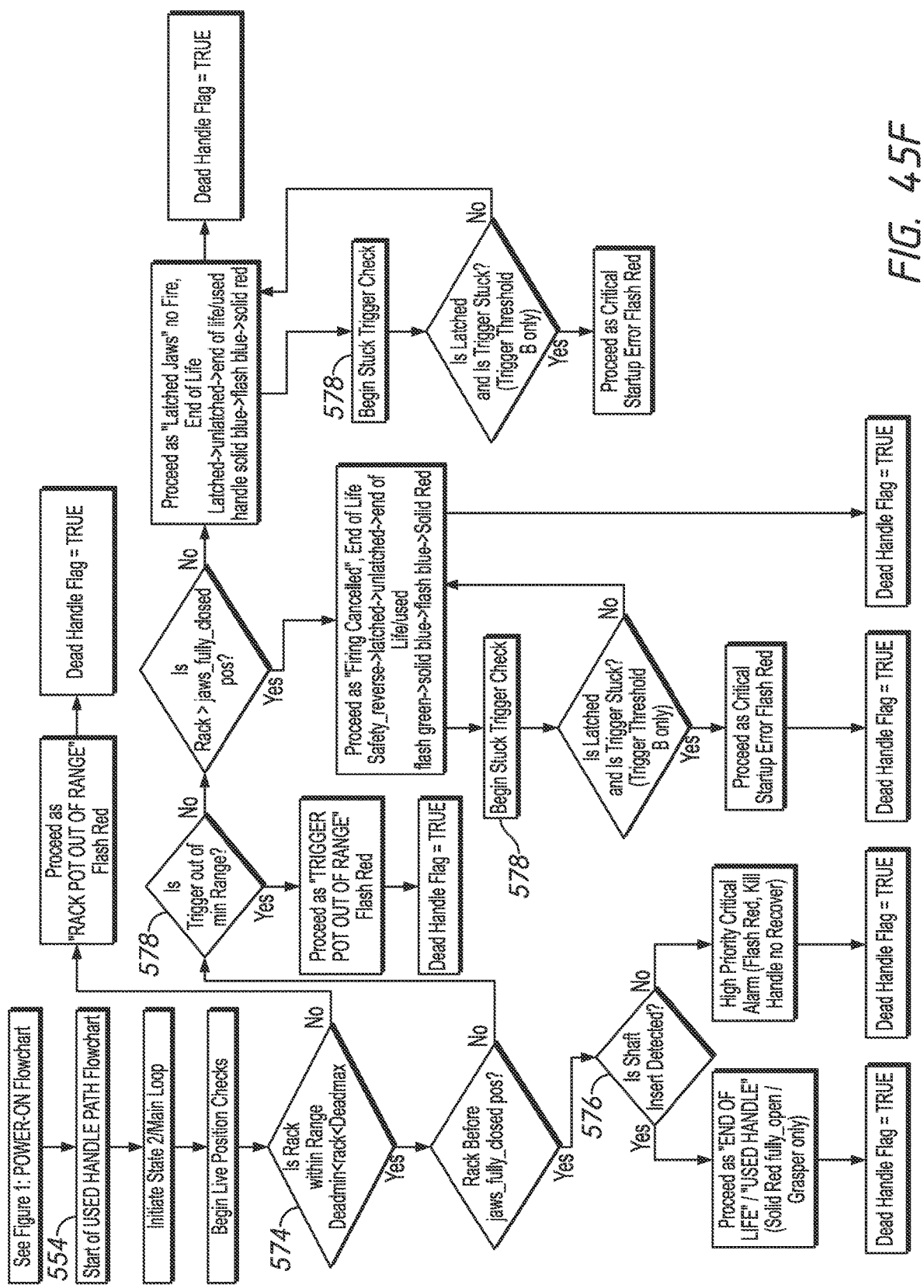
FIG. 45F is a block diagram of a process flow for a used handle submodule for an embodiment of startup module for the control system for the powered handle of FIG. 2.

With reference to FIG. 45F, an example of a process flow for the used handle submodule 554 is illustrated. Where a used handle has been detected, the In the illustrated example, the used handle submodule queries the position of the actuation shaft 574, shaft recognition module 576 and trigger 578 to verify that the handle is in an operational state. If certain position values or combinations of position values are returned when the used handle submodule executes position queries, the used handle submodule 554 can restrict operation of the handle assembly and set a dead handle flag as true.

Figure 46A:
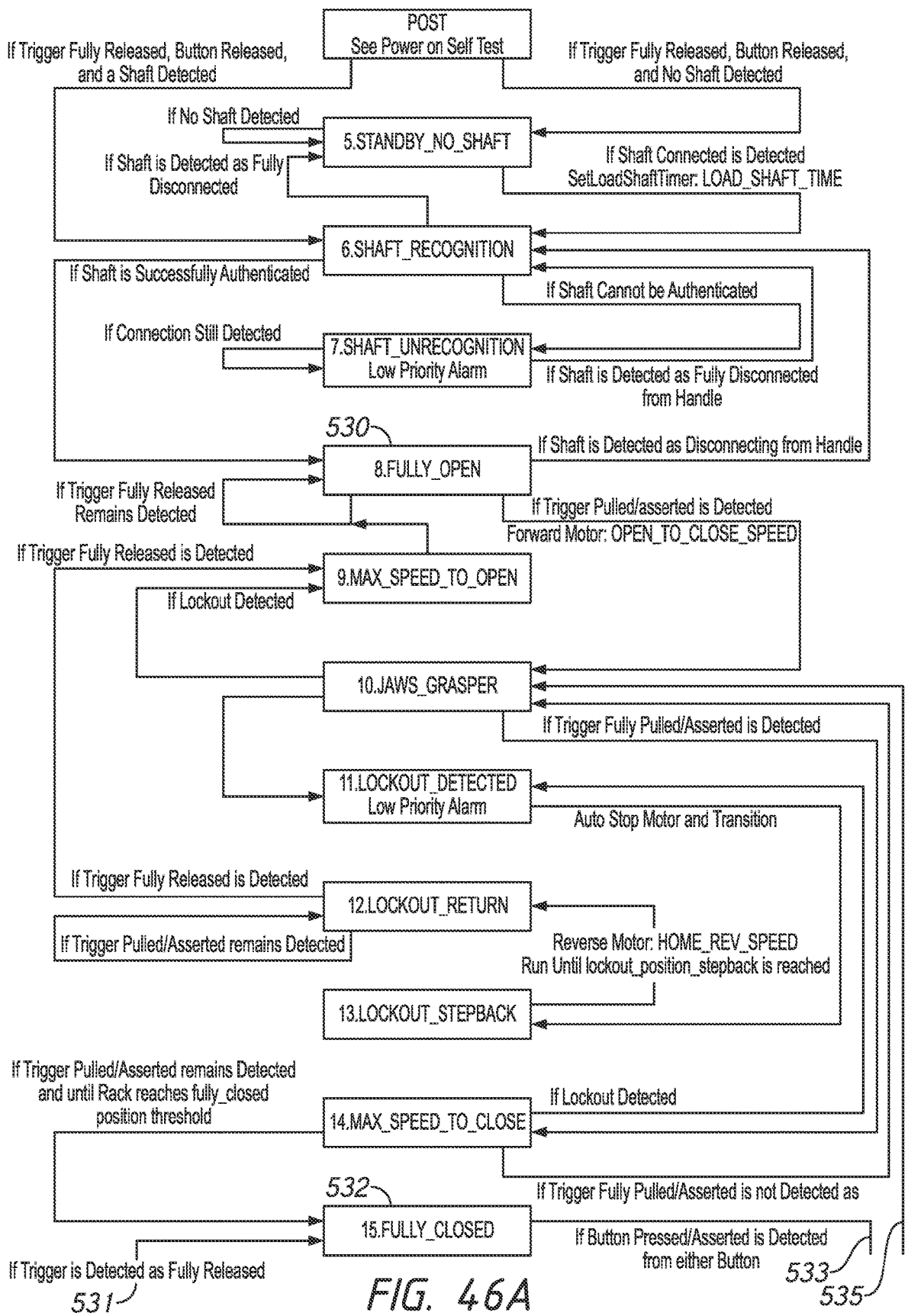
FIGS. 46A and 46B are an operational sequence flow chart for an exemplary operational sequence of the powered handle of FIG. 2.
Figure 46B:
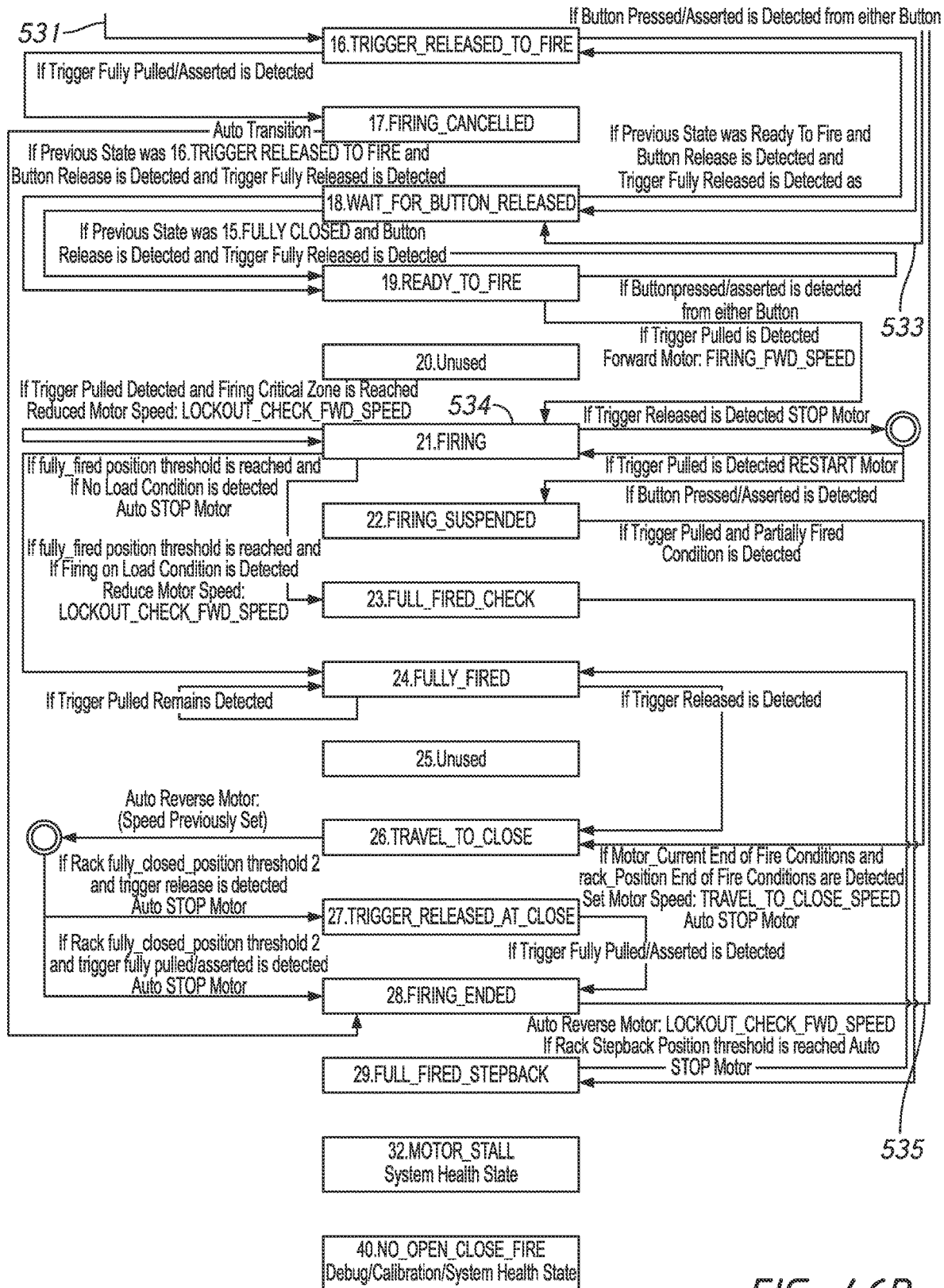

With reference to FIGS. 46A and 46B, a block diagrams of an operational flow chart for an exemplary firing sequence of the control system is illustrated. As illustrated, the control system integrates user inputs from the trigger and firing button as well as hardware inputs from various sensors and monitors to advance the jaw assembly from a fully open condition 530 to a fully closed condition 532 to a firing sequence 534, then back to the fully open condition 530. FIG. 46A illustrates the operational flow chart from an initial powered on condition to a jaws fully closed condition. FIG. 46B illustrates the operational flow chart from the jaws fully closed condition through a firing sequence. With the jaws in a fully closed state 532, the control system can detect whether the trigger is fully released 531 in one illustrated operational sequence. With the jaws in a fully closed state, the control system can detect whether a firing button has been pushed 533 in another illustrated operational sequence. Upon completion of a firing sequence, the control system can return 535 the handle assembly to a grasping configuration.

During a firing operation, the control unit can monitor a position of the actuation shaft to provide and provide a desired motor drive profile. In certain embodiments, the microcontroller can operate using a motor drive logic profile that identifies various operational zones of the actuation rack position and can apply predetermined motor drive parameters, such as, for example motor speed, and motor load monitoring, for each of these zones and for various actuation rack positions within these zones. In certain embodiments, the motor drive logic profile can be a software or firmware based computing program stored in a memory module such as computer readable media in or electrically coupled to the control unit. In certain embodiments, the motor drive logic profile can define operational parameters for and an operational sequence through one or more of: a grasper zone, a lockout zone, a firing zone, a full fired zone, a returning zone, and an opening zone. In certain embodiments, the motor drive logic profile can be configured to adjust zones and certain positions associated therewith responsive to sensor input received from one or more of the articulation position sensor, the shaft recognition sensor, the motor load monitor, or other sensor input.

The grasper zone corresponds to a zone of movement of the actuation rack between a jaws open position and a jaws clamped position of an attached end effector on an instrument shaft. In this region, the microcontroller can be configured to drive the jaw assembly proportionally to the degree of trigger movement input by the user and transmitted to the microcontroller by a trigger position sensor such as a trigger potentiometer. If the trigger is fully depressed, the device will advance the actuation shaft to position the jaws of the end effector in a fully closed position. If the trigger is fully released, the device will return to jaws open. Fully pulling the trigger while simultaneously pressing the firing button will advance the actuation shaft to the lockout zone. In other embodiments, in the grasper zone, the microcontroller can be configured to drive the motor at a rate proportional to the angle of trigger displacement, such that rather than the amount of jaw closure being defined by trigger movement, the speed of jaw closure in the grasper zone would be defined by trigger movement.

In certain embodiments, the motor speed can be varied through pulse width modulation to a desired travel speed for a particular zone. In certain embodiments, the motor can be pulse width modulated at a duty cycle less than 100% for the grasper zone. In certain embodiments, it can be desirable to drive the motor at a duty cycle between approximately 50% and 90% in the grasper zone. In certain embodiments, the motor drive logic profile can be configured such that the motor is pulse width modulated at a 70% duty cycle in the grasper zone.

In certain embodiments of control system, from a jaws closed position in the grasper zone, if a user depresses a firing button on the handle, the control unit will advance to the lockout zone of the motor drive logic profile. The lockout zone can be configured to provide a motor control profile for an instrument shaft and jaw assembly that includes a firing lockout to prevent a firing actuation of the stapler if either a fired stapler reload cartridge is present or no stapler reload cartridge is present. Operation of this type of lockout can result in significantly increased loading of the motor as a portion of the firing mechanism in the instrument shaft or jaw assembly is prevented from advancing further at a predetermined actuation position of the actuator. Accordingly, during the lockout zone, the control unit can monitor sensor information from the actuator rack position sensor and a motor load sensor for an expected spike in motor load.

In certain embodiments of control system, rather than incorporating a separate lockout zone, the control system can monitor for the presence of a lockout when the handle assembly is in the grasper zone. Accordingly, in certain embodiments, the control system does not include a dedicated grasper zone, but continuously monitors for the presence of a lockout during the grasping zone. Such an embodiment of control system can facilitate indication of the presence of a lockout having distinct missing and used reload mechanisms as discussed with reference to FIGS. 33-41.

Lockout Control Module

As discussed, in certain embodiments, the control system can be configured to monitor current within a defined 'lockout zone' of actuator position. In these embodiments, the control system can rely solely on a current threshold to determine the presence of a lockout mechanism engagement. In certain embodiments, the current threshold was determined based off a sample at the beginning of the lockout zone plus a constant 300 mA, indicating that a reload lockout had not been defeated and travel of the actuator had been arrested. However, this one factor lockout sensing module of the control system is most effective outside of the grasping region as the actuator is entering a firing stroke of the jaw assembly. Outside the grasping region, the control system directs constant pwm operation of the motor. Moreover, when the actuator had been advanced distally beyond the grasping region, tissue clamping had already occurred, so any potential current fluctuations attributable to tissue thickness and consistency variations would be minimized. However, the two-position lockout mechanisms described above with reference to FIGS. 32-41 can require further refinement of lockout detection modules of the control system as they provide certain operational advantages when the lockout mechanisms are engageable within the grasper zone.

As discussed above with respect to FIGS. 32-41, the two-position lockout mechanisms can desirably engage at two distinct actuator positions corresponding to an empty jaw assembly and an at least partially fired reload. In some embodiments, these locked out actuator positions are relatively close to one another as lockout notches formed in the firing beam can be substantially contiguous. Moreover, in certain embodiments, each of these actuator positions can fall within the grasping zone or region of control system operation. In the grasping region, the control system can be configured to provide a user full control over the opening and closing of the jaws of the jaw assembly prior to entering a firing state. The user can partially close the jaws, re-open, and re-close without limit. In certain embodiments, in the grasping region, the trigger is mapped to proportional jaw closure, which means pulling the trigger 25% will result in 25% jaw closure. However, every time the user pauses, opens, or closes the jaws, the motor stops and restarts. It takes additional power for the motor to overcome inertia and ramp up to full speed, resulting in a large momentary current spike. Moreover, as the jaw assembly typically compresses tissue during jaw closure in the grasping region, the load on the motor can be elevated in response to thicker or denser tissues positioned between the jaws. Accordingly, in some instances, a lockout module in the control system based on current detection alone can lead to false positive indications where one or more lockout mechanisms can engage at an actuator position in the grasper region due to transient user input and tissue compression conditions.

Figure 47:
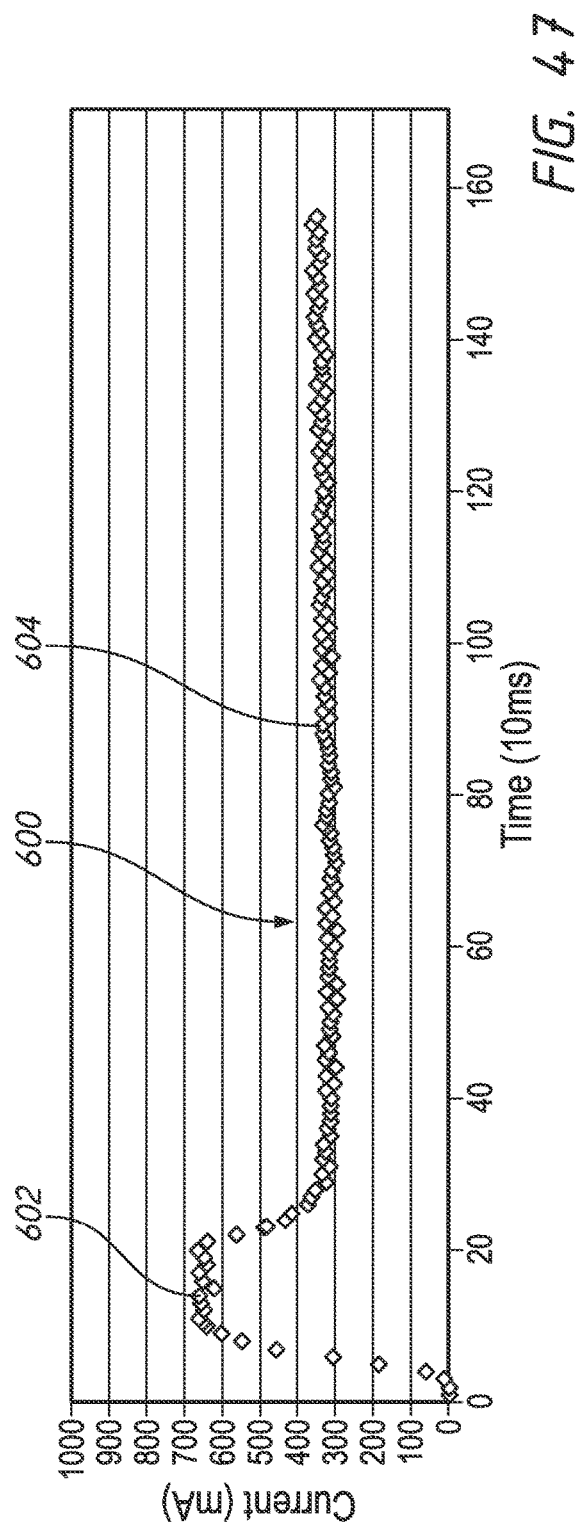
FIG. 47 is a plot of motor load versus elapsed time for one exemplary jaw assembly in a grasping operation for a powered handle such as the powered handle of FIG. 2.
Figure 48:
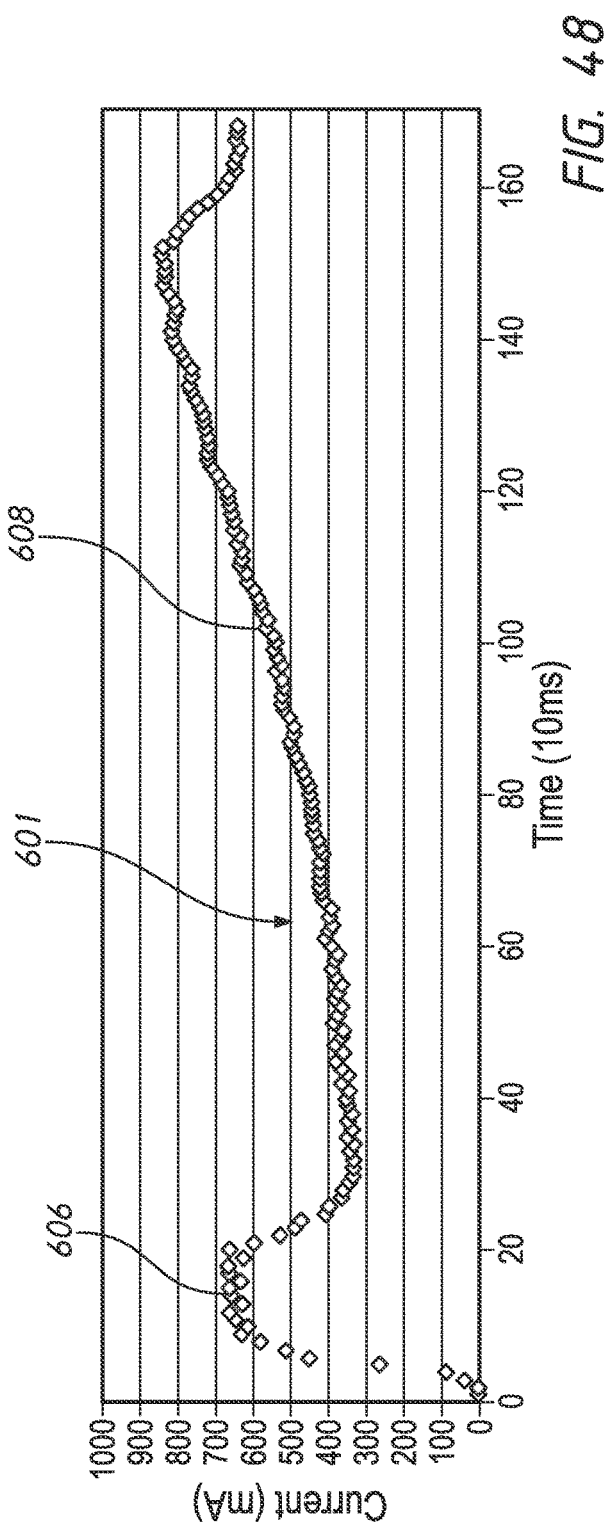
FIG. 48 is a plot of motor load versus elapsed time for one exemplary jaw assembly in a grasping operation for a powered handle such as the powered handle of FIG. 2.

With reference to FIGS. 47-52 plots of an exemplary current profile 600, 601, 603, 605, 607, 609, 611 for various operational conditions of a powered stapler are illustrated. The plot illustrates motor load or current draw (measured in milliamps) tracked over time, measured in tens of milliseconds, of operation. In FIG. 47, a plot 600 of an exemplary current profile is illustrated for the grasper region of the stapler with no load (representing, for example, a substantially empty jaw assembly during the grasping operation). The plot includes an initial spike 602 in current as the trigger is first pulled and the motor accelerates, then a subsequent region of relatively constant current 604 as the motor operates at a relatively constant speed. In FIG. 48, a plot 601 of an exemplary current profile is illustrated for the grasper region of the stapler with a relatively high load (representing, for example, a jaw assembly grasping a relatively high thickness tissue specimen during the grasping operation). The plot includes an initial spike 606 in current as the trigger is first pulled and the motor accelerates, then a subsequent region of increasing current 608 as the motor operates at a relatively constant speed compressing tissue grasped by the jaw assembly.

Figure 49:
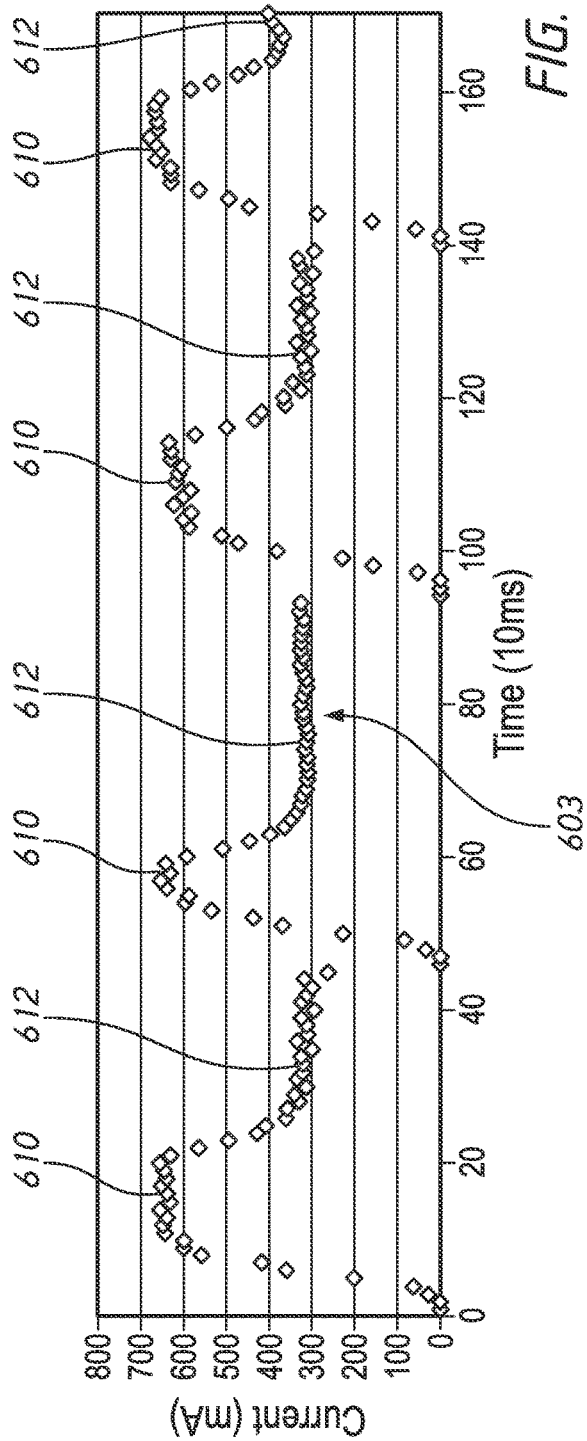
FIG. 49 is a plot of motor load versus elapsed time for one exemplary jaw assembly in a grasping operation with multiple trigger actuations for a powered handle such as the powered handle of FIG. 2.

In FIG. 49, a plot 603 of an exemplary current profile is illustrated for the grasper region of the stapler with repeated depressions of the trigger (representing, for example, a jaw assembly being actuated by multiple applications of the trigger during the grasping operation). The plot includes several spikes 610 in current as the trigger is repeatedly pulled and the motor accelerates, then, for each spike 610, a corresponding subsequent region of relatively constant current 612 as the motor operates at a relatively constant speed compressing tissue grasped by the jaw assembly.

Figure 50:
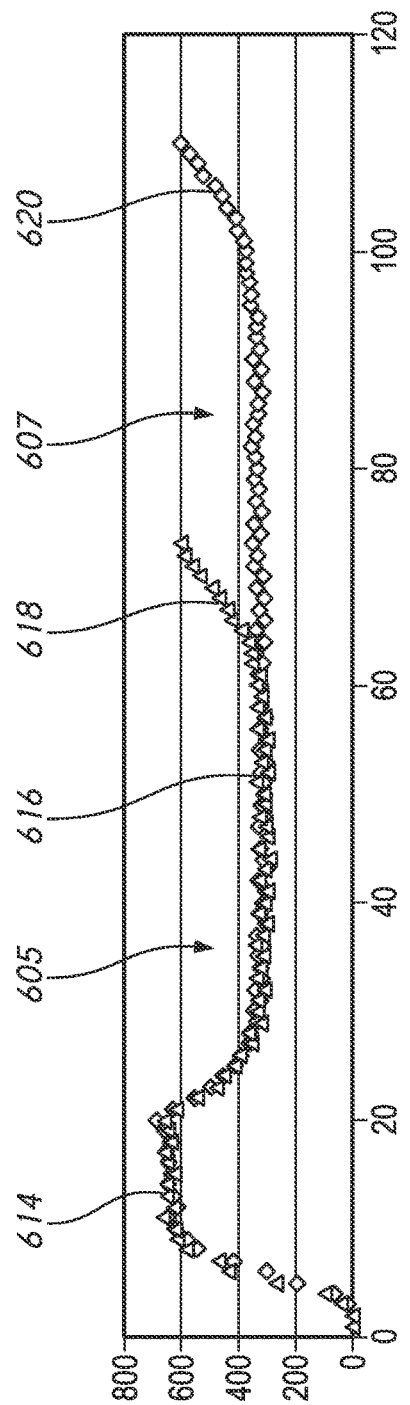
FIG. 50 are plots of motor load versus elapsed time for one exemplary jaw assembly in a grasping operation in which lockout mechanisms are encountered for a powered handle such as the powered handle of FIG. 2.

In FIG. 50, plots of an exemplary current profile are illustrated for the grasper region of the stapler with no reload cartridge present 605 and a partially fired reload cartridge present 607. The plots each include an initial spike 614 in current as the trigger is initially pulled and the motor accelerates, a subsequent region of relatively constant current 616 as the motor operates at a relatively constant speed compressing tissue grasped by the jaw assembly, and an increasing region in current as a missing reload lockout 618 is encountered and, in another plot, as a partially fired reload lockout 620 is encountered. It is noted that this increasing region has a slope that is distinct from the slope of the initial spike and that falls within a distinct range such that a lockout module of the control system can monitor a current of the motor to detect the presence of motor current indicating a slope in this distinct range.

Figure 51:
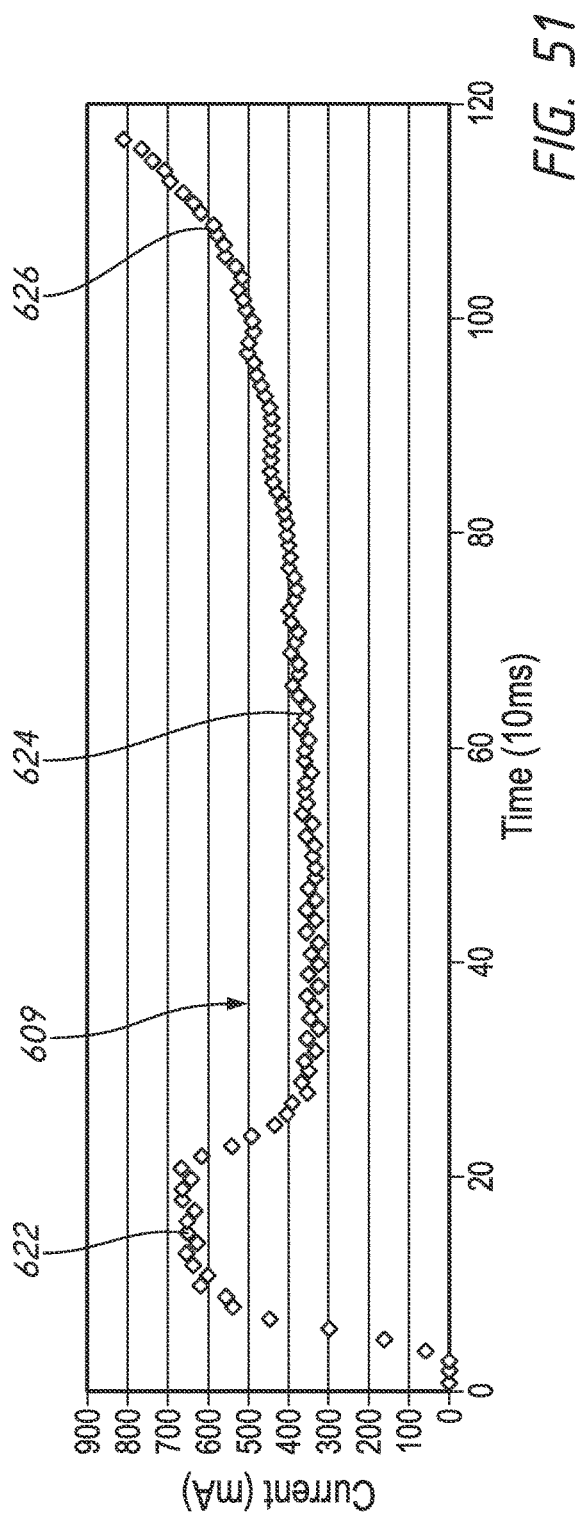
FIG. 51 is a plot of motor load versus elapsed time for one exemplary jaw assembly in a grasping operation in which a lockout mechanism is encountered for a powered handle such as the powered handle of FIG. 2.

In FIG. 51, a plot 609 of an exemplary current profile is illustrated for the grasper region of the stapler with a partially fired reload present and a relatively high load (representing, for example, a jaw assembly grasping a relatively thick tissue specimen and having a partially fired or used reload cartridge installed in the jaw assembly). The plot 609 includes an initial spike 622 in current as the trigger is pulled and the motor accelerates, then a subsequent region of gradually increasing current 624 as tissue is grasped and compressed by the jaw assembly. Finally, the plot includes an increasing region 626 as the partially fired reload lockout is encountered. It is noted that a slope of the increasing region 626 is distinct from both the initial spike 622 and the region of gradually increasing current 624.

Figure 52:
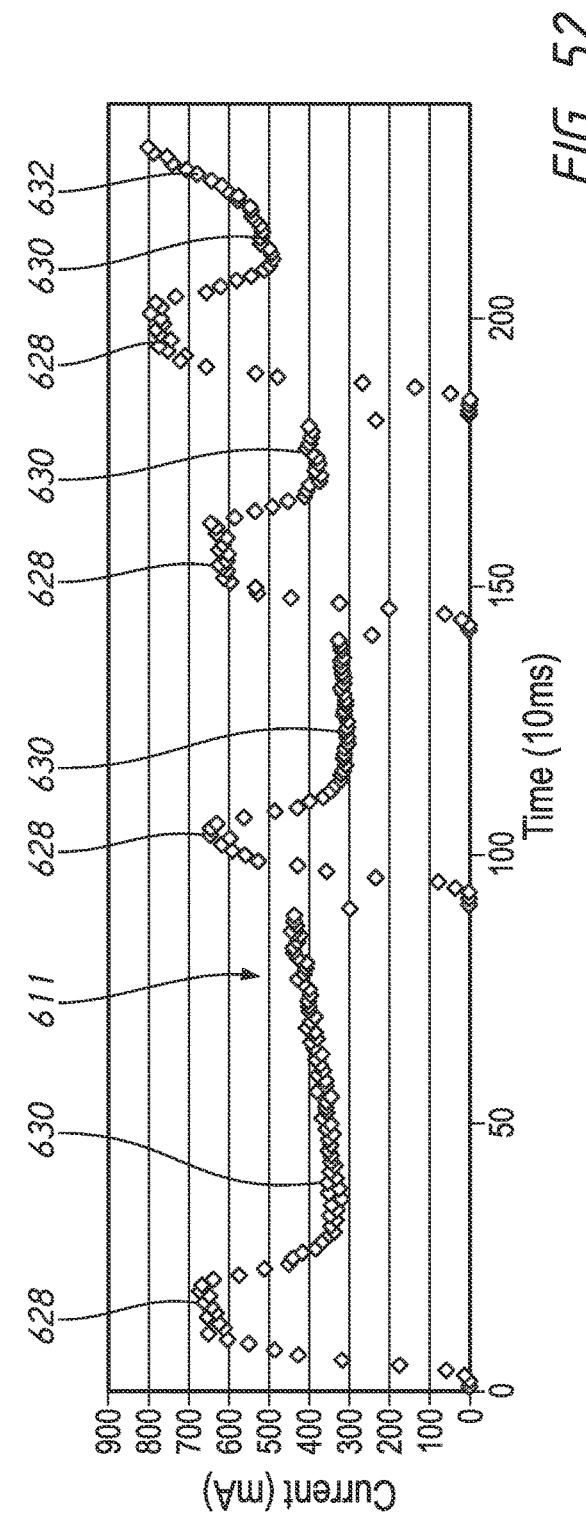
FIG. 52 s a plot of motor load versus elapsed time for one exemplary jaw assembly in a grasping operation with multiple trigger actuations in which a lockout mechanism is encountered for a powered handle such as the powered handle of FIG. 2.

In FIG. 52, a plot 611 of an exemplary current profile is illustrated for the grasper region of the stapler with repeated depressions of the trigger, a relatively high load, and a partially fired reload present (representing, for example, a jaw assembly being actuated by multiple applications of the trigger during the grasping operation, the jaw assembly grasping a relatively thick tissue specimen, and having a partially fired or used reload present in the jaw assembly). The plot 611 includes several spikes 628 in current as the trigger is repeatedly pulled and the motor accelerates, then, following a spike 628, a corresponding subsequent region of gradually increasing current 630 as the motor operates to compress tissue grasped by the jaw assembly. Finally, the plot includes an increasing region 632 as the partially fired reload lockout is encountered. Again, it is noted that the slope of the increasing region 632 is distinct as compared to the initial spikes 628 and the regions of gradually increasing current 630.

It is noted that the loads experienced and position detected can vary based on the size and configuration of the elongate shaft, jaw assembly, and lockout mechanisms in addition to the specifications of the motor, battery, and gearing. Thus, the plots of FIGS. 47-52 are merely illustrative of performance of certain embodiments of powered stapler. Despite the differing lockout locations and nominal current draws, the slope of the current profile when a lockout condition engages appears consistent between all tests.

In terms of lockout conditions that can be monitored by the control system, time and position can be unreliable and their rate of change is inconsistent between different loads that may be generated in a grasping zone of actuator travel. A current threshold alone can be falsely triggered by current draw conditions generated in normal grasper usage, and the voltage varies as the batteries are drained. However, one consistent lockout condition is the slope of the current profile with respect to actuator position as illustrated in FIG. 50, which falls within a distinct acceptance range when a lockout condition is present. Nominal current draw exhibits a lower slope, while grasper usage has a much steeper slope. Except for rare occurrences, a lockout engagement has a unique current vs. time plot that falls between the other cases. A lockout slope acceptance range for a particular configuration of elongate shaft can be calculated by examining the lockout slopes from a large sample size. In certain embodiments, the control system can include a lockout module which monitors the slope of the current draw with respect to actuation shaft position to detect whether a current profile slope falls within the lockout acceptance range, indicating a lockout mechanism has engaged. The lockout module of the control system can be configured to disengage the motor and configure the control system to take further actions discussed with respect to the motor drive profiles of FIGS. 50-52 upon indication of engagement of a lockout mechanism.

In certain embodiments, the lockout module of the control system can be further refined to provide more consistent lockout engagement detection even in cases of transient inconsistencies in the motor draw versus position monitoring that would otherwise indicate a slope corresponding to engagement of a lockout mechanism. In certain instances, the current profile can be prone to instantaneous inconsistencies due to varying tissue density, drivetrain component wear, or delayed data collection. The current can temporarily deviate from the expected slope if one of the gears has a nick or a burr, or if an unusually thick pocket of tissue is compressed. To combat these fluctuations, in certain embodiments of lockout module in the control system, the change in current (slope) can be averaged across a plurality of data entries to display a stable, reliable trend. In some embodiments, the slope of the current profile can be averaged across five data entries. This averaging can delay the detection of a lockout engagement slightly, but the benefit to the false detection rate can outweigh the minor additional forces that the components can endure during this delay period.

As previously mentioned, there are rare occurrences where the slope can coincidentally fall within the acceptance window. One such instance is attributable to transient load conditions around trigger actuation. Following trigger movement, the current profile exhibits a corresponding current spike. At the peak of this spike, the current settles momentarily before decreasing back to nominal. During these few counts of settling, the change in current can occasionally fall within a lockout acceptance range.

In embodiments of lockout module detecting lockout engagement based solely on the current slope or profile, these data points would falsely indicate engagement of a lockout mechanism. Thus, in certain embodiments, the lockout module can be configured to detect a lockout mechanism engagement only upon, a minimum of a plurality of consecutive averages of the current slope falling within the predetermined acceptance range. For example, the lockout module can be configured to detect a lockout mechanism engagement only upon three consecutive averages of the current slope falling within the acceptance range. If the average (of the previous plurality of current slope profiles) is within the lockout acceptance range, the control system stores this average and upon the next data acquisition by the control system (which, in certain embodiments, is 10$ms$ later), the lockout module will again calculate the average of the previous plurality of current profiles using the new data point (and with the oldest current profile value from the initial plurality of current profiles no longer present in the calculation) and compare this new average to the lockout acceptance range. If three consecutive values fall within the lockout acceptance range, the lockout module can indicate a lockout mechanism has been engaged. If a second or third average does not fall within the acceptance window, the control system can erase any stored averages and continue monitoring for three consecutive current profile adjectives within the predetermined lockout range.

In certain embodiments, the lockout module can be further refined to eliminate transient conditions that could provide false indications of lockout engagement. In certain motor load profiles in the grasping region, current spikes exist which can generate a plurality of consecutive current profile averages within a predetermined acceptance range corresponding to a slope of the current profile empirically determined to be within a lockout engagement region. In certain embodiments, the acceptance range can be between 22.1 and 200 calculated from a current profile with a current draw measured in mA and an actuator position measured in counts in a potentiometer based position sensing mechanism. In other embodiments, the acceptance range can be between 21.1 and 200 calculated from a current profile with a current draw measured in mA and an actuator position measured in counts in a potentiometer based position sensing mechanism. In other embodiments, the acceptance range can have a different range based on different computational units or different handle assembly, shaft assembly, or lockout mechanism configurations. As an initial matter, certain eligibility check criteria can be monitored by the control system to trigger operation of the lockout module. For example, in certain embodiments the control system can periodically collect motor current samples and associated actuation shaft rack position data until enough samples are present for computation of the averages calculated by the lockout module. In certain embodiments, the control system can be configured to collect samples every 10 ms and 6 consecutive samples can be required to be taken to perform the averaging calculations of the lockout module. Once sufficient samples have been collected, the control system can query whether the actuation shaft is at a position indicating a lockout may be present. In certain embodiments, the control system can query the position of the actuation shaft. In other embodiments, the control system can verify that the handle assembly is in a grasper state. In certain embodiments, additional eligibility checks are performed to verify that the current is increasing as the actuation shaft is advancing. The control system can further query whether the motor current of the last collected sample is greater than or equal to the previous two samples and whether the actuation shaft rack position of the last sample is greater to or equal to the previous sample. If all of these eligibility check conditions are met, the lockout module is initiated to evaluate whether the collected samples indicate a lockout has been activated.

In light of the above discussion of certain aspects of detecting lockout mechanism engagement in a grasping region, in some embodiments, the control system can include a lockout module configured to consistently distinguish engagement of a lockout mechanism from other transient load conditions on the motor in the grasping region. In certain embodiments, the control system can periodically monitor motor current, actuator position, and elapsed time, and the lockout module can comprise a series of computer processor implementable instructions embodied in software or firmware to calculate whether the current slope profile is indicative of lockout mechanism engagement. In one embodiment, the lockout module can generally be structured to indicate a lockout has been engaged based on the following criteria:

IF: system is within lockout region
    IF: motor current of test sample is greater than or equal to the previous two samples
    IF: position of actuation shaft is greater than or equal to the previous sample
yn=motor current
$\Delta y_n$=slope=change in current=$(y_n-y_{n-1})$
$X_n$=average of previous 5 $\Delta y$=$[(\Delta y_n+\Delta y_{n-1}+\Delta y_{n-2}+\Delta y_{n-3}+\Delta y_{n-4})/5]$
21.1-200=acceptance range=$21.1 \leq X_n < 200$
Three consecutive values required=$21.1 \leq X_n, X_{n-1}, X_{n-2} < 200$ Upon a determination that three consecutive averaged samples fall within the acceptance range, the lockout module can further assess whether presence of a lockout is indicated by using a bifurcated assessment having different computations depending on whether the motor is being operated at maximum pwm (indicating a fully depressed trigger) or at a pwm lower than maximum pwm.

If during a grasping engagement the trigger is depressed or released, the motor must transition from stationary to full speed. If the motor was instantly instructed to rotate at full speed, the resulting current spike would be large due to the jump in speed. Instead, the current spike can be minimized by controlling the speed of the motor through a ramp up cycle. This control utilizes pwm, or pulse-width modulation. The pwm governs the percentage of power that the motor receives. If the pwm=100, the motor will operate at full speed. If the pwm=50, the motor will operate at 50% of its max speed. By ramping up the pwm in set intervals following trigger movement, the motor more slowly transitions to full speed and any resulting current spike, although still present, is greatly diminished. In certain embodiments, the ramp up profile of a pwm ramp up in the grasping region takes less than 100 ms to complete, so for the majority of the lockout region (which, in certain embodiments can be transitioned in approximately 1.5 seconds), the motor would be operated at maximum pwm.

Upon identifying three consecutive averages within the acceptance range, the lockout module can be bifurcated to apply different assessment criteria depending on whether the motor is operating at maximum pwm or not to account for certain unlikely, but possible usage scenarios. For example, if a user were to pull the trigger just enough to move the actuator within a few position counts of the lockout mechanism and then stop. Upon reengaging the trigger, the user would cause the pwm to ramp up the shaft and jaw assembly would simultaneously physically engage a lockout mechanism. Relying on the lockout module described above during this unstable region would undesirably delay lockout mechanism detection. Instead, in certain embodiments, the lockout module can further comprise a first criteria to identify the presence of a lockout when the motor is operating at maximum pwm and a second criteria to identify the presence of a lockout when the motor is not operating at max pwm to more quickly detect engagement of a lockout mechanism in the above usage scenario.

Following an indication by the lockout module that three consecutive averages fall within the acceptance range, if the lockout module determines if the pwm is at a maximum, which can be identified by the monitored current across position index counts. If so, the lockout module applies a first lockout assessment criteria. If the pwm is determined not to be at a maximum, the lockout module applies a second lockout assessment criteria. This bifurcated control scheme can assess the motor current against a baseline with a correction factor based on anticipated load on the motor under its operational condition. If the pwm is at its max, then grasper functionality is not being utilized so the motor current is expected to be lower. If the pwm is not at its max, then the handle's motor is ramping up so motor current is expected to be higher.

Both assessment criteria for end conditions rely on a baseline current measurement that considers the nominal current draw of the system. As it is desirable that the lockout module of the control system is compatible with an array of handles, shafts, reloads, and tissue densities, the system can define a baseline current for each application of the lockout module to assess whether the current is deviating significantly from nominal. This baseline current measurement is taken at the first instance when the system traveled at max speed, or at max pwm. When at full speed, the current stabilizes to a reliable value which is not impacted by the load as this measurement is taken prior to tissue compression.

In each assessment criteria, a position-dependent current correction value is added to the current baseline to establish the current threshold. This current correction value accounts for the increase in nominal current with position due to clamping and tissue compression occurring later on within the grasping region. Position based current correction values can be empirically determined for a given elongate shaft and lockout mechanism assembly by plotting the max nominal current values at the ideal lockout locations and calculating the linear equation connecting them. These predetermined current correction values can then be stored for use by the lockout module in assessing the presence of a lockout mechanism engagement.

Figure 53:
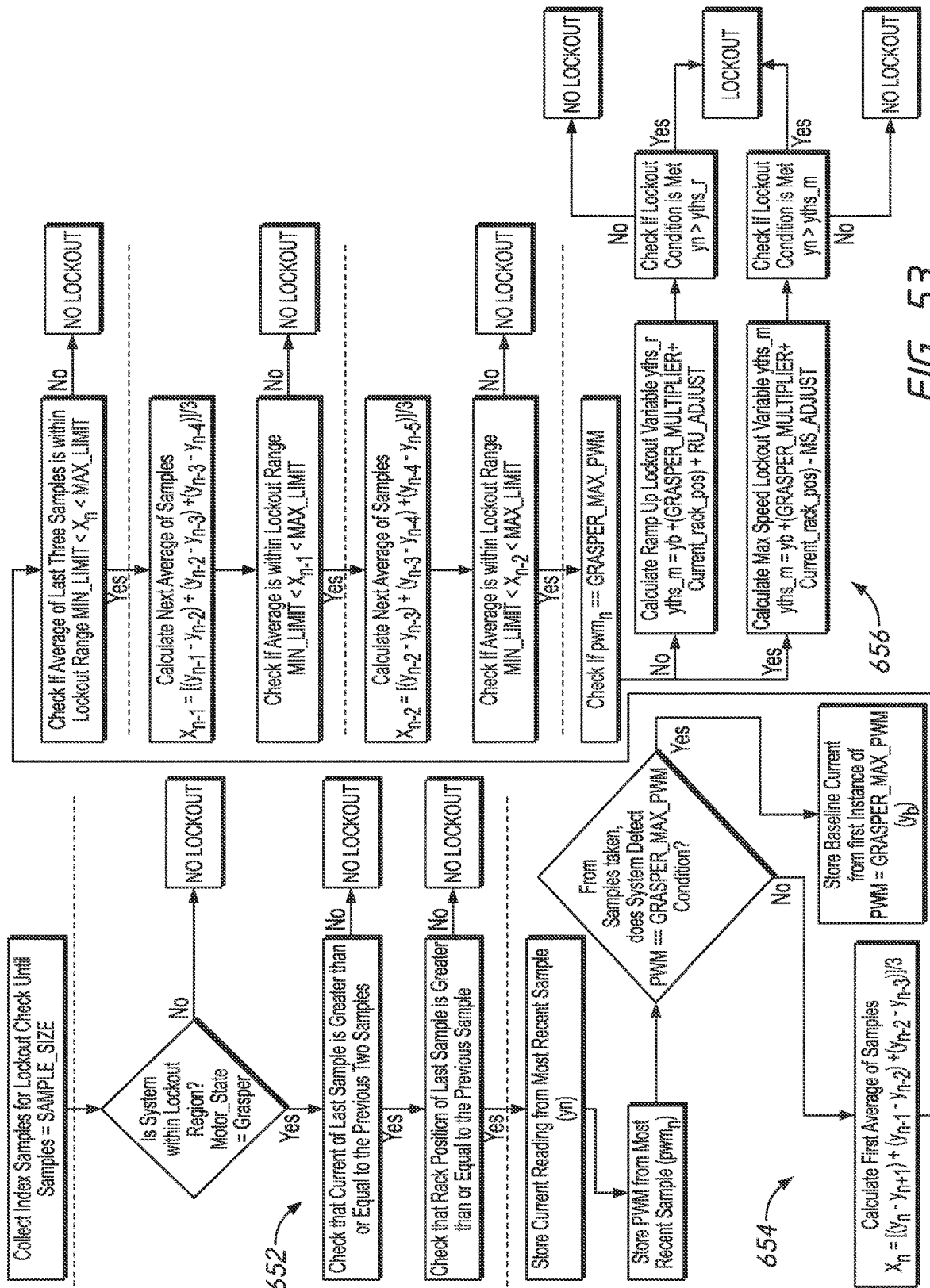
FIG. 53 an exemplary lockout mechanism control logic profile for an embodiment of powered handle assembly.

In operation of the lockout module, a current threshold is calculated for each of a maximum pwm and a ramp up assessment criteria. Depending on whether the motor is operating at maximum pwm or is considered to be ramping up, the monitored current is compared to the corresponding calculated current threshold. If the monitored current exceeds the corresponding calculated current threshold, then the lockout module indicates that a lockout mechanism is engaged. In certain embodiments, the bifurcated assessment criteria is embodied in a software or firmware program operating according to the following logical structure:

yb=current baseline=y at first instance of max pwm
yths_m=max speed threshold=yb+[(5*position)−200]
yths_r=ramp up threshold=yb+[(5*position)+50]
Current must exceed current threshold=yn>yths_m: or yn>yths_r
If the above is TRUE=LOCKOUT ENGAGEMENT With reference to FIG. 53, an exemplary flow chart for a lockout module is illustrated. In the illustrated embodiment, as the control system refreshes current and position monitoring (in certain embodiments, every 10 ms), the handle collects samples until a sufficient number are collected to perform the averaging off the lockout module. The control system then assesses various initial conditions 652 including determining whether the actuator is in the lockout region and the motor current and the actuation position are both increasing. Provided the initial conditions are met, the lockout module 654 is initiated. The lockout module verifies that three consecutive current change averages fall within a predetermined acceptance window then applies bifurcated assessment criteria 656 depending on whether the motor is operating at maximum pwm or is operating at less than maximum pwm.

An additional element of the lockout algorithm is communication with the handle's light ring. The light ring is illuminated by LED assemblies to provide 360° of light to relay the status of the handle to the user (FIG. 42). The light ring can be configured to change color based off of a change to a certain state of the handle assembly. The lockout module can trigger a unique state to the control system when a lockout condition is detected, which is relayed by a light control scheme to the light ring and thereby communicated to the user.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A surgical stapling system comprising:
   a handle body, the handle body comprising a stationary handle and a trigger pivotably coupled to the handle body;
   an electric motor disposed within the handle body;
   an actuation shaft slidable within the handle body along a longitudinal axis;
   a coupler configured to removably couple to a reload shaft assembly; and
   a shaft recognition mechanism comprising a lockout sleeve longitudinally movable to a detection position upon insertion of a reload shaft to the coupler and longitudinally movable to a predetermined recognition position when the reload shaft assembly is coupled to the coupler; and
   wherein the lockout sleeve has a proximal end and a distal end, and the lockout sleeve comprises at least one tooth protruding distally from the distal end.

2. The surgical stapling system of claim 1, wherein the shaft recognition mechanism further comprises at least one lockout link coupled to the proximal end of the lockout sleeve.

3. The surgical stapling system of claim 2, wherein the shaft recognition mechanism further comprises a shaft recognition sensor positioned within the handle assembly in engagement with the lockout link.

4. The surgical stapling system of claim 3, wherein the lockout link comprises a rack positioned thereon and the shaft recognition sensor comprises a pinion engaged with the rack of the lockout link.

5. The surgical stapling system of claim 4, wherein the lockout link comprises a bend segment to position the rack in meshed engagement with the pinion.

6. The surgical stapling system of claim 5, wherein the coupler comprises a bayonet connection and wherein upon insertion of the reload shaft, the lockout sleeve is proximally displaced to the detection position, and upon rotation of the reload shaft to a coupled position, the lockout sleeve is distally displaced from the detection position to the recognition position.

* * * * *